United States Patent
Bock et al.

(10) Patent No.: US 10,934,636 B2
(45) Date of Patent: Mar. 2, 2021

(54) METHODS FOR STUDYING NUCLEIC ACIDS

(71) Applicant: CEMM—Forschungszentrum für Molekulare Medizin GmbH, Vienna (AT)

(72) Inventors: Christoph Bock, Vienna (AT); Christian Schmidl, Vienna (AT)

(73) Assignee: CEMM—Forschungszentrum für Molekulare Medizin GmbH, Vienna (AT)

( * ) Notice: Subject to any disclaimer, the term of this patent is extended or adjusted under 35 U.S.C. 154(b) by 222 days.

(21) Appl. No.: 15/751,918

(22) PCT Filed: Aug. 11, 2016

(86) PCT No.: PCT/EP2016/069121
§ 371 (c)(1),
(2) Date: Feb. 12, 2018

(87) PCT Pub. No.: WO2017/025594
PCT Pub. Date: Feb. 16, 2017

(65) Prior Publication Data
US 2018/0237951 A1    Aug. 23, 2018

(30) Foreign Application Priority Data

Aug. 12, 2015  (EP) .................................... 15180705
Oct. 14, 2015  (EP) .................................... 15189788

(51) Int. Cl.
| | | |
|---|---|---|
| C40B 50/06 | (2006.01) |
| C12Q 1/6806 | (2018.01) |
| C07K 16/44 | (2006.01) |
| C40B 50/04 | (2006.01) |
| C40B 50/08 | (2006.01) |

(52) U.S. Cl.
CPC ............. *C40B 50/06* (2013.01); *C07K 16/44* (2013.01); *C12Q 1/6806* (2013.01); *C40B 50/04* (2013.01); *C40B 50/08* (2013.01); *C07K 2317/92* (2013.01); *C12Q 2521/327* (2013.01); *C12Q 2522/10* (2013.01)

(58) Field of Classification Search
CPC ...................................................... C40B 50/06
USPC ........................................................ 506/16
See application file for complete search history.

(56) References Cited

FOREIGN PATENT DOCUMENTS

| | | | | |
|---|---|---|---|---|
| WO | 2014190214 A1 | 11/2014 | | |
| WO | WO-2014190214 A1 | * 11/2014 | ......... | C12N 15/1093 |
| WO | 2014205296 A1 | 12/2014 | | |

OTHER PUBLICATIONS

European Search Report dated Jan. 11, 2016 and received in EP 15180705.4.
Furey, Terrence, "ChIP-seq and Beyond: New and Improved Methodologies to Detect and Characterize Protein-DNA Interactions", Nature Reviews Genetics, vol. 13, No. 12, Oct. 23, 2012, pp. 840-852 (XP055235590).
International Search Report and Written Opinion dated Nov. 21, 2016 and received in PCT/EP2016/069121.
Picelli, et. al., "Tn5 Transposase and Tagmentation Procedures for Massively Scaled Sequencing Projects", Genome Research, vol. 24, No. 12, Jul. 30, 2014, pp. 2033-2040 (XP055236186).
International Preliminary Report on Patentability dated Feb. 22, 2018 and received in PCT/EP2016/069121.
European Search Report dated May 20, 2020 and received in EP 19 20 5821.
Schmidl et al., "ChIPmentation: Fast, Robust, Low-input ChIP-seq for Histones and Transcription Factors", Nature Methods, vol. 12, No. 10, pp. 963-965, (2015).
Schmidl et. al., "CeMM ChIPmentation protocol", Retrieved from the Internet: URL:http://www.medical-epigenomics.org/papers/schmidl2015/protocols/ChIPmentation-protocol.v1.0.pdf [retrieved on May 18, 2020].

* cited by examiner

*Primary Examiner* — Karla A Dines
(74) *Attorney, Agent, or Firm* — Michele M. Wales; Inhouse Patent Counsel, LLC

(57) ABSTRACT

The present invention provides a novel method for preparing a sequencing library and studying molecular interactions involving a nucleic acid. In particular, the invention relates to a method for preparing a sequencing library, the method comprising the addition of an agent binding to chromatin to a sample comprising a nucleic acid; isolating chromatin bound by said agent; addition of transposase to the isolated chromatin; isolating nucleic acid from chromatin; and obtaining a sequencing library. Moreover, the present invention relates to a method for mapping of molecular interactions involving a nucleic acid, the method comprising the addition of an agent binding to chromatin to a sample comprising a nucleic acid; isolating chromatin bound by said agent; addition of transposase to the isolated chromatin; isolating nucleic acid from chromatin; amplification of nucleic acid; sequencing of amplified nucleic acid; and identifying molecular interactions.

31 Claims, 35 Drawing Sheets

Figure 2:
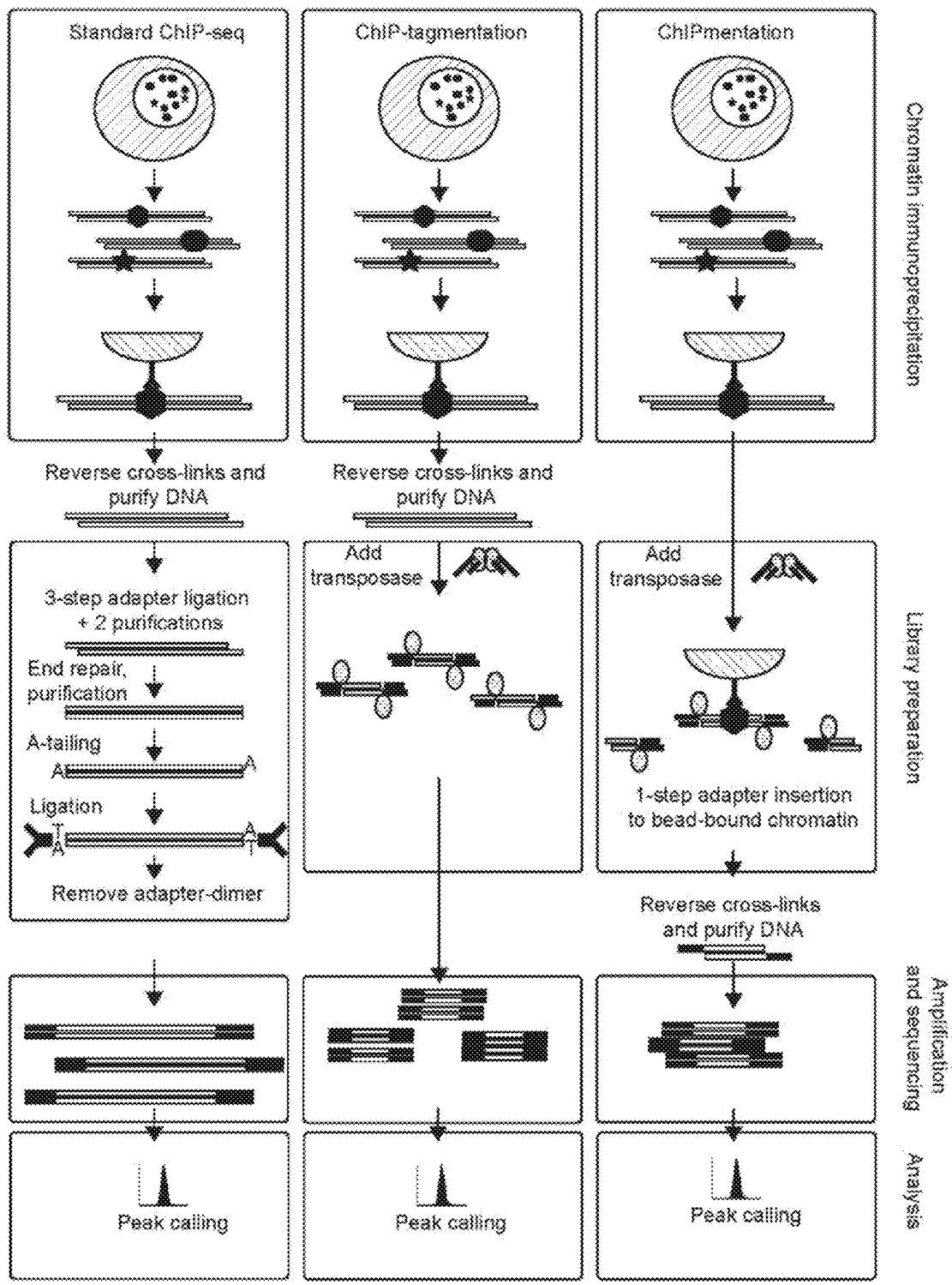

Specification includes a Sequence Listing.

Figure 1

| | Nano ChIP-seq | linDA | Small-scale ChIP | Carrier ChIP-seq | Bacterial DNA carrier ChIP-seq | iChIP | Low-cell ChIP | ChIP-exo | ChIP-nexus | ChIPmentation |
|---|---|---|---|---|---|---|---|---|---|---|
| Publication title | Genome-wide chromatin maps derived from limited numbers of hematopoietic progenitors | Single-tube linear DNA amplification (LinDA) for robust ChIP-seq | In vivo epigenomic profiling of germ cells reveals germ cell molecular signatures | A carrier-assisted ChIP-seq method for estrogen receptor-chromatin interactions from breast cancer core needle biopsy samples | Amplification of pico-scale DNA mediated by bacterial carrier DNA for small-cell-number transcription factor ChIP-seq | Chromatin state dynamics during blood formation | Bivalent chromatin marks developmental regulatory genes in the mouse embryonic germline in vivo | Comprehensive genome-wide protein-DNA interactions detected at single-nucleotide resolution | ChIP-nexus enables improved detection of in vivo transcription factor binding footprints | ChIPmentation: fast, cheap, low-input ChIP-seq for histones and transcription factors |
| Reference | Adli et al., Nature Methods 7, 615-618, 2010 | Shankaranarayanan et al., Nature Methods 8, 565-567, 2011 | Ng et al., Developmental Cell, 24, 324-333, 2013 | Zwart et al., BMC Genomics 14, 232, 2013 | Jakobsen et al., BMC Genomics 16, 46, 2015 | Lara-Astiaso et al., Science 345, 943-949, 2014 | Sachs et al., Cell Reports 3, 1777-1784, 2013 | Rhee et al., Cell 147, 1408-1419, 2011 | He et al., Nature Biotechnology 33, 395-401, 2015 | this study |
| Cell numbers required for ChIP-seq on histone marks | 10k | 5k | 1k (H3K27me3) | n/a | 10k | 500 (in multiplex reactions) | 12.5k | n/a | n/a | 10k |

Figure 1 cont.

| | Nano ChIP-seq | linDA | Small-scale ChIP | Carrier ChIP-seq | Bacterial DNA carrier ChIP-seq | iChIP | Low-cell ChIP | ChIP-exo | ChIP-nexus | ChIPmentation |
|---|---|---|---|---|---|---|---|---|---|---|
| Cell numbers required for ChIP-seq on transcription factors | n/a | 5k | n/a | 10k (1 factor tested) | 10k | 10k (1 factor tested; protocol requires sample multiplexing) | n/a | 2.5M | 10M | 100k |
| Protocol | Multistep library preparation; protocol includes pre-amplification | Multistep library preparation; protocol includes pre-amplification | Multistep library preparation; protocol includes pre-amplification | Protocol uses carrier RNA and recombinant histones | Protocol uses bacterial carrier DNA | Protocol uses additional immune-precipitation with histone H3 antibody | Commercial low-input library preparation kit (Rubicon Genomics) | Complex, multistep library preparation protocol | Complex, multistep library preparation protocol | Simple, single-step library preparation |
| Time required for library preparation | 2 days | 1.5 days of in vitro-transcription prior to conventional adapter ligation-mediated library preparation | Additional 4-5 hours prior to conventional adapter ligation-mediated library preparation | Conventional adapter ligation-mediated library preparation | Conventional adapter ligation-mediated library preparation | 1 additional day for H3 immunoprecipitation, then adapter ligation-mediated library preparation using a custom protocol | ~70 minutes | 5-6 hours library preparation + DNA purifications | 7-8 hours (ChIP-exo treatment & nexus library preparation) | 10-20 minutes library preparation |

Figure 1 cont.

| | Nano ChIP-seq | linDA | Small-scale ChIP | Carrier ChIP-seq | Bacterial DNA carrier ChIP-seq | iChIP | Low-cell ChIP | ChIP-exo | ChIP-nexus | ChIPmentation |
|---|---|---|---|---|---|---|---|---|---|---|
| Advantages | Low cell numbers for histone modifications | Low cell numbers for histone modifications and transcription factors | Very low cell numbers for histone modifications | Low cell numbers for transcription factors | Low cell numbers for histone modifications and transcription factors | Very low cell numbers; well-suited for many ChIPs with the same antibody | Low cell numbers for histone modifications | Low background, high resolution view of transcription factor binding | Low background, high resolution view of transcription factor binding (improved over ChIP-exo) | Fast; easy; cheap; low cell numbers for histone modifications and relatively low cell numbers for transcription factors; potential of high-resolution analysis of target regions |
| Drawbacks | Time-consuming protocol; additional reagent requirements; potential PCR bias due to preamplification | Time-consuming protocol; additional reagent requirements; potential PCR bias due to preamplification | Time-consuming protocol; additional reagent requirements; potential PCR bias due to preamplification | Additional reagent requirements | Increased sequencing costs due to spike-in of bacterial DNA | Time-consuming protocol; need to pool ChIPs (no single ChIPs possible); suboptimal for unbiased TF analysis due to pre- | Relies on expensive commercial library preparation kit | Time-consuming protocol; requires high cell numbers; additional reagent requirements | Time-consuming protocol; requires high cell numbers; additional reagent requirements | Additional reagent requirements (transposase + PCR primer) |

Figure 1 cont.

| Nano ChIP-seq | linDA | Small-scale ChIP | Carrier ChIP-seq | Bacterial DNA carrier ChIP-seq | iChIP | Low-cell ChIP | ChIP-exo | ChIP-nexus | ChIPmentation |
|---|---|---|---|---|---|---|---|---|---|
| | | | | | enrichment of histone H3-bound chromatin fragments | | | | |

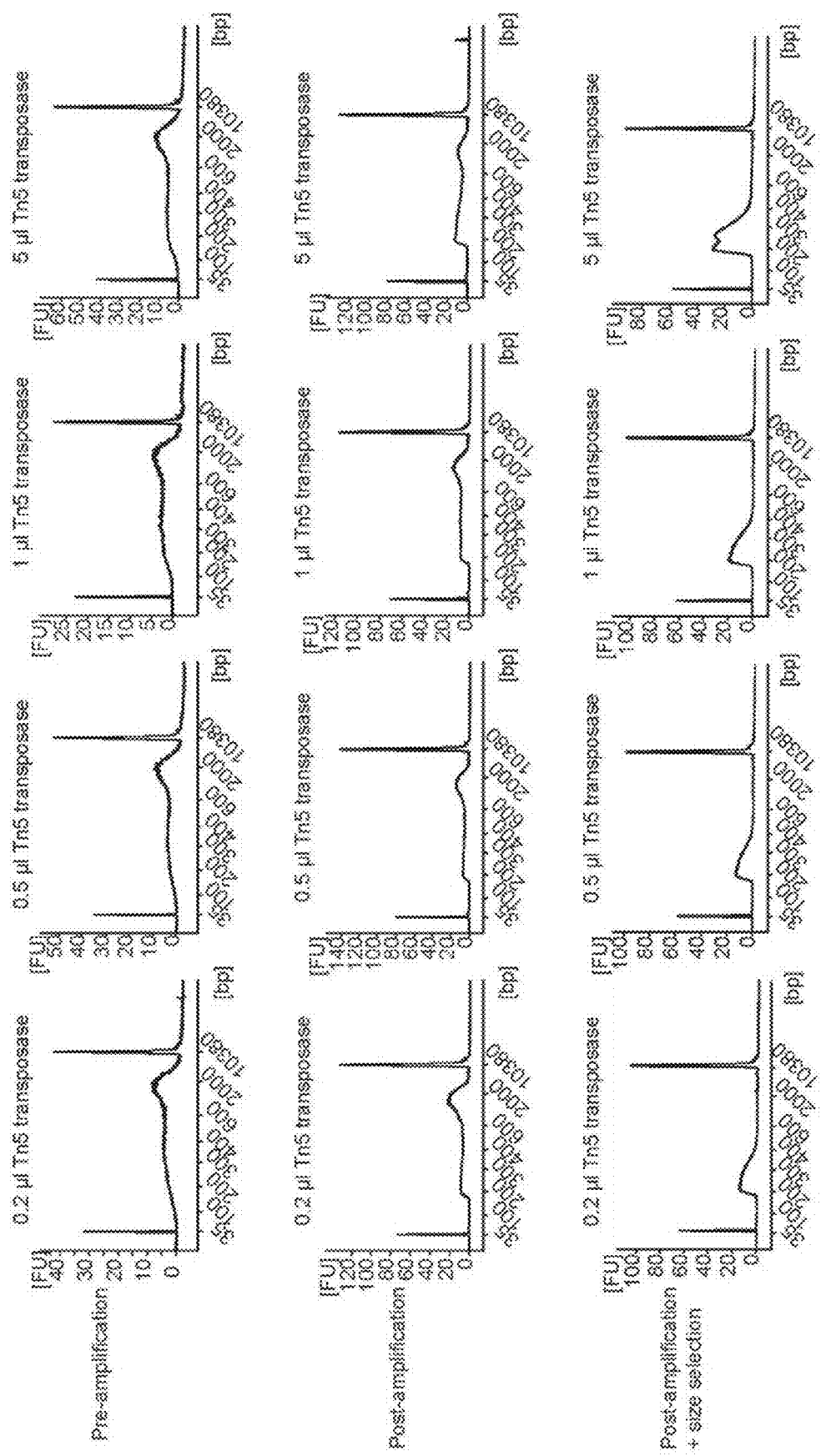

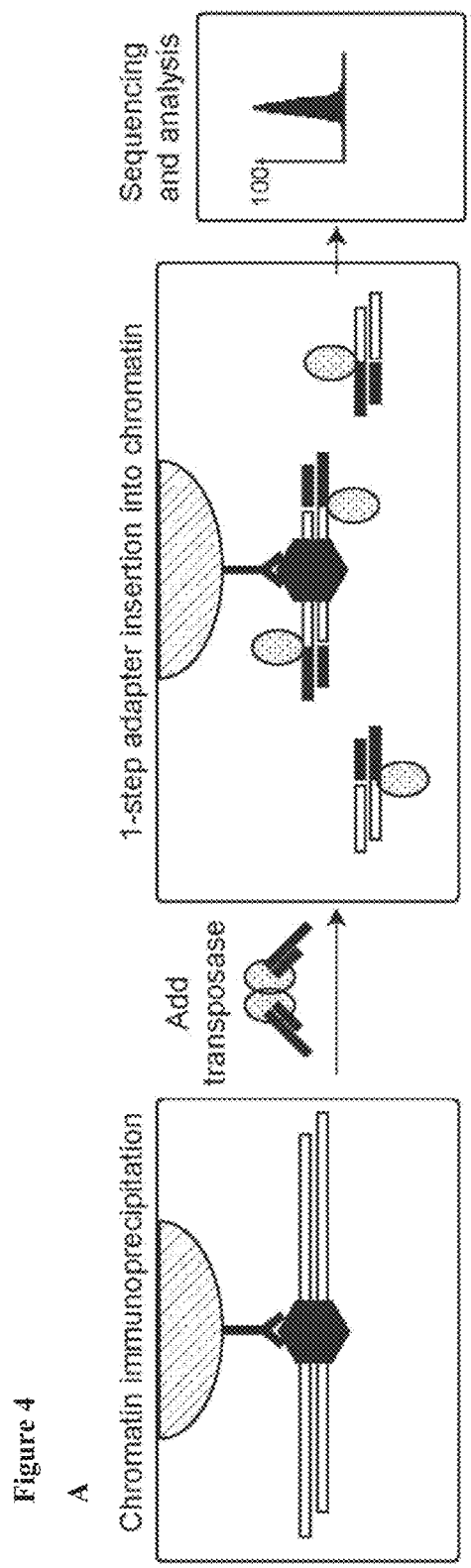

B

C

E

F

G

H

I

B

Figure 8

| id | cell_type | input_amount | protocol | antibody | repli-cate | sequencer model | read_type | read_length | read_count | genome | alignment_rate | unique_rate | internal sample id |
|---|---|---|---|---|---|---|---|---|---|---|---|---|---|
| 1 | K562 | 10M cells | ChIP-seq | H3K4me1 | 1 | HiSeq 2000 | single-read | 50 | 24,523,943 | hg19 | 99 | 94 | K562_10M_ChIP-seq_H3K4ME1_nan_1_hg19 |
| 2 | K562 | 10M cells | ChIP-seq | H3K4me1 | 2 | HiSeq 2000 | single-read | 50 | 25,448,971 | hg19 | 99 | 97 | K562_10M_ChIP-seq_H3K4ME1_nan_2_hg19 |
| 3 | K562 | 500k cells | ChIP-seq | H3K4me3 | 1 | HiSeq 2000 | single-read | 50 | 18,610,366 | hg19 | 99 | 94 | K562_500K_ChIP-seq_H3K4ME3_nan_1_hg19 |
| 4 | PBMC | 500k cells | ChIP-seq | H3K4me3 | 1 | HiSeq 2000 | single-read | 50 | 39,543,850 | hg19 | 86 | 31 | PBMC_nan_ChIP-seq_H3K4ME3_nan_1_hg19 |
| 5 | K562 | 500k cells | ChIP-seq | H3K4me3 | 2 | HiSeq 2000 | single-read | 50 | 37,576,419 | hg19 | 99 | 99 | K562_500K_ChIP-seq_H3K4ME3_nan_2_hg19 |
| 6 | K562 | 10M cells | ChIP-seq | H3K27ac | 1 | HiSeq 2000 | single-read | 50 | 27,503,214 | hg19 | 98 | 45 | K562_10M_ChIP-seq_H3K27AC_nan_1_hg19 |
| 7 | K562 | 500k cells | ChIP-seq | H3K27ac | 1 | HiSeq 2000 | single-read | 50 | 7,714,041 | hg19 | 98 | 95 | K562_500K_ChIP-seq_H3K27AC_nan_1_hg19 |
| 8 | K562 | 500k cells | ChIP-seq | H3K27me3 | 1 | HiSeq 2000 | single-read | 50 | 33,279,554 | hg19 | 98 | 96 | K562_500K_ChIP-seq_H3K27ME3_nan_1 |
| 9 | K562 | 500k cells | ChIP-seq | H3K27me3 | 2 | HiSeq 2000 | single-read | 50 | 31,605,383 | hg19 | 98 | 95 | K562_500K_ChIP-seq_H3K27ME3_nan_2_hg19 |
| 10 | K562 | 10M cells | ChIP-seq | H3K36me3 | 1 | HiSeq 2000 | single-read | 50 | 24,453,845 | hg19 | 98 | 96 | K562_10M_ChIP-seq_H3K36ME3_nan_1_hg19 |
| 11 | K562 | 10M cells | ChIP-seq | CTCF | 1 | HiSeq 2000 | single-read | 50 | 16,731,630 | hg19 | 96 | 80 | K562_10M_ChIP- |

Figure 8 cont.

| id | cell type | input amount | protocol | antibody | repli-cate | sequencer model | read_type | read length | read_count | genome | alignment rate | unique rate | internal_sample_id |
|---|---|---|---|---|---|---|---|---|---|---|---|---|---|
| 12 | K562 | 10M cells | ChIP-seq | CTCF | 2 | HiSeq 2000 | single-read | 50 | 13,292,391 | hg19 | 96 | 65 | seq_CTCF_nan_1_hg19 K562_10M_ChIP-seq_CTCF_nan_2_hg19 |
| 13 | K562 | 10M cells | ChIP-seq | GATA1 | 1 | HiSeq 2000 | single-read | 50 | 20,908,847 | hg19 | 98 | 59 | K562_10M_ChIP-seq_GATA1_nan_1_hg19 |
| 14 | K562 | 10M cells | ChIP-seq | GATA1 | 2 | HiSeq 2000 | single-read | 50 | 17,734,841 | hg19 | 98 | 92 | K562_10M_ChIP-seq_GATA1_nan_2_hg19 |
| 15 | K562 | 10M cells | ChIP-seq | PU.1 | 1 | HiSeq 2000 | single-read | 50 | 13,663,300 | hg19 | 97 | 93 | K562_10M_ChIP-seq_PU1_nan_1_hg19 |
| 16 | K562 | 10M cells | ChIP-seq | PU.1 | 2 | HiSeq 2000 | single-read | 50 | 13,453,300 | hg19 | 97 | 82 | K562_10M_ChIP-seq_PU1_nan_2_hg19 |
| 17 | K562 | 10M cells | ChIP-seq | REST | 1 | HiSeq 2000 | single-read | 50 | 27,078,470 | hg19 | 98 | 80 | K562_10M_ChIP-seq_REST_nan_1_hg19 |
| 18 | K562 | 10M cells | ChIP-seq | REST | 2 | HiSeq 2000 | single-read | 50 | 18,994,605 | hg19 | 98 | 91 | K562_10M_ChIP-seq_REST_nan_2_hg19 |
| 19 | K562 | 10M cells | ChIP-seq | Immunoglobulin G | 1 | HiSeq 2000 | single-read | 50 | 31,818,701 | hg19 | 95 | 59 | K562_10M_ChIP-seq_IGG_nan_1_hg19 |
| 20 | K562 | 500k cells | ChIP-seq | Immunoglobulin G | 1 | HiSeq 2000 | single-read | 50 | 32,545,198 | hg19 | 98 | 86 | K562_500K_ChIP-seq_IGG_nan_1_hg19 |
| 21 | K562 | 10M cells | ChIP-seq | Immunoglobulin G | 2 | HiSeq 2000 | single-read | 50 | 12,999,527 | hg19 | 93 | 34 | K562_10M_ChIP-seq_IGG_nan_2_hg19 |
| 22 | K562 | 500k cells | ChIP-seq | Immunoglobulin G | 2 | HiSeq 2000 | single-read | 50 | 36,366,641 | hg19 | 90 | 59 | K562_500K_ChIP-seq_IGG_nan_2_hg19 |
| 23 | K562 | 10M cells | ChIP-seq | Immunoglobulin G | 3 | HiSeq 2000 | single-read | 50 | 14,298,197 | hg19 | 96 | 38 | K562_10M_ChIP-seq_IGG_nan_3_hg19 |
| 24 | PBMC | 500k cells | ChIP-seq | Input | 1 | HiSeq 2000 | single-read | 50 | 4,674,578 | hg19 | 93 | 96 | PBMC_nan_ChIP-seq_Input_nan_1_hg19 |
| 25 | K562 | 10M cells | ChIPmentation | H3K4me1 | 1 | HiSeq 2000 | single-read | 50 | 14,683,831 | hg19 | 97 | 87 | K562_10M_ChIPmentation_H3K4ME1_nan_1_hg19 |

Figure 8 cont.

| id | cell type | input amount | protocol | antibody | repli-cate | sequencer model | read_type | read length | read_count | genome | alignment rate | unique rate | internal_sample_id |
|---|---|---|---|---|---|---|---|---|---|---|---|---|---|
| 26 | K562 | 10M cells | ChIPmentation | H3K4me1 | 1 | HiSeq 2000 | paired-end | 100 | 25,372,361 | hg19 | 98 | 91 | K562_10M_ChIPmentation_H3K4ME1_nan_1_h g19 |
| 27 | K562 | 10M cells | ChIPmentation | H3K4me1 | 1 | HiSeq 2000 | paired-end | 100 | 17,989,151 | hg19 | 98 | 92 | K562_10M_ChiP-Tagmentation_H3K4ME1_nan_1_hg19 |
| 28 | K562 | 10M cells | ChIPmentation | H3K4me1 | 2 | HiSeq 2000 | single-read | 50 | 13,216,471 | hg19 | 97 | 89 | K562_10M_ChIPmentation_H3K4ME1_nan_2_h g19 |
| 29 | K562 | 500k cells | ChIPmentation | H3K4me3 | 1 | HiSeq 2000 | single-read | 50 | 28,139,774 | hg19 | 98 | 79 | K562_500K_ChIPmentation_H3K4ME3_nan_1_h g19 |
| 30 | K562 | 500k cells | ChIPmentation | H3K4me3 | 2 | HiSeq 2000 | single-read | 50 | 14,306,608 | hg19 | 99 | 87 | K562_500K_ChIPmentation_H3K4ME3_nan_2_h g19 |
| 31 | K562 | 10k cells | ChIPmentation | H3K4me3 | 3 | HiSeq 2000 | single-read | 50 | 37,048,339 | hg19 | 98 | 34 | K562_10K_ChIPmentation_H3K4ME3_nan_3_h g19 |
| 32 | K562 | 10k cells | ChIPmentation | H3K4me3 | 4 | HiSeq 2000 | single-read | 50 | 35,357,419 | hg19 | 97 | 40 | K562_10K_ChIPmentation_H3K4ME3_nan_4_h g19 |
| 33 | K562 | 10M cells | ChIPmentation | H3K27ac | 1 | HiSeq 2000 | single-read | 50 | 19,377,579 | hg19 | 98 | 83 | K562_10M_ChIPmentation_H3K27AC_nan_1_h g19 |
| 34 | K562 | 10M cells | ChIPmentation | H3K27ac | 2 | HiSeq 2500 | single-read | 50 | 10,356,848 | hg19 | 99 | 92 | K562_10M_ChIPmentation_H3K27AC_nan_2_h g19 |
| 35 | K562 | 10k cells | ChIPmentation | H3K27me3 | 1 | HiSeq 2000 | single-read | 50 | 23,965,157 | hg19 | 98 | 86 | K562_10M_ChIPmentation_H3K27ME3_nan_1_hg19 |
| 36 | K562 | 500k cells | ChIPmentation | H3K27me3 | 1 | HiSeq 2000 | single-read | 50 | 22,064,368 | hg19 | 97 | 86 | K562_500K_ChIPmentation_H3K27ME3_nan_1_ hg19 |

Figure 8 cont.

| id | cell_type | input_amount | protocol | antibody | repli-cate | sequencer_model | read_type | read_length | read_count | genome | alignment_rate | unique_rate | internal_sample_id |
|---|---|---|---|---|---|---|---|---|---|---|---|---|---|
| 37 | K562 | 10k cells | ChIPmentation | H3K27me3 | 2 | HiSeq 2000 | single-read | 50 | 26,019,592 | hg19 | 98 | 88 | K562_10K_ChIPmentation_H3K27ME3_nan_2_hg19 |
| 38 | K562 | 500k cells | ChIPmentation | H3K27me3 | 2 | HiSeq 2000 | single-read | 50 | 24,286,257 | hg19 | 98 | 88 | K562_500K_ChIPmentation_H3K27ME3_nan_2_hg19 |
| 39 | K562 | 10M cells | ChIPmentation | H3K36me3 | 1 | HiSeq 2000 | single-read | 50 | 21,628,106 | hg19 | 97 | 81 | K562_10M_ChIPmentation_H3K36ME3_nan_1_hg19 |
| 40 | K562 | 10M cells | ChIPmentation | H3K36me3 | 2 | HiSeq 2500 | single-read | 50 | 18,738,407 | hg19 | 98 | 90 | K562_10M_ChIPmentation_H3K36ME3_nan_2_hg19 |
| 41 | K562 | 100k cells | ChIPmentation | CTCF | 1 | HiSeq 2000 | single-read | 50 | 11,497,781 | hg19 | 82 | 75 | K562_100K_ChIPmentation_CTCF_nan_1_hg19 |
| 42 | K562 | 10M cells | ChIPmentation | CTCF | 1 | HiSeq 2000 | single-read | 50 | 11,830,997 | hg19 | 98 | 93 | K562_10M_ChIPmentation_CTCF_nan_1_hg19 |
| 43 | K562 | 500k cells | ChIPmentation | CTCF | 1 | HiSeq 2500 | single-read | 50 | 10,464,133 | hg19 | 98 | 60 | K562_500K_ChIPmentation_CTCF_nan_1_hg19 |
| 44 | K562 | 100k cells | ChIPmentation | CTCF | 2 | HiSeq 2000 | single-read | 50 | 10,725,153 | hg19 | 98 | 64 | K562_100K_ChIPmentation_CTCF_nan_2_hg19 |
| 45 | K562 | 10M cells | ChIPmentation | CTCF | 2 | HiSeq 2000 | single-read | 50 | 10,404,401 | hg19 | 96 | 87 | K562_10M_ChIPmentation_CTCF_nan_2_hg19 |
| 46 | K562 | 500k cells | ChIPmentation | CTCF | 2 | HiSeq 2500 | single-read | 50 | 10,772,645 | hg19 | 97 | 92 | K562_500K_ChIPmentation_CTCF_nan_2_hg19 |
| 47 | K562 | 100k cells | ChIPmentation | GATA1 | 1 | HiSeq 2500 | single-read | 50 | 12,073,362 | hg19 | 97 | 83 | K562_100K_ChIPmentation_GATA1_nan_1_hg19 |
| 48 | K562 | 10M cells | ChIPmentation | GATA1 | 1 | HiSeq 2000 | single-read | 50 | 18,086,796 | hg19 | 97 | 90 | K562_10M_ChIPmentation_GATA1_nan_1_hg19 |
| 49 | K562 | 100k cells | ChIPmentation | GATA1 | 2 | HiSeq 2500 | single-read | 50 | 10,182,490 | hg19 | 96 | 79 | K562_100K_ChIPmentation_GATA1_nan_2_hg19 |

Figure 8 cont.

| id | cell type | input amount | protocol | antibody | repli-cate | sequencer model | read type | read length | read count | genome | alignment rate | unique rate | internal sample id |
|---|---|---|---|---|---|---|---|---|---|---|---|---|---|
| 50 | K562 | 10M cells | ChIPmentation | GATA1 | 2 | HiSeq 2000 | single-read | 50 | 16,679,429 | hg19 | 98 | 92 | K562_10M_ChIPmentati on_GATA1_nan_2_hg19 |
| 51 | K562 | 10M cells | ChIPmentation | PU.1 | 1 | HiSeq 2000 | single-read | 50 | 65,539,103 | hg19 | 98 | 84 | K562_10M_ChIPmentati on_PU1_nan_1_hg19 |
| 52 | K562 | 10M cells | ChIPmentation | PU.1 | 1 | HiSeq 2000 | paired-end | 100 | 27,976,709 | hg19 | 97 | 87 | K562_10M_ChIPmentati on_PU1_nan_1_hg19 |
| 53 | K562 | 500k cells | ChIPmentation | PU.1 | 1 | HiSeq 2000 | single-read | 50 | 9,937,246 | hg19 | 98 | 93 | K562_500K_ChIPmentat ion_PU1_nan_1_hg19 |
| 54 | K562 | 10M cells | ChIPmentation | PU.1 | 1 | HiSeq 2000 | paired-end | 100 | 13,476,614 | hg19 | 96 | 95 | K562_10M_ChIP-Tagmentation_PU1_nan _1_hg19 |
| 55 | K562 | 10M cells | ChIPmentation | PU.1 | 2 | HiSeq 2000 | single-read | 50 | 13,231,293 | hg19 | 98 | 93 | K562_10M_ChIPmentati on_PU1_nan_2_hg19 |
| 56 | K562 | 500k cells | ChIPmentation | PU.1 | 2 | HiSeq 2000 | single-read | 50 | 4,121,056 | hg19 | 96 | 95 | K562_500K_ChIPmentat ion_PU1_nan_2_hg19 |
| 57 | K562 | 500k cells | ChIPmentation | PU.1 | 3 | HiSeq 2500 | single-read | 50 | 10,438,095 | hg19 | 98 | 87 | K562_500K_ChIPmentat ion_PU1_nan_3_hg19 |
| 58 | K562 | 100k cells | ChIPmentation | REST | 1 | HiSeq 2500 | single-read | 50 | 10,260,884 | hg19 | 94 | 91 | K562_100K_ChIPmentat ion_REST_nan_1_hg19 |
| 59 | K562 | 10M cells | ChIPmentation | REST | 1 | HiSeq 2000 | single-read | 50 | 16,482,402 | hg19 | 97 | 81 | K562_10M_ChIPmentati on_REST_nan_1_hg19 |
| 60 | K562 | 100k cells | ChIPmentation | REST | 2 | HiSeq 2500 | single-read | 50 | 10,233,072 | hg19 | 92 | 83 | K562_100K_ChIPmentat ion_REST_nan_2_hg19 |
| 61 | K562 | 10M cells | ChIPmentation | REST | 2 | HiSeq 2000 | single-read | 50 | 24,670,236 | hg19 | 97 | 74 | K562_10M_ChIPmentati on_REST_nan_2_hg19 |
| 62 | K562 | 10M cells | ChIPmentation | Immunoglobulin G | 1 | HiSeq 2000 | single-read | 50 | 13,561,441 | hg19 | 98 | 86 | K562_10M_ChIPmentati on_IGG_nan_1_hg19 |
| 63 | K562 | 500k cells | ChIPmentation | Immunoglobulin G | 1 | HiSeq 2000 | paired-end | 100 | 14,672,785 | hg19 | 96 | 57 | K562_500K_ChIPmentat ion_IGG_1ULTN5_1_hg 19 |
| 64 | K562 | 500k cells | ChIPmentation | Immunoglobulin | 1 | HiSeq 2000 | single-read | 50 | 34,263,776 | hg19 | 97 | 50 | K562_500K_ChIPmentat |

Figure 8 cont.

| id | cell type | input amount | protocol | antibody | repli-cate | sequencer model | read type | read length | read count | genome | alignment rate | unique rate | internal_sample_id |
|---|---|---|---|---|---|---|---|---|---|---|---|---|---|
| 65 | K562 | 10M cells | ChIPmentation | Immunoglobulin G | 2 | HiSeq 2000 | single-read | 50 | 12,858,450 | hg19 | 96 | 74 | K562_10M_ChIPmentation_IGG_nan_1_hg19 |
| 66 | K562 | 500k cells | ChIPmentation | Immunoglobulin G | 2 | HiSeq 2000 | single-read | 50 | 18,412,113 | hg19 | 96 | 49 | K562_500K_ChIPmentation_IGG_nan_2_hg19 |
| 67 | K562 | 10k cells | ChIPmentation | Immunoglobulin G | 3 | HiSeq 2000 | single-read | 50 | 17,612,836 | hg19 | 94 | 22 | K562_10K_ChIPmentation_IGG_nan_3_hg19 |
| 68 | K562 | 500k cells | ChIPmentation | Immunoglobulin G | 3 | HiSeq 2000 | single-read | 50 | 7,474,797 | hg19 | 83 | 65 | K562_500K_ChIPmentation_IGG_nan_3_hg19 |
| 69 | K562 | 10k cells | ChIPmentation | Immunoglobulin G | 4 | HiSeq 2000 | single-read | 50 | 45,937,406 | hg19 | 92 | 8 | K562_10K_ChIPmentation_IGG_nan_4_hg19 |
| 70 | K562 | 10M cells | ChIPmentation | Immunoglobulin G | 4 | HiSeq 2000 | single-read | 50 | 5,670,213 | hg19 | 91 | 69 | K562_10M_ChIPmentation_IGG_nan_4_hg19 |
| 71 | K562 | 10k cells | ChIPmentation | Immunoglobulin G | 5 | HiSeq 2000 | single-read | 50 | 12,200,893 | hg19 | 87 | 28 | K562_10K_ChIPmentation_IGG_nan_5_hg19 |
| 72 | K562 | 10M cells | ChIPmentation | Immunoglobulin G | 5 | HiSeq 2000 | single-read | 50 | 10,716,675 | hg19 | 97 | 67 | K562_10M_ChIPmentation_IGG_nan_5_hg19 |
| 73 | K562 | 500k cells | ChIP-tagmentation 0.1μl Tn5 | Input | 1 | HiSeq 2000 | paired-end | 100 | 13,668,707 | hg19 | 97 | 92 | K562_500K_ChIP-Tagmentation_input_01ULTN5_1_hg19 |
| 74 | K562 | 500k cells | ChIP-tagmentation 0.1μl Tn5 | H3K4me3 | 1 | HiSeq 2000 | paired-end | 100 | 11,615,337 | hg19 | 98 | 91 | K562_500K_ChIP-Tagmentation_H3K4ME3_01ULTN5_1_hg19 |
| 75 | K562 | 500k cells | ChIPmentation 0.2μl Tn5 | H3K4me3 | 1 | HiSeq 2000 | paired-end | 100 | 13,425,746 | hg19 | 98 | 57 | K562_500K_ChIPmentation_H3K4ME3_02ULTN5_1_hg19 |
| 76 | K562 | 500k cells | ChIPmentation 0.5μl Tn5 | H3K4me3 | 1 | HiSeq 2000 | paired-end | 100 | 13,052,416 | hg19 | 98 | 89 | K562_500K_ChIPmentation_H3K4ME3_05ULTN5_1_hg19 |
| 77 | K562 | 500k cells | ChIPmentation 1μl Tn5 | H3K4me3 | 1 | HiSeq 2000 | paired-end | 100 | 12,767,587 | hg19 | 98 | 96 | K562_500K_ChIPmentation_H3K4ME3_1ULTN5_1_hg19 |

Figure 8 cont.

| id | cell_type | input_amount | protocol | antibody | repli-cate | sequencer_model | read_type | read_length | read_count | genome | alignment_rate | unique_rate | internal_sample_id |
|---|---|---|---|---|---|---|---|---|---|---|---|---|---|
| 78 | K562 | 500k cells | ChIPmentation 5μl Tn5 | H3K4me3 | 1 | HiSeq 2000 | paired-end | 100 | 11,743,183 | hg19 | 98 | 97 | K562_500K_ChIPmentation_H3K4ME3_5ULTN5_1_hg19 |
| 79 | PBMC | 100pg DNA | ChIP-tagmentation | Input | 1 | HiSeq 2000 | single-read | 50 | 18,751,591 | hg19 | 96 | 73 | PBMC_100pg_DNA_ChIP-Tagmentation_input_na n_1_hg19 |
| 80 | PBMC | 10pg DNA | ChIP-tagmentation | Input | 1 | HiSeq 2000 | single-read | 50 | 9,031,248 | hg19 | 90 | 99 | PBMC_10pg_DNA_ChIP-Tagmentation_input_na n_1_hg19 |
| 81 | PBMC | 2pg DNA | ChIP-tagmentation | Input | 1 | HiSeq 2000 | single-read | 50 | 12,031,802 | hg19 | 90 | 99 | PBMC_2pg_DNA_ChIP-Tagmentation_input_na n_1_hg19 |
| 82 | PBMC | 2pg DNA | ChIP-tagmentation | H3K4me3 | 1 | HiSeq 2000 | single-read | 50 | 11,960,898 | hg19 | 90 | 99 | PBMC_2pg_DNA_ChIP-Tagmentation_H3K4ME 3_nan_1_hg19 |
| 83 | PBMC | 100pg DNA | ChIP-tagmentation | H3K4me3 | 1 | HiSeq 2000 | single-read | 50 | 3,626,047 | hg19 | 99 | 99 | PBMC_100pg_DNA_ChIP-Tagmentation_H3K4ME 3_nan_1_hg19 |
| 84 | PBMC | 100pg DNA | ChIP-tagmentation | H3K4me3 | 1 | HiSeq 2000 | single-read | 50 | 8,393,968 | hg19 | 43 | 90 | PBMC_100pg_DNA_ChIP-Tagmentation_H3K4ME 3_nan_1_hg19 |
| 85 | PBMC | 10pg DNA | ChIP-tagmentation | H3K4me3 | 1 | HiSeq 2000 | single-read | 50 | 11,741,222 | hg19 | 92 | 99 | PBMC_10pg_DNA_ChIP-Tagmentation_H3K4ME 3_nan_1_hg19 |
| 86 | K562 | 50k cells | ATAC-seq | N/A | 1 | HiSeq 2000 | single-read | 50 | 51,962,519 | hg19 | 98 | 34 | K562_50K_ATAC-seq_nan_nan_1_hg19 |
| 87 | K562 | 50k cells | ATAC-seq | N/A | 2 | HiSeq 2000 | single-read | 50 | 32,581,411 | hg19 | 98 | 66 | K562_50K_ATAC- |

Figure 8 cont.

| id | cell_type | input_amount | protocol | antibody | repli-cate | sequencer_model | read_type | read_length | read_count | genome | alignment_rate | unique_rate | internal_sample_id |
|----|-----------|--------------|----------|----------|------------|-----------------|-----------|-------------|------------|--------|----------------|-------------|--------------------|
|    |           |              |          |          |            |                 |           |             |            |        |                |             | seq_nan_nan_2_hg19 |

A

Figure 9:
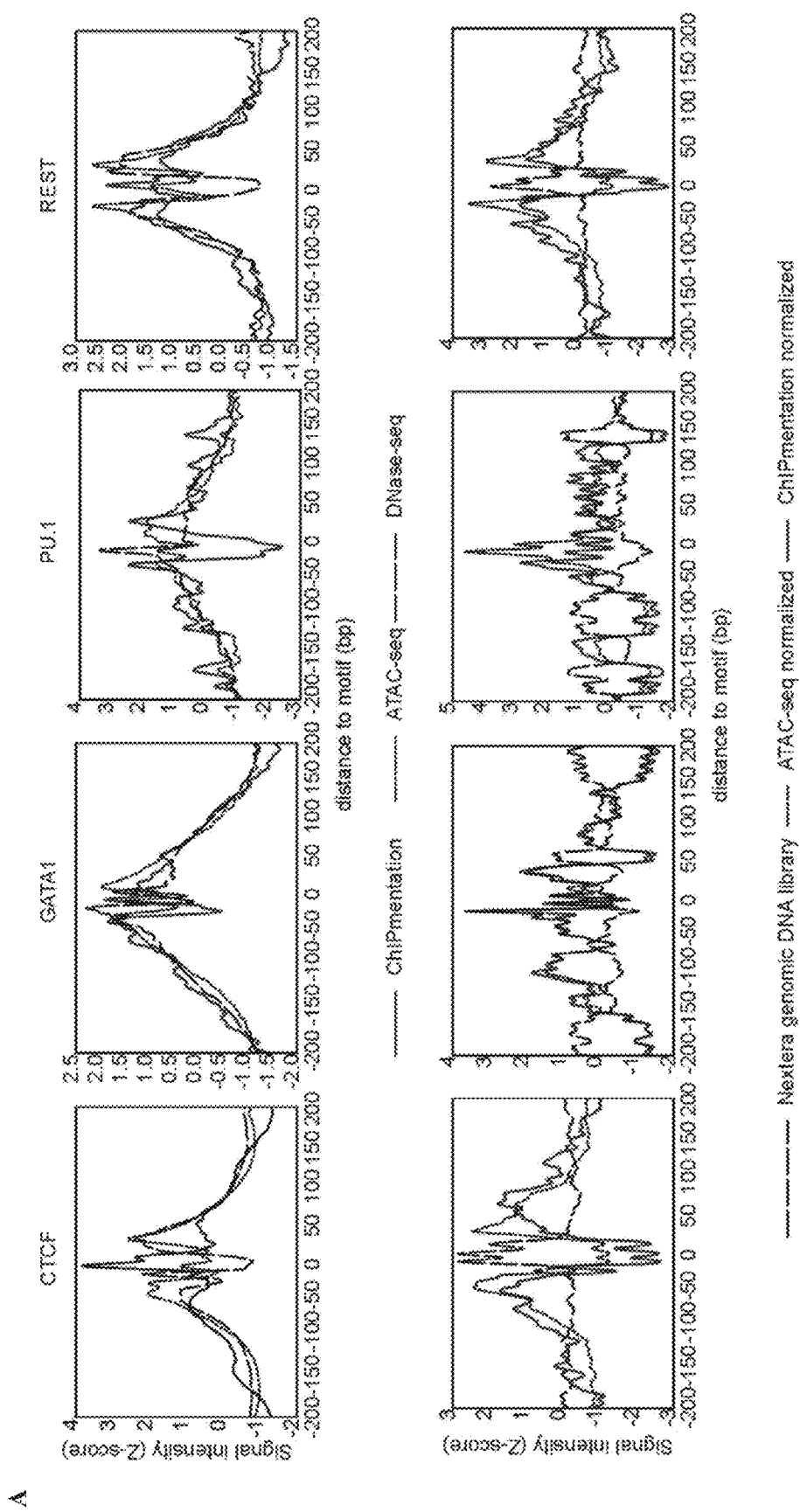

Figure 9 cont.
B
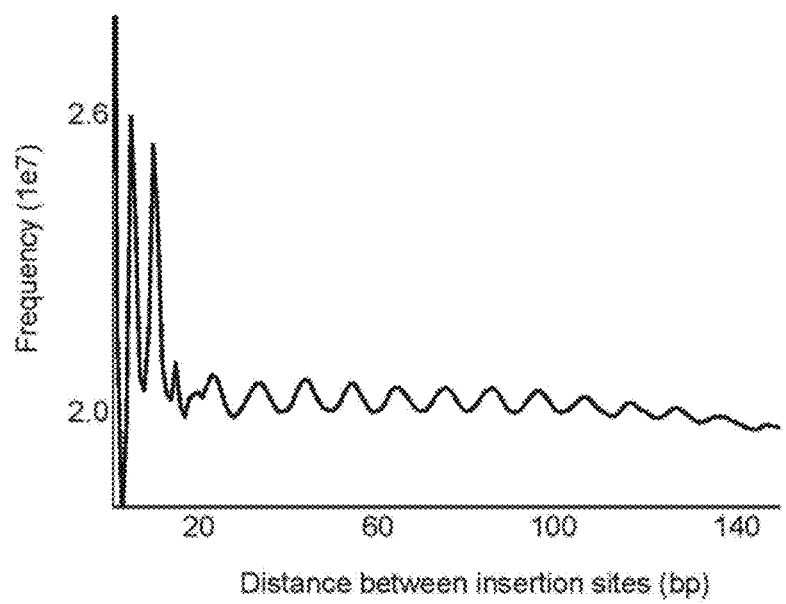
C
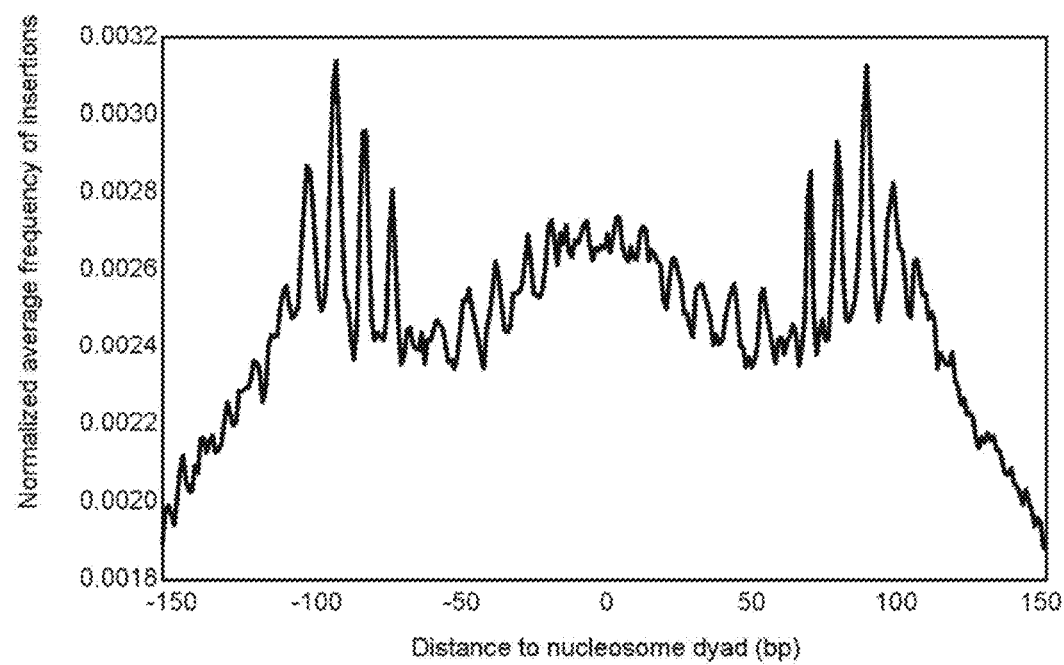

B

METHODS FOR STUDYING NUCLEIC ACIDS

CROSS-REFERENCE TO RELATED APPLICATIONS

This application is a § 371 National Stage Application of PCT/EP2016/069121 filed on Aug. 11, 2016, which claims priority to EP 15180705.4 filed on Aug. 12, 2015 and EP 15189788.1 filed on Oct. 14, 2015. All of these documents are hereby incorporated by reference in their entirety.

The present invention provides a novel method for preparing a sequencing library and studying molecular interactions involving a nucleic acid. In particular, the invention relates to a method for preparing a sequencing library, the method comprising the addition of an agent binding to chromatin to a sample comprising a nucleic acid; isolating chromatin bound by said agent; addition of transposase to the isolated chromatin; isolating nucleic acid from chromatin; and obtaining a sequencing library. Moreover, the present invention relates to a method for mapping of molecular interactions involving a nucleic acid, the method comprising the addition of an agent binding to chromatin to a sample comprising a nucleic acid; isolating chromatin bound by said agent; addition of transposase to the isolated chromatin; isolating nucleic acid from chromatin; amplification of nucleic acid; sequencing of amplified nucleic acid; and identifying molecular interactions.

The knowledge of interactions between nucleic acids and other chemical substances and/or biomolecules is of high interest for research and medicine. A well-known method to study protein-nucleic acid interactions is chromatin immunoprecipitation (ChIP), optionally followed by massive parallel sequencing (ChIP-seq). A method for studying small molecule interactions with nucleic acids and/or proteins, e.g. in chromatin, is Chem-Seq, described further below.

The ChIP method allows studying genome-wide DNA-protein interactions. It contributed substantially to our understanding of chromatin organization, histone modification as well as transcription factor binding patterns (using X-ChIP) and their influence on gene regulation in health and disease; see e.g. Nature (2012) 489, pp. 57-74 or Ernst et al. (2011) Nature 473, pp. 43-49. However, ChIP remains a relatively tedious protocol especially when applied to low-input sample (see e.g. Greenleaf, W. J. (2014) Methods). To prepare nucleic acids from ChIP for next generation sequencing (=to prepare a library), the classical approach comprises several laborious steps: (i) end-repair of the purified DNA sequences to generate blunt-end double-stranded DNA fragments with a phosphorylated 3' end; (ii) addition of an A-overhang; (iii) ligation of adaptors that have a complementary T-overhang to the double-stranded and end-repaired ChIP-DNA fragments with A-overhang. The adapters allow amplification of the DNA fragments, which ensures sufficient amount of fragments for quality control and subsequent sequencing, and it also prepares the fragments for the sequencing procedure by introduction of flow-cell ends for cluster generation and barcode sequences to multiplex sequencing experiments. The classical method comes with several limitations: (i) 5-10 ng of input material is typically needed to generate libraries which cannot be recovered from ChIPs on low amounts of cells. Hence, the recommended amount of cells for a ChIP-seq experiment is in the range of $10^6$ cells. (ii) The library procedure relies on several enzymatic reactions and DNA purifications, which make library generation a relatively laborious procedure. Imperfect enzymatic reactions as well as DNA purifications also lower the amount of recovered library fragments, which explains the high input requirements. (iii) Adapters can self-ligate and need to be excluded from amplification and sequencing. Hence, a size-selection is necessary to select against excess adapters and adapter-dimers. As an alternative to adapter ligation, other protocols were developed that generate ChIP-seq libraries by reverse transcription of DNA fragments; see ChIP Seq Kit by Clontech, Mountain View, Calif. In addition, ChIP-seq protocols for low amounts of starting material such as iChIP (Lara-Astiaso et al. (2014) Science 345, pp. 943-9), linDA (Shankaranarayanan et al. (2011) Nature Methods 8, pp. 565-7) and carrier-assisted ChIP (Zwart et al. (2013) BMC Genomics 14, 232 or Jakobsen et al. (2015) BMC Genomics 16, 46) were developed, but these protocols require additional reagents, hands-on-time or require pooling of many samples, which makes them costly, time intensive, and/or inflexible (see FIG. 1 for an overview of prior art methods and known drawbacks).

Another method to study interactions between small molecules and their protein/nucleic acid targets in chromatin is Chem-seq. The method employs chemical affinity capture coupled with massively parallel DNA sequencing to identify genomic sites where small molecules interact with their target proteins or DNA. It was first described by Anders et al. in Nature Biotechnology (2013), 32(1), pp. 92-6.

A further method for library preparation of nucleic acids was recently described. The method makes use of the development of a hyperactive Tn5 transposase for simultaneous fragmentation and adapter tagging ("tagmentation") of DNA (see Adey et al. (2010) Genome Biol 11, R119). It uses a transposase, which is pre-loaded with sequencing-compatible adapters. The transposase integrates its adapter load into DNA while fragmenting it. Only low amounts of transposase are needed to generate libraries of genomic DNA (Adey et al. (2010) Genome Biol 11, R119), bisulphite converted DNA for DNA-methylation analysis (Wang, Q. et al. (2013) Nature Protocols 8, 2022-2032), RNA-seq cDNA or other nucleic acids into sequencing-ready libraries (Picelli S. et al. (2014) Genome Res vol. 24 (12) pp. 2033-2040). In the above-cited Pirelli publication, libraries are prepared from isolated cDNA samples. However, tagmentation reactions of purified nucleic acids are extremely sensitive to varying ratios of transposase to nucleic acids, as among other parameters the amount of transposase in the tagmentation reaction determines the final size distribution of nucleic acid fragments. Thus, resulting methods require work- and cost-intensive experimentation to determine appropriate ratios of transposase and nucleic acid to achieve the desirable size distribution of nucleic acids for next generation sequencing or other downstream applications. In some cases the determination of nucleic acid fragment distribution and abundance is not even feasible, hence making it impossible to find the correct ratios of transposase to nucleic acid to prepare sequencing libraries according to, inter alia, prior art applications reviewed in Furey et al. (2012) Nature Reviews Genetics 13 (12), pp. 840-852. Furthermore, the addition of transposase to cell nuclei recovers regions of open chromatin and delivers information of nucleosome positioning as well as transcription factor footprints in regulatory regions of the genome (Buenrostro J D. et al. (2013) Nat Meth, vol. 10 (12) pp. 1213-1218).

However, the transposase was not described systematically to be suitable for use in the generation of sequencing libraries from nucleic acids subsequent to ChIP or Chem-Seq. Rather, potential disadvantages of this approach are discussed. These disadvantages result from performing tagmentation on purified DNA subsequent to ChIP, as it is described in WO 2013/078470 or WO 2014/205296. Accordingly, major drawbacks of the combination of ChIP and tagmentation are: (1) The ChIPed DNA, which is already sonicated to small fragments (200-700 bp), is in its entirety further fragmented. Hence, tagmentation can result in very small library fragments to a minimal size down to ~40 bp (Adey et al. (2010) Genome Biol 11, R119) that can be difficult to sequence as 150 bp to 200 bp fragments are recommended as minimal length for Illumina sequencing; (2) further fragmentation by tagmentation likely generates multiple sequencing reads per originally precipitated fragment, which potentially hampers downstream analysis. As an example, a 600 bp immunoprecipitated DNA fragment can yield twice the amounts of library fragments as compared with a 300 bp fragment, thereby artificially increasing the relative amount of reads in the 600 bp region. This can be problematic for correct peak calling when analyzing ChIP-seq data; (3) the approach to use purified ChIP DNA to generate sequencing libraries by tagmentation is inconvenient as correct size determination and DNA quantification are needed to set up the tagmentation reaction. As sonication can vary between samples and DNA amounts, typically varying in an order of magnitude dependent on the antibody used for the IP, these parameters would need to be determined for every ChIP sample prior to tagmentation; (4) the approach to use purified ChIP DNA to generate sequencing libraries by tagmentation is also often not possible as ChIP DNA amounts can be too low for robust quantification and size determination, which both are critical parameters to set up robust tagmentation reactions; and/or (5) tagmentation of purified ChIP DNA does not preserve the potential information of local chromatin structure at the immunoprecipitated target regions. A further method described in WO 2013/078470, referred-to as TAM-ChIP, makes use of Tn5 transposase conjugated to antibodies for ChIP. That is, the limiting factor of TAM-ChIP, as also described in WO 2014/190214, is the limitation to the use of antibody-oligonucleotide conjugates that have to be produced prior to application. This prevents the ad hoc usage of commercially available antibodies that are primarily used to study protein-DNA interactions with chromatin immunoprecipitation. Even if secondary antibody-oligonucleotide conjugates were used in TAM-ChIP to overcome the above limitations, two sets of antibodies need to be used, which increases complexity of the assay while at the same time increasing costs due to the use of a secondary antibody that is normally not used in applications such as ChIP. Accordingly, TAM-ChIP requires extensive optimizations of antibody-oligonucleotide-transposase-complexes to input chromatin ratios, as described in WO 2013/078470. As the amount of antibody-oligonucleotide-transposase complexes recruited to their recognition site determines the final library size, and because the number of recognition sites can vary from a few hundred to hundred thousand dependent on the target antigens, the ratios of antibody-oligonucleotide-transposase complexes to input chromatin has to be evaluated for each specific antibody-transposase conjugate. Thus, a more robust method insensitive with regards to rations of transposase to input chromatin is required. A further disadvantage of TAM-ChIP is the efficiency of the tagmentation reaction, which is in the range of 0.5%-5% due to the fact that only one transposome can be recruited to each target antigen. Accordingly, a low conversion of nucleic acids into sequencing library fragments and likely increase input requirements is observed. Hence, a method that can use excess transposase to tag nucleic acids on several sites in close proximity to the target sites is desirable in order to introduce sequencing adaptors next to the majority of nucleic acid fragments. Finally, TAM-ChIP requires large amounts of input chromatin. In particular, successful sequencing library preparation yielding sequencing results compareable to standard ChIP-seq can only demonstrated using 10 µg of input chromatin, which corresponds to ~1.5 Mio cells.

Thus, investigating low abundance and rarecell types including primary patient tumor cells or leukemic cells, primary patient cells from biopsies, small populations of hematopoietic cell types, low abundant cell populations obtained from developmental models or embryology research is not feasible. Hence, a method that robustly enables the use of low input amounts, i.e. less cell numbers as input to study molecular interactions, is desirable.

In light of the above, there is a need for improved methods for preparing sequencing libraries and/or mapping molecular interactions involving nucleic acids, which are independent from input amounts and which are faster, easier and/or cheaper.

Thus, the invention relates to the following items:

1. Method for preparing a sequencing library, the method comprising:
   (a) addition of an agent binding to chromatin to a sample comprising a nucleic acid;
   (b) isolating chromatin bound by said agent;
   (c) addition of transposase to isolated chromatin of step (b);
   (d) isolating nucleic acid from chromatin; and
   (e) obtaining a sequencing library.

2. Method for preparing a sequencing library, the method comprising:
   (a) addition of an antibody binding to chromatin to a sample comprising a nucleic acid;
   (b) isolating chromatin bound by said antibody;
   (c) addition of transposase to bound and isolated chromatin of step (b); (d) isolating nucleic acid from chromatin; and
   (e) obtaining a sequencing library.

3. Method for mapping of molecular interactions involving nucleic acid, the method comprising:
   (a) addition of an agent binding to chromatin to a sample comprising a nucleic acid;
   (b) isolating chromatin bound by said agent;
   (c) addition of transposase to isolated chromatin of step (b);
   (d) isolating nucleic acid from chromatin;
   (e) amplification of nucleic acid;
   (f) sequencing of amplified nucleic acid; and
   (g) identifying molecular interactions.

4. Method for mapping of molecular interactions involving nucleic acid, the method comprising:
   (a) addition of an antibody binding to chromatin to a sample comprising a nucleic acid;
   (b) isolating chromatin bound by said antibody;
   (c) addition of transposase to bound and isolated chromatin of step (b); (d) isolating nucleic acid from chromatin;
   (e) amplification of nucleic acid;
   (f) sequencing of amplified nucleic acid; and
   (g) identifying molecular interactions.

5. The method of items 1 to 4, wherein the sample comprising a nucleic acid has been prepared by
   (i) cultivating and harvesting cells;
   (ii) fixing cells;
   (iii) lysing cells and thereby obtaining a first sample comprising a nucleic acid; and (iv) sonicating the first sample and thereby obtaining a second sample comprising a nucleic acid, wherein said second sample is to be used in the method of items 1 or 2.
6. The method of items 1 to 5, wherein the method further comprises a step of reversing cross-links introduced during fixing cells.
7. The method of any one of items 1 to 6, wherein the nucleic acid is DNA.
8. The method of any one of items 5 to 7, wherein the cells comprise nucleic acid-protein complexes.
9. The method of item 8, wherein the cells are human cells, animal cells, bacterial cells, yeast cells, archaeal cells, plant cells or viruses.
10. The method of item 9, wherein the human or animal cells are diseased cells or non-diseased cells or cells derived from diseased or non-diseased tissue.
11. The method of items 9 or 10, wherein the human or animal cells are cancer cells, immune cells, blood cells or stem cells.
12. The method of item 11, wherein the cancer is a solid cancer or blood cancer.
13. The method of item 12, wherein the blood cancer is leukemia.
14. The method of item 12, wherein the solid cancer is a tumour.
15. The method of items 9, 10 or 11, wherein the animal belongs to a rare species, endangered species and/or is a model organism.
16. The method of items 9, 10 or 11, wherein the cell is an embryonic cell.
17. The method of item 5, wherein step (ii) comprises the addition of a chemical substance and/or physical means.
18. The method of item 17, wherein the chemical substance is formaldehyde or paraformaldehyde.
19. The method of item 17, wherein the physical means comprise UV-light or laser.
20. The method of item 5, wherein step (iv) comprises sonication until most of the nucleic acid fragments are 20-5000, preferably 200-300, base pairs long.
21. The method of items 1 or 2, wherein the agent binding to chromatin is an antibody or a chemical substance.
22. The method of item 21, wherein the antibody specifically binds to histones, transcription factors or proteins binding to histones and/or transcription factors.
23. The method of item 22, wherein the proteins binding to histones and/or transcription factors are nucleic acid remodeling proteins or chromatin modifying enzymes.
24. The method of item 22 or 23, wherein the histone is H3.3, H2A.Z, CENP-A, H3.2, H3.3A, H3.3B, H4 or H3.1.
25. The method of item 22, 23 or 24, wherein the histone is a modified histone, wherein the modification is methylation, acetylation, propionylation, butyrylation, crotonylation, 2-hydroxyisobutyrylation, malonylation, succinylation and/or ribosylation.
26. The method of item 25, wherein the modified histone is H3K4me1/2/3, H2BK5me1, H3K27me1/2/3, H3K9me1/2/3, H4K20me1, H3K79me1, H3K36me3, H2AK5ac, H2AK9ac, H2BK5ac, H2BK12ac, H2BK20ac, H2BK120ac, H3K4ac, H3K9ac, H3K14ac, H3K18ac, H3K23ac, H3K27ac, H3K36ac, H4K5ac, H4K8ac, H4K12ac, H4K16ac, H4K91ac, H2Aub or H2Bub.
27. The method of item 21, wherein the chemical substance is a drug or a tool compound.
28. The method of item 21 or 27, wherein the chemical substance is biotinylated.
29. The method of items 1 to 4, wherein the transposase comprises random DNA sequence tags or defined DNA sequence tags.
30. The method of item 29, wherein the transposase is a Tn5 transposase.

Accordingly, the invention provides for a method for preparing a sequencing library, the method comprising addition of an agent binding to chromatin to a sample comprising a nucleic acid; isolating chromatin bound by said agent; addition of transposase to isolated chromatin; isolating nucleic acid from chromatin; and obtaining a sequencing library.

Further embodiments are described herein and are exemplified in the scientific part.

The appended figures provide for illustrations of the present invention. Whereas the experimental data in the examples and as illustrated in the appended figures are not considered to be limiting. The technical information comprised therein forms part of this invention.

Therefore, the invention provides a method for preparing a sequencing library and a method for mapping of molecular interactions involving nucleic acid, in particular DNA. As is evident from the appended examples, the methods as provided herein comprise in particular the preparation of a sequencing library or the mapping of molecular interactions involving nucleic acid, in particular DNA, by combining steps of adding an agent binding to chromatin to a sample, isolating bound chromatin and adding a transposase to the isolated chromatin in a specific order. Accordingly, the invention provides a method for preparing a sequencing library, the method comprising the addition of an agent binding to chromatin to a sample comprising a nucleic acid; isolating chromatin bound by said agent; addition of transposase to isolated chromatin; isolating nucleic acid from chromatin; and obtaining sequencing library. The addition of transposase is to be done subsequent to isolating bound chromatin. It is preferred that the nucleic acid is DNA. The methods of the invention for mapping of molecular interactions involving nucleic acid comprise the addition of an agent binding to chromatin to a sample comprising a nucleic acid; isolating chromatin bound by said agent; addition of transposase to isolated chromatin; isolating nucleic acid from chromatin; amplification of nucleic acid; sequencing of amplified nucleic acid; and identifying molecular interactions. The sample comprising a nucleic acid may be a primary cell sample or a sample obtained by a culturing method. Where the sample is obtained by a culturing method, it is preferred that the methods further comprise cultivating and harvesting cells; fixing cells; lysing cells and thereby obtaining a first sample comprising a nucleic acid; and sonicating the first sample and thereby obtaining a second sample comprising a nucleic acid. It is preferred that said second sample is used in the methods of the invention. It is furthermore preferred that said nucleic acid is DNA, in particular double-stranded DNA. Where the sample comprising a nucleic acid is a primary cell sample, the methods of the invention preferably further comprise fixing cells; lysing cells and thereby obtaining a first sample comprising a nucleic acid; and sonicating the first sample and thereby obtaining a second sample comprising a nucleic acid.

Accordingly, it was surprisingly and unexpectedly found that tagmentation directly on chromatin bound by an agent specific for chromatin and isolated from unbound chromatin in a robust one-step reaction leads to a very robust general-purpose protocol that is faster, cheaper, easier, more robust, and better compatible with low-input samples as methods comprised in the prior art. Therefore, it is preferred that the addition of transposase is performed subsequent to isolating chromatin bound by the agent binding to chromatin, in particular the antibody or chemical substance. Accordingly, the present invention preferably relates to a method comprising the addition of an agent binding to chromatin to a sample comprising a nucleic acid; isolating chromatin bound by said agent; addition of transposase to isolated chromatin subsequent to isolating chromatin bound by the agent binding to chromatin; isolating nucleic acid from chromatin; and obtaining sequencing library. It is preferred that the nucleic acid is DNA. The methods of the invention for mapping of molecular interactions involving nucleic acid preferably comprise the addition of an agent binding to chromatin to a sample comprising a nucleic acid; isolating chromatin bound by said agent; addition of transposase to isolated chromatin subsequent to isolating chromatin bound by the agent binding to chromatin; isolating nucleic acid from chromatin; amplification of nucleic acid; sequencing of amplified nucleic acid; and identifying molecular interactions.

As shown in FIG. 2, the standard ChIP-seq protocol comprises the steps of fixation of cells, cell lysis, sonication of chromatin and immunoprecipitation with a specific antibody bound to beads. Reverse-crosslinking is followed by purification of ChIP DNA, which is then subjected to library preparation in a multi-step procedure comprising end repair, purification, A-tailing, adapter ligation and size selection. In a first improvement of the standard ChIP-seq protocol, a method called ChIP-tagmentation was found. In ChIP-tagmentation, the purified ChIP DNA is used for tagmentation-based library preparation (see FIG. 11). The method is sensitive to varying DNA concentrations, because tagmentation of purified DNA is sensitive to the ratio of tagmentation enzyme to DNA, and DNA concentrations can be highly variable and too low to quantify in many applications of ChIP-seq.

In this regard, it was surprisingly and unexpectedly found that where the sequencing adaptors are introduced in a single step subsequent to isolation of agent-bound chromatin using tagmentation, for example, using adapter-loaded Tn5 transposase, the resulting method is insensitive to varying DNA concentrations.

Thus, the improved robustness of the methods of the invention is achieved by performing tagmentation directly on agent-bound chromatin, which is isolated from unbound chromatin, where proteins protect the nucleic acid from excessive tagmentation. The resulting protocol of the methods of the invention (for example as shown in FIG. 2, right and 4a) proved to be highly robust over a 25-fold difference in tagmentation enzyme concentrations, in terms of size distribution of libraries (FIG. 3), size distribution of sequencing reads (FIG. 4b), mapping performance (FIG. 4c), track quality (FIG. 4d), and concordance (FIG. 4e). The methods of the invention are also improved in that they do not give rise to sequencing adapter dimers and do not require any nucleic acid purification steps beyond the standard cleanup after the standard ChIP protocol.

The above advantages of the methods provided herein render them superior vis-à-vis methods known in the prior art. In particular, the methods provided herein are more flexible, cheaper, more robust, require lower amounts of sample input and allow obtainment of additional information vis-à-vis methods known in the prior art, in particular TAM-ChIP as provided in WO 2014/190214. Specifically, in TAM-ChIP specific antibodiy-oligonucleotide-conjugates or antibody-oligonucleotide-transposase-conjugates are required for transposase-mediated sequencing library preparations. In the present invention, commercially available ChIP-seq antibodies can be used ad hoc without laborsome and cost-intensive conjugation reactions. In addition, the TAM-ChIP protocol as described in WO 2014/190214 requires extensive optimization of ratios of antibodiy-oligonucleotide-transposase-conjugates to input chromatin, whereas the methods of the present invention are robust to varying transposase-to-chromatin ratios.

The addition of transposase subsequent to the isolation of the chromatin of interest, as in the mehods provided herein (by e.g. a specific antibody) has further benefits over methods known in the art. In particular, TAM-ChIP requires determination of optimized ratios of antibody-oligonucleotide-conjugates to target them to their recognition sites in chromatin. Hence, only nucleic acids in immediate proximity of the recognition sites can be tagged, resulting in a relatively low tagging frequency (0.5-5%) when a transposase is used. In contrast, the methods of the present invention allow tagmentation irrespective of the agent used to isolate the chromatin of interest. Therefore, as for the robustness of the methods of the invention regarding transposase-chromatin ratios, an excess amount of transposase can be used in the methods of the invention to maximize the efficiency of sequencing library generation. This achievement substantially lowers input requirements in the methods of the present invention compared to methods known in the art.

Moreover, addition of the transposase subsequent to isolating the chromatin of interest, unexpectedly allows efficient sequencing library preparation using low amounts of transposase enzyme. This is due to the reduced presence of unspecific template chromatin for the tagmentation reaction due to the isolation of the chromatin of interest while the remainder is discarded. The reduction of required transposase amounts is a significant cost-advantage of the methods of the invention over methods known in the art, in particular the methods described in WO 2014/205296 and WO 2014/190214.

With regard to alternative methods known in the art, e.g. those described by Picelli et al. (as cited above), that use purified DNA as the template for sequencing library preparation, the use of chromatin as a template, as in the methods of the present invention, preserves high-resolution structural information of the local chromatin context; see e.g. FIG. 9.

Therefore, the methods of the present invention, for the first time, allow the construction and amplification of sequencing libraries from chromatin to study molecular interactions without prior purification or extraction of nucleic acids, in particular as in the ultra-fast method provided herein. In addition, the methods of the invention for the first time feasibly allow large-scale chromatin accessibility mapping in disease, in particular cancer, cohorts and clinical research by providing a streamlined, low-input workflow for genome-wide mapping of histone marks and transcription factors. Given that the chromatin profiling assay provided herein is sufficiently fast and straightforward for use in a clinical sequencing laboratory, chromatin deregulation is now tractable as a source of biomarkers for example for stratified cancer therapy; see also Rendeiro et al. (2016) Nature Comm. 7, Article number 11938.

The methods of the invention were validated for five exemplary histone marks (H3K4me3, H3K27ac, H3K4me1, H3K36me3, and H3K27me3) and four transcription factors (PU.1, CTCF, GATA1, and REST). In all cases, the methods of the invention showed a similar data validity as compared to standard ChIP-Seq (FIG. 5f). However, the methods of the invention allowed the significant reduction of cell input. In particular, high-quality data was obtained for H3K4me3 and H3K27me3 as well as for GATA1 and CTCF from 10 k and 100 k cells, respectively, without any pre-amplification (FIG. 4f). In this regard, for the standard ChIP-Seq protocol at least 500 k/10M cells are recommended (histone modifications/transcription factors, respectively) as input while data using the methods of the invention was obtained using 10 k or 100 k cells, respectively, while use of 1 k cells is feasible. In this regard, 10 k cells yield about 25 ng chromatin as determined by Qubit® Fluorometer after DNA purification from 10 k cells using standard methods known in the art. Thus, the novel and inventive methods of the invention allow a reduction of cell input by at least a factor of 50-100 when compared to recommendations of input requirements for classical ChIP-seq on histone modifications or transcription factors, respectively. Thus, in contrast to standard ChIP-seq and known transposase-mediated sequencing library preparations that use purified nucleic acids or cDNA as a template for sequencing library preparation, the methods provided herein can use chromatin as a template to generate sequencing libraries.

Excellent correlations and peak overlap between the standard ChIP protocol and the methods of the invention were observed, and also between biological replicates and low-input samples prepared with either method (FIGS. 4g, 4h, 5, 6 and 7). In total, 52 libraries were sequenced using the methods of the invention, 24 libraries with standard ChIP-seq (FIG. 2, left), and 9 libraries with ChIP-tagmentation (FIG. 2, center) and observed alignment rates above 95% and unique read rates around 90% in most experiments (FIG. 8). Given that tagmentation is performed directly on chromatin, it was investigated whether the distribution of tagmentation events is influenced by local chromatin structure. In addition, patterns that are suggestive of transcription factor footprints were observed (FIG. 9a) and nucleosome binding (FIG. 9b, 9c). With tailored normalization and analysis algorithms, it is possible to infer transcription factor footprints, and it is anticipated to infer also regions of nucleosome stability, and/or nucleosome positioning from data obtained by the methods of the present invention, in addition to the regular ChIP-seq readout.

The results, also shown in the appended Examples, establish the methods of the invention as a general-purpose improvement of standard ChIP-seq that is faster (10-20 minutes excluding ChIP and the final library amplification step, FIG. 2i), more cost-effective (FIG. 10), better compatible with low-input samples (FIG. 6) and easier. It was found that the methods of the invention are extremely robust over a wide range of cell numbers and enzyme concentrations, various agents binding to chromatin, and different ChIP protocols, which minimizes the need for protocol adaptations and optimizations. Accordingly, the methods of the invention are well-suited for uses of sequencing library preparation and/or mapping of molecular interactions involving nucleic acid that involve a large number of samples, i.e. as high-throughput method, focus on rare cell populations, and/or profit from a fast, cost-effective, and robust experimental workflow. In this regard, it is also contemplated that the methods of the present invention are used in a high-throughput manner, automated manner and/or parallel manner. Accordingly, it is contemplated that high-throughput facilities and/or robots used to facilitate pipetting/improve reproducibility are used to perform the methods of the invention. The skilled person will be well-aware of suitable means to perform the methods of the invention in a high-throughput, automated and/or parallel manner. For example, multiwell-plates may be used in the methods of the invention to perform multiple experiments in a parallel manner. Such multiwell-plates may for example have 96, 384 or 1536 wells. Multiwell-plates may also be used in combination with robotics suitable for high-throughput experiments. Known robotic systems allow simultaneous execution of multiple experiments, which reduces time, costs and/or increases reliability of experimental data. For example, the Sciclone NGS Workstation (P/N SG3-31020-0300, Perkin Elmer) may be used to enable automated high-throughput sequencing sample preparation. Where experiments are performed in a high-throughput manner, it is preferred that the agent binding to chromatin, in particular the antibody or chemical substance, is attached to magnetic beads, as described further below. Magnetic beads are particularly useful in high-throughput methods as they can easily be used for isolation of bead-bound particles from unbound substances. It is also envisaged that the methods of the present invention are used in combination with a microfluidic device. For example, a poly(dimethylsiloxane) (PDMS) device, featuring a simple microfluidic chamber may be used in combination with the methods of the present invention. It is preferred that the microfluidic chamber has one inlet and one outlet, and the outlet has an on-chip pneumatic microvalve that can be partially closed by exerting a pressure at a port. Magnetic beads coated with the agent binding to chromatin, in particular the antibody or the chemical substance, are flowed into the microfluidic chamber and form a packed bed while the pneumatic microvalve is partially closed. Sonicated chromatin fragments are then flowed through the chamber and adsorbed onto the bead surface. The gaps among the beads are smaller than 2, m and facilitate rapid and high-efficiency adsorption of target chromatin fragments under the small diffusion length. The beads are then washed by oscillatory washing in two different washing buffers to remove nonspecifically adsorbed chromatin fragments. Finally, the beads are flowed out of the chamber and collected for off-chip processing. This approach, as described by Cao et al. (2015) Nature Methods (available online), in combination with the herein provided novel and inventive methods allows the further reduction of experimental time and costs. The combination of the herein provided methods with Drop-Seq, as described by Macosko et al. (2015) Cell 161 (5) pp. 1202-14 and Klein et al. (2015) Cell 161(5) pp. 1187-2201 is also contemplated.

Accordingly, the present invention relates to, inter alia, a method for preparing a sequencing library. In particular, a method for preparing a sequencing library comprising the addition of an agent binding to chromatin to a sample comprising a nucleic acid; isolating chromatin bound by said agent; addition of transposase to isolated chromatin; isolating nucleic acid from chromatin; and obtaining sequencing library.

With regard to the method wherein the agent binding to chromatin is a chemical substance other than an antibody, it is known that a substantial number of small-molecule ligands, including therapeutic drugs, elicit their effects by binding specific proteins associated with the genome. Mapping the global interactions of these chemical entities with chromatin in a genome-wide manner could provide insights into the mechanisms by which a small molecule influences cellular functions. Chem-seq can be utilized to investigate the genome-wide effects of therapeutic modalities and to understand the effects of drugs on nuclear architecture in various biological contexts. In a broader sense, these methods are useful to enhance understanding of the therapeutic mechanisms through which small molecules modulate the function and activity of genome-associated proteins. Through the identification of the cellular targets of a drug, it becomes possible to gain an increased understanding of the causes of side effects and toxicity in the early stages of drug development, which helps to reduce the attrition rate in development.

Chem-seq relies on the ability to create a biotinylated version of a small molecule of interest to allow for downstream affinity capture. Chem-seq can be carried out either in vitro or in vivo.

During in vivo Chem-seq, cultured cells in medium are treated simultaneously with either a biotinylated version of the small molecule under study or DMSO (as a control) and formaldehyde for the crosslinking of DNA, proteins and small molecules. The chromatin is then extracted from the cells, sonicated and enriched for regions containing the biotinylated molecule of interest by incubation with streptavidin magnetic beads, which have a very high affinity for biotin. The enriched chromatin fraction is then eluted from the beads, crosslinks are reverted, DNA is purified, a library is generated and subjected to next generation sequencing. Genomic regions enriched in the Chem-seq library relative to the control are associated with the small molecule under study. Accordingly, the present invention also relates to an in vivo method for mapping interactions between small molecules and nucleic acids, in particular DNA.

In vitro Chem-seq begins with the crosslinking of cultured cells in medium with formaldehyde. Cell nuclei are then harvested from the cells and their chromatin is extracted. This extract is sonicated before being incubated with streptavidin magnetic beads that are bound to a biotinylated form of our compound of interest.

This provides an opportunity for the small molecule of interest to interact with its target chromatin regions. These chromatin regions are then isolated using a magnet and DNA is purified. From the DNA a library is prepared and subjected to next generation sequencing, followed by an analysis to determine regions enriched for our small molecule of interest.

Accordingly, the present invention also relates to a method for preparing a sequencing library or mapping of molecular interactions comprising nucleic acid combining the Chem-Seq approach with tagmentation, as described above.

Within the meaning of the present invention, the term "sequencing library" refers to a nucleic acid representation, wherein each nucleic acid is identifiable by, e.g., the use of an individual sequence tag. Accordingly, "obtaining sequencing library" requires a process capable of ensuring that specific adaptor sequences are added to the ends of the nucleic acid fragments to be analyzed. This preparation of nucleic acids is frequently referred to as a "sequencing library". Most of the next generation sequencing applications require the preparation of a sequencing library, nucleic acids with specific adapters at 5' and 3' ends. For example, the Illumina sequencing workflow utilizes partially complementary adaptor oligonucleotides that are used for priming the PCR amplification and introducing the specific nucleotide sequences required for cluster generation by bridge PCR and facilitating the sequencing-by-synthesis reactions. Accordingly, the resulting sequencing library of the methods of the present invention for preparing a sequencing library is suitable for use in standard sequencing applications, e.g. next generation sequencing as described further below.

A "nucleic acid" within the meaning of the present invention is a polymer of any length composed of nucleotides, preferably having a length of more than about 50 nucleotides. The methods of the invention allow the preparation of a sequencing library comprising nucleic acids and/or the mapping of molecular interactions involving nucleic acid. The nucleic acid comprised in the starting sample of the methods of the invention preferably has a length of about 50 to about 5000 nucleotides, preferably 100 to about 1000, more preferably about 200 to about 700, even more preferably 200 to 700, most preferably 200 to 300 nucleotides. The starting sample is not to be confused with the nucleic acid comprised in cells used in the methods of the invention comprising culturing and harvesting cells; fixing cells; lysing cells; and sonicating. In this regard, sonication is used to fragment the nucleic acid comprised and obtained from cells, thereby obtaining the starting sample, also referred to as second sample where the methods comprise the additional steps of culturing and harvesting cells; fixing cells; lysing cells; and sonicating. In this regard, "nucleotides" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes. In most cases, the nucleic acids used in the methods of the invention will, however, comprise the naturally occurring pyrimidine and purine bases as deoxyribonucleotides ribonucleotides that can participate in Watson-Crick base pairing interactions. Naturally-occurring nucleotides include guanine, cytosine, adenine, thymine and uracil (G, C, A, T and U, respectively). The nucleic acid may be DNA, RNA or any other type of known nucleic acids. It is preferred that the nucleic acid is DNA, in particular double-stranded DNA.

The term "agent binding to chromatin" includes any agent that is a member of a binding complex comprising chromatin as one binding partner. For instance, the agent binding to chromatin may be a polypeptide, such as a protein or fragments thereof, in particular an antibody; a nucleic acid, e.g. an oligonucleotide, polynucleotide, and the like; or a small molecule, e.g. a chemical substance. Thus, in one embodiment, the agent binding to chromatin is a polypeptide having a binding domain specific for chromatin and/or further molecules binding to chromatin, in particular other polypeptides. For example, agents binding to chromatin may have a methyl-CpG binding domain (MBD) recognizing chromatin. It is preferred that the agent binding to chromatin is a polypeptide, in particular an antibody binding to chromatin, wherein the antibody specifically binds to chromatin, proteins, e.g. transcription factors or histones, associated with chromatin and/or DNA.

In this regard, chromatin as used herein is a complex of macromolecules found in cells, comprising DNA, protein and/or RNA. The primary functions of chromatin are 1) to package DNA into a smaller volume to fit in the cell, 2) to reinforce the DNA macromolecule to allow mitosis, 3) to prevent DNA damage, and 4) to control gene expression and DNA replication. The primary protein components of chromatin are histones that compact the DNA. The structure of chromatin depends on several factors. The overall structure depends on the stage of the cell cycle. During interphase, the chromatin is structurally loose to allow access to RNA and DNA polymerases that transcribe and replicate the DNA. The local structure of chromatin during interphase depends on the genes present on the DNA: DNA coding genes that are actively transcribed ("turned on") are more loosely packaged and are found associated with RNA polymerases (referred to as euchromatin) and transcription factors while DNA coding inactive genes ("turned off") are found associated with structural proteins and are more tightly packaged (heterochromatin). Epigenetic chemical modification of the structural proteins in chromatin also alters the local chromatin structure, in particular chemical modifications of histone proteins by methylation and acetylation; see further below.

The basic repeat element of chromatin is the nucleosome, interconnected by sections of linker DNA, a far shorter arrangement than pure DNA in solution. In addition to the core histones, there is the linker histone, H1, which contacts the exit/entry of the DNA strand on the nucleosome. The nucleosome core particle, together with histone H1, is known as a chromatosome. Nucleosomes, with about 20 to 60 base pairs of linker DNA, can form, under non-physiological conditions, an approximately 10 nm "beads-on-a-string" fibre. The nucleosomes bind DNA nonspecifically, as required by their function in general DNA packaging. There are, however, large DNA sequence preferences that govern nucleosome positioning. This is due primarily to the varying physical properties of different DNA sequences: For instance, adenine and thymine are more favorably compressed into the inner minor grooves. This means nucleosomes can bind preferentially at one position approximately every 10 base pairs (the helical repeat of DNA), where the DNA is rotated to maximise the number of A and T bases that will lie in the inner minor groove. The agents binding to chromatin, as referred-to in the present invention, may bind to any part of chromatin, euchromatin or heterochromatin. For example, the agents binding to chromatin may interact with DNA, RNA or proteins comprised in chromatin. In particular, agents binding to chromatin may interact with histones or transcription factors comprised in chromatin and/or other proteins associated with histones, transcription factors or chromatin.

In this regard, histones are highly alkaline proteins found in eukaryotic cell nuclei that package and order the DNA into structural units called nucleosomes (see above). They are the chief protein components of chromatin, acting as spools around which DNA winds, and play a role in gene regulation. Five major families of histones exist: H1/H5, H2A, H2B, H3 and H4. Histones H2A, H2B, H3 and H4 are known as the core histones, while histones H1 and H5 are known as the linker histones. Two of each of the core histones assemble to form one octameric nucleosome core, approximately 63 Angstroms in diameter (a solenoid (DNA)-like particle). 147 base pairs of DNA wrap around this core particle 1.65 times in a left-handed super-helical turn to give a particle of around 100 Angstroms across. The linker histone H1 binds the nucleosome at the entry and exit sites of the DNA, thus locking the DNA into place and allowing the formation of higher order structure. The most basic such formation is the 10 nm fiber or beads on a string conformation. This involves the wrapping of DNA around nucleosomes with approximately 50 base pairs of DNA separating each pair of nucleosomes (also referred to as linker DNA). Higher-order structures include the 30 nm fiber (forming an irregular zigzag) and 100 nm fiber, these being the structures found in normal cells. During mitosis and meiosis, the condensed chromosomes are assembled through interactions between nucleosomes and other regulatory proteins. The agents binding to chromatin, in particular the antibody or chemical substance, may interact with histones, i.e. they may specifically bind to histones and/or bind to further polypeptides and/or chemical substances associated with histones. It is preferred that the agents binding to chromatin, in particular the antibody or chemical substance, interact directly with histones.

In this regard, known human histones include five classes H1/H5, H2A, H2B, H3 and H4. The class H1 includes H1F0, H1FNT, H1FOO, H1FX, HIST1H1A, HIST1H1B, HIST1H1C, HIST1H1D, HIST1H1E and HIST1H1T. Class H2A includes H2AFB1, H2AFB2, H2AFB3, H2AFJ, H2AFV, H2AFX, H2AFY, H2AFY2, H2AFZ, HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, HIST2H2AA3 and HIST2H2AC. Class H2B includes H2BFM, H2BFS, H2BFWT, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO and HIST2H2BE. Class H3 includes HISTH3A, HISTH3B, HISTH3C, HISTH3D, HISTH3E, HISTH3F, HISTH3G, HISTH3H, HISTH3I, HISTH3J, HIST2H3C and HIST3H3. Class H4 includes HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L and HIST4H4. It is preferred that the agent binding to chromatin, in particular the antibody or chemical substance, binds to histones of class H3, in particular H3.3, H3.2, H3.3A, H3.3B or H3.1. In addition, it is preferred that the agent binding to chromatin, in particular the antibody or chemical substance, binds to H4, H2A.Z or CENP-A (the latter two containing a histone H3 related histone fold).

It is furthermore envisaged that the agents binding to chromatin, in particular the antibody or chemical substance, are specific for modified versions of the known histones. A huge catalogue of histone modifications has been described. Histone modifications have specific meanings and consequences for genomic translation and accessibility of DNA for further binding proteins and/or other chemical substances. Consequently, it is envisaged that the methods of the invention be used for identifying regions bound by modified histones that may undergo alterations in gene expression, e.g. in diseased tissues/cells such as cancer cells.

Known histone modifications include methylation, acetylation, propionylation, butyrylation, crotonylation, 2-hydroxyisobutyrylation, malonylation, succinylation and ribosylation. In particular, lysine methlyation, arginine methlyation, lysine acetylation, serine/threonine/tyrosine phosphorylation. In this regard, the addition of one, two or three methyl groups to lysine has little effect on the chemistry of the histone; methylation leaves the charge of the lysine intact and adds a minimal number of atoms so steric interactions are mostly unaffected. However, proteins containing Tudor, chromo or PHD domains, amongst others, can recognise lysine methylation with exquisite sensitivity and differentiate mono, di and tri-methyl lysine, to the extent that, for some lysines (e.g.: H4K20) mono, di and tri-methylation have different meanings. Because of this, lysine methylation is a very informative mark and dominates the known histone modification functions. Accordingly, it is envisaged that the agents binding to chromatin are specific for lysine methylated histones and/or proteins recognizing such modified histones, e.g. proteins containing Tudor, chromo or PHD domains. With regard to arginine methylated histones, similar reasoning as above applies, i.e. some protein domains—e.g., Tudor domains—can be specific for methyl arginine instead of methyl lysine. Arginine is known to be mono- or di-methylated, and methylation can be symmetric or asymmetric, potentially with different meanings. With regard to lysine acetylation, addition of an acetyl group has a major chemical effect on lysine as it neutralises the positive charge. This reduces electrostatic attraction between the histone and the negatively charged DNA backbone, loosening the chromatin structure; highly acetylated histones form more accessible chromatin and tend to be associated with active transcription. Lysine acetylation appears to be less precise in meaning than methylation, in that histone acetyltransferases tend to act on more than one lysine; presumably this reflects the need to alter multiple lysines to have a significant effect on chromatin structure. Accordingly, it is also envisaged that the agent binding to chromatin is specific for acetylated lysine and/or proteins interacting with acetylated lysine. In addition to the above, serine/threonine and/or tyrosine comprised in histones can be modified by phosphorylation. Addition of a negatively charged phosphate group can lead to major changes in protein structure, leading to the well-characterised role of phosphorylation in controlling protein function. Histone phosphorylation has clear functions as a post-translational modification, and binding domains such as BRCT (BRCA1 C Terminus domain) have been characterised. Therefore, it is also envisaged that such modified histones, i.e. modified by phosphorylation, be recognized by the agents binding to chromatin.

The modifications of histones described above and further modifications described in the art have implications for the control of transcription. In this regard, two known histone modifications are particularly associated with active transcription: Trimethylation of H3 lysine 4 (H3K4Me3) and trimethylation of H3 lysine 36 (H3K36Me3). H3K4Me3 occurs at the promoter of active genes and is performed by the COMPASS complex. The modification is an excellent mark of active promoters and the level of this histone modification at a gene's promoter is broadly correlated with transcriptional activity of the gene. The formation of this mark is tied to transcription in a rather convoluted manner: early in transcription of a gene, RNA polymerase II undergoes a switch from initiating' to 'elongating', marked by a change in the phosphorylation states of the RNA polymerase II C terminal domain (CTD). The same enzyme that phosphorylates the CTD also phosphorylates the Rad6 complex, which in turn adds a ubiquitin mark to H2B K123 (K120 in mammals). H2BK123Ub occurs throughout transcribed regions, but this mark is required for COMPASS to trim-ethylate H3K4 at promoters. Thus, in a preferred aspect of the invention, the agent binding to chromatin, in particular the antibody or chemical substance, is specific for H3K4Me3. In a further aspect, the agent binding to chromatin, in particular the antibody or chemical substance, is specific for H3K36Me3. This trimethylation occurs in the body of active genes and is deposited by the methyltransferase Set2. This protein associates with elongating RNA polymerase II, and H3K36Me3 is indicative of actively transcribed genes. H3K36Me3 is recognised by the Rpd3 histone deacetylase complex, which removes acetyl modifications from surrounding histones, increasing chromatin compaction and repressing spurious transcription. Increased chromatin compaction prevents transcription factors from accessing DNA, and reduces the likelihood of new transcription events being initiated within the body of the gene. This process therefore helps ensure that transcription is not interrupted. In addition acetylation of lysine 27 of histone H3 (H3K27ac) is present at active regulatory elements as promoters and enhancers. In genetics, an enhancer is a short (50-1500 bp) region of DNA that can be bound with proteins (activators) to activate transcription of a gene. These proteins are usually referred to as transcription factors. Enhancers are generally cis-acting, located up to 1 Mbp (1,000,000 bp) away from the gene and can be upstream or downstream from the start site, and either in the forward or backward direction. There are hundreds of thousands of enhancers in the human genome. In particular, H3K27ac was described to distinguish active from poised regulatory elements. Enrichment of H3K27ac at these elements is a good indicator for expression of the associated genetic element. Accordingly, the agent binding to chromatin, in particular the antibody or chemical substance, used in the methods of the present invention may be specific for H3K27ac. Histone modifications may also be associated with repression of gene expression. For example, H3K27Me3, H3K9Me2/3 and H4K20Me3 are known to be associated with repressed genes. H3K27Me3 is deposited by the polycomb complex PRC2. It is a clear marker of gene repression, and is likely bound by other proteins to exert a repressive function. Another polycomb complex, PRC1, can bind H3K27Me3 and adds the histone modification H2AK119Ub which aids chromatin compaction. The Di and tri-methylation of H3 lysine 9 (H3K9Me2/3) is a well-characterised marker for heterochromatin, and is therefore strongly associated with gene repression. The same applies to H4K20Me3, which is tightly associated with heterochromatin. This mark is placed by the Suv4-20h methyltransferase, which is at least in part recruited by heterochromatin protein 1. Accordingly, it is also contemplated that the agents binding to chromatin used in the methods of the invention specifically bind to such modified histones associated with repressed genes and/or proteins associated therewith.

Modifications of histones also play a role in DNA repair and chromosome condensation. For example, marking sites of DNA damage is an important function for histone modifications. It also protects DNA from getting destroyed by ultraviolet radiation of sun. For example, phosphorylated H2AX (also known as gamma H2AX) is a marker for DNA double strand breaks, and forms part of the response to DNA damage. H2AX is phosphorylated early after detection of DNA double strand break, and forms a domain extending many kilobases either side of the damage. Gamma H2AX acts as a binding site for the protein MDC1, which in turn recruits key DNA repair proteins and as such, gamma H2AX forms a vital part of the machinery that ensures genome stability. Also, H3K56Acx is required for genome stability. H3K56 is acetylated by the p300/Rtt109 complex, but is rapidly deacetylated around sites of DNA damage. H3K56 acetylation is also required to stabilise stalled replication forks, preventing dangerous replication fork collapses. Phosphorylation of H3 at serine 10 (phospho-H3S10) is associated with condensed, but H3S10 phosphorylation is also present at certain chromosome sites outside mitosis, for example in pericentric heterochromatin of cells during G2. H3S10 phosphorylation has also been linked to DNA damage caused by R loop formation at highly transcribed sites. Phosphorylation of H2B at serine 10 (yeast) or serine 14 (mammals) is also linked to chromatin condensation, but for the very different purpose of mediating chromosome condensation during apoptosis. This mark is not simply a late acting bystander in apoptosis as yeast carrying mutations of this residue are resistant to hydrogen peroxide-induced apoptotic cell death.

Accordingly, the agents binding to chromatin, in particular the antibody or chemical substance, used in the methods of the invention may specifically bind to histones, modified histones and/or other factors, in particular polypeptides such as enzymes, interacting with such histones and/or modified histones. Where the agents binding to chromatin, in particular the antibody or chemical substance, binds to modified histones, it is preferred that the agent binding to chromatin, in particular the antibody or chemical substance, binds to H3K4me1/2/3, H2BK5me1, H3K27me1/2/3, H3K9me1/2/3, H4K20me1, H3K79me1, H3K36me3, H2AK5ac, H2AK9ac, H2BK5ac, H2BK12ac, H2BK20ac, H2BK120ac, H3K4ac, H3K9ac, H3K14ac, H3K18ac, H3K23ac, H3K27ac, H3K36ac, H4K5ac, H4K8ac, H4K12ac, H4K16ac, H4K91ac, H2Aub or H2Bub.

In a further embodiment, the agents binding to chromatin, in particular the antibody or chemical substance, used in the methods of the invention specifically bind to transcription factors. A transcription factor (sometimes called a sequence-specific DNA-binding factor) is a protein that binds to specific DNA sequences, thereby controlling the rate of transcription of genetic information from DNA to messenger RNA. Exemplary transcription factors include but are not limited to AAF, abl, ADA2, ADA-NF1, AF-1, AFP1, AhR, AIIN3, ALL-1, alpha-CBF, alpha-CP 1, alpha-CP2a, alpha-CP2b, alphaHo, alphaH2-alphaH3, Alx-4, aMEF-2, AML1, AML1a, AML1b, AML1c, AML1DeltaN, AML2, AML3, AML3a, AML3b, AMY-1L, A-Myb, ANF, AP-1, AP-2alphaA, AP-2alphaB, AP-2beta, AP-2gamma, AP-3 (1), AP-3 (2), AP-4, AP-5, APC, AR, AREB6, Arnt, Arnt (774 M form), ARP-1, ATBF1-A, ATBF1-B, ATF, ATF-1, ATF-2, ATF-3, ATF-3deltaZIP, ATF-a, ATF-adelta, ATPF1, BarhlI, BarhII, BarxI, Barx2, Bcl-3, BCL-6, BD73, beta-catenin, Binl, B-Myb, BP1, BP2, brahma, BRCA1, Brn-3a, Brn-3b, Brn-4, BTEB, BTEB2, B-TFIID, C/EBPalpha, C/EBPbeta, C/EBPdelta, CACCbinding factor, Cart-1, CBF (4), CBF (5), CBP, CCAAT-binding factor, CCMT-binding factor, CCF, CCG1, CCK-Ia, CCK-Ib, CD28RC, cdk2, cdk9, Cdx-1, CDX2, Cdx-4, CFF, ChxIO, CLIMI, CLIM2, CNBP, CoS, COUP, CPI, CPIA, CPIC, CP2, CPBP, CPE binding protein, CREB, CREB-2, CRE-BPI, CRE-BPa, CREMalpha, CRF, Crx, CSBP-1, CTCF, CTF, CTF-1, CTF-2, CTF-3, CTF-5, CTF-7, CUP, CUTL1, Cx, cyclin A, cyclin TI, cyclin T2, cyclin T2a, cyclin T2b, DAP, DAX1, DB1, DBF4, DBP, DbpA, DbpAv, DbpB, DDB, DDB-1, DDB-2, DEF, delta-CREB, deltaMax, DF-1, DF-2, DF-3, DIx-1, DIx-2, DIx-3, DIx4 (long isoform), DIx-4 (short isoform, DIx-5, DIx-6, DP-1, DP-2, DSIF, DSIF-pl4, DSIF-pl60, DTF, DUX1, DUX2, DUX3, DUX4, E, E12, E2F, E2F+E4, E2F+p107, E2F-1, E2F-2, E2F-3, E2F-4, E2F-5, E2F-6, E47, E4BP4, E4F, E4F1, E4TF2, EAR2, EBP-80, EC2, EF1, EF-C, EGR1, EGR2, EGR3, EllaE-A, EllaE-B, EllaE-Calpha, EllaE-Cbeta, EivF, Elf-1, Elk-1, Emx-1, Emx-2, Emx-2, En-1, En-2, ENH-bind. prot, ENKTF-1, EPASI, epsilonFl, ER, Erg-1, Erg-2, ERR1, ERR2, ETF, Ets-1, Ets-1 deltaVil, Ets-2, Evx-1, F2F, factor 2, Factor name, FBP, f-EBP, FKBP59, FKHL18, FKHRL1P2, Fli-1, Fos, FOXB1, FOXC1, FOXC2, FOXD1, FOXD2, FOXD3, FOXD4, FOXE1, FOXE3, FOXF1, FOXF2, FOXGIa, FOXGIb, FOXGIc, FOXH1, FOXI1, FOXJIa, FOXJIb, FOXJ2 (long isoform), FOXJ2 (short isoform), FOXJ3, FOXKIa, FOXKIb, FOXKIc, FOXL1, FOXMIa, FOXMIb, FOXMIc, FOXN1, FOXN2, FOXN3, FOXOIa, FOXOIb, FOX02, FOX03a, FOX03b, FOX04, FOXP1, FOXP3, Fra-1, Fra-2, FTF, FTS, G factor, G6 factor, GABP, GABP-alpha, GABP-betaI, GABP-beta2, GADD 153, GAF, gammaCMT, gammaCACI, gammaCAC2, GATA-1, GATA-2, GATA-3, GATA-4, GATA-5, GATA-6, Gbx-1, Gbx-2, GCF, GCMa, GCNS, GF1, GLI, GLI3, GR alpha, GR beta, GRF-1, Gsc, GscI, GT-IC, GT-IIA, GT-IIBalpha, GT-IIBbeta, H1TF1, H1TF2, H2RIIBP, H4TF-1, H4TF-2, HAND1, HAND2, HB9, HDAC1, HDAC2, HDAC3, hDaxx, heat-induced factor, HEB, HEBI-p67, HEBI-p94, HEF-1B, HEF-1T, HEF-4C, HEN1, HEN2, HesxI, Hex, HIF-1, HIF-Ialpha, HIF-Ibeta, HiNF-A, HiNF-B, HINF-C, HINF-D, HiNF-D3, HiNF-E, HiNF-P, HIP1, HIV-EP2, HIf, HLTF, HLTF (Met123), HLX, HMBP, HMG I, HMG I(Y), HMG Y, HMGI-C, HNF-IA, HNF-IB, HNF-IC, HNF-3, HNF-3alpha, HNF-3beta, HNF-3gamma, HNF4, HNF-4alpha, HNF4alphaI, HNF-4alpha2, HNF-4alpha3, HNF-4alpha4, HNF4gamma, HNF-6alpha, hnRNP K, HOX11, HOXAI, HOXAIO, HOXAIO PL2, HOXAI I, HOXA13, HOXA2, HOXA3, HOXA4, HOXA5, HOXA6, HOXA7, HOXA9A, HOXA9B, HOXB-1, HOXB13, HOXB2, HOXB3, HOXB4, HOXBS, HOXB6, HOXA5, HOXB7, HOXB8, HOXB9, HOXC10, HOXC11, HOXC12, HOXC13, HOXC4, HOXC5, HOXC6, HOXC8, HOXC9, HOXD10, HOXD11, HOXD12, HOXD13, HOXD3, HOXD4, HOXD8, HOXD9, Hp55, Hp65, HPX42B, HrpF, HSF, HSF1 (long), HSF1 (short), HSF2, hsp56, Hsp90, IBP-1, ICER-II, ICER-ligamma, ICSBP, Idl, Idl H', Id2, Id3, Id3/Heir-1, IF1, IgPE-1, IgPE-2, IgPE-3, IkappaB, IkappaB-alpha, IkappaB-beta, IkappaBR, II-I RF, IL-6 RE-BP, 11-6 RF, INSAF, IPF1, IRF-1, IRF-2, B, IRX2a, Irx-3, Irx-4, ISGF-1, ISGF-3, ISGF3alpha, ISGF-3gamma, 1st-1, ITF, ITF-1, ITF-2, JRF, Jun, JunB, JunD, kappay factor, KBP-1, KER1, KER-1, Koxl, KRF-1, Ku autoantigen, KUP, LBP-1, LBP-Ia, LBXI, LCR-FI, LEF-1, LEF-IB, LF-A1, LHX1, LHX2, LHX3a, LHX3b, LHXS, LHX6.1a, LHX6.1b, LIT-1, LmoI, Lmo2, LMX1A, LMX1B, L-Myl (long form), L-Myl (short form), L-My2, LSF, LXRalpha, LyF-1, Lyl-I, M factor, MadI, MASH-1, MaxI, Max2, MAZ, MAZ1, MB67, MBF1, MBF2, MBF3, MBP-1 (1), MBP-1 (2), MBP-2, MDBP, MEF-2, MEF-2B, MEF-2C (433 AA form), MEF-2C (465 AA form), MEF-2C (473 M form), MEF-2C/delta32 (441 AA form), MEF-2D00, MEF-2D0B, MEF-2DA0, MEF-2DAO, MEF-2DAB, MEF-2DA'B, Meis-1, Meis-2a, Meis-2b, Meis-2c, Meis-2d, Meis-2e, Meis3, MeoxI, MeoxIa, Meox2, MHox (K-2), Mi, MIF-1, Miz-1, MM-1, MOP3, MR, Msx-1, Msx-2, MTB-Zf, MTF-1, mtTFI, MxiI, Myb, Myc, Myc 1, Myf-3, Myf-4, Myf-5, Myf-6, MyoD, MZF-1, NCI, NC2, NCX, NELF, NER1, Net, NF III-a, NF NF NF-1, NF-1A, NF-1B, NF-1X, NF-4FA, NF-4FB, NF-4FC, NF-A, NF-AB, NFAT-1, NF-AT3, NF-Atc, NF-Atp, NF-Atx, Nf etaA, NF-CLEOa, NF-CLEOb, NFdeltaE3A, NFdeltaE3B, NFdeltaE3C, NFdeltaE4A, NFdeltaE4B, NFdeltaE4C, Nfe, NF-E, NF-E2, NF-E2 p45, NF-E3, NFE-6, NF-Gma, NF-GMb, NF-IL-2A, NF-IL-2B, NF-jun, NF-kappaB, NF-kappaB(-like), NF-kappaBI, NF-kappaB 1, precursor, NF-kappaB2, NF-kappaB2 (p49), NF-kappaB2 precursor, NF-kappaEI, NF-kappaE2, NF-kappaE3, NF-MHCIIA, NF-MHCIIB, NF-muEI, NF-muE2, NF-muE3, NF-S, NF-X, NF-X1, NF-X2, NF-X3, NF-Xc, NF-YA, NF-Zc, NF-Zz, NHP-1, NHP-2, NHP3, NHP4, NKX2-5, NKX2B, NKX2C, NKX2G, NKX3A, NKX3A vI, NKX3A v2, NKX3A v3, NKX3A v4, NKX3B, NKX6A, Nmi, N-Myc, N-Oct-2alpha, N-Oct-2beta, N-Oct-3, N-Oct-4, N-Oct-5a, N-Oct-5b, NP-TCII, NR2E3, NR4A2, Nrfl, Nrf-1, Nrf2, NRF-2betaI, NRF-2gammaI, NRL, NRSF form 1, NRSF form 2, NTF, 02, OCA-B, Oct-1, Oct-2, Oct-2.1, Oct-2B, Oct-2C, Oct-4A, Oct4B, Oct-5, Oct-6, Octa-factor, octamer-binding factor, oct-B2, oct-B3, Otxl, Otx2, OZF, pl07, pl30, p28 modulator, p300, p38erg, p45, p49erg,-p53, p55, p55erg, p65delta, p67, Pax-1, Pax-2, Pax-3, Pax-3A, Pax-3B, Pax-4, Pax-5, Pax-6, Pax-6/Pd-5a, Pax-7, Pax-8, Pax-8a, Pax-8b, Pax-8c, Pax-8d, Pax-8e, Pax-8f, Pax-9, Pbx-Ia, Pbx-Ib, Pbx-2, Pbx-3a, Pbx-3b, PC2, PC4, PC5, PEA3, PEBP2alpha, PEBP2beta, Pit-1, PITX1, PITX2, PITX3, PKNOX1, PLZF, PO-B, Pontin52, PPARalpha, PPARbeta, PPARgammaI, PPARgamma2, PPUR, PR, PR A, pRb, PRD1-BF1, PRDI-BFc, Prop-1, PSE1, P-TEFb, PTF, PTFalpha, PTFbeta, PTFdelta, PTFgamma, Pu box binding factor, Pu box binding factor (B JA-B), PU.1, PuF, Pur factor, RI, R2, RAR-alphaI, RAR-beta, RAR-beta2, RAR-gamma, RAR-gammaI, RBP60, RBP-Jkappa, Rel, RelA, RelB, RFX, RFXI, RFX2, RFX3, RFXS, RF-Y, RORalphaI, RORalpha2, RORalpha3, RORbeta, RORgamma, Rox, RPF1, RPGalpha, RREB-1, RSRFC4, RSRFC9, RVF, RXR-alpha, RXR-beta, SAP-Ia, SAPIb, SF-1, SHOX2a, SHOX2b, SHOXa, SHOXb, SHP, SIII-pl IO, SIII-pI5, SIII-pI8, SIM', Six-1, Six-2, Six-3, Six-4, Six-5, Six-6, SMAD-1, SMAD-2, SMAD-3, SMAD-4, SMAD-5, SOX-11, SOX-12, Sox-4, Sox-5, SOX-9, SpI, Sp2, Sp3, Sp4, Sph factor, Spi-B, SPIN, SRCAP, SREBP-Ia, SREBP-Ib, SREBP-Ic, SREBP-2, SRE-ZBP, SRF, SRY, SRPI, Staf-50, STATlalpha, STATIbeta, STAT2, STAT3, STAT4, STAT6, T3R, T3R-alphaI, T3R-alpha2, T3R-beta, TAF(I)110, TAF(I)48, TAF (I)63, TAF(II)100, TAF(II)125, TAF(II)135, TAF(II)170, TAF(II)18, TAF(II)20, TAF(II)250, TAF(II)250Delta, TAF (II)28, TAF(II)30, TAF(II)31, TAF(II)55, TAF(II)70-alpha, TAF(II)70-beta, TAF(II)70-gamma, TAF-I, TAF-II, TAF-L, TaI-1, TaI-Ibeta, TaI-2, TAR factor, TBP, TBX1A, TBX1B, TBX2, TBX4, TBXS (long isoform), TBXS (short isoform), TCF, TCF-1, TCF-1A, TCF-1B, TCF-1C, TCF-1D, TCF-1E, TCF-1F, TCF-1G, TCF-2alpha, TCF-3, TCF-4, TCF-4(K), TCF-4B, TCF-4E, TCFbetaI, TEF-1, TEF-2, tel, TFE3, TFEB, TFIIA, TFIIA-alpha/beta precursor, TFIIA-alpha/beta precursor, TFIIA-gamma, TFIIB, TFIID, TFIIE, TFIIE-alpha, TFIIE-beta, TFIIF, TFIIF-alpha, TFIIF-beta, TFIIH, TFIIH*, TFIIH-CAK, TFIIH-cyclin H, TFIIH-ERCC2/CAK, TFIIH-MAT1, TFIIH-M015, TFIIH-p34, TFIIH-p44, TFIIH-p62, TFIIH-p80, TFIIH-p90, TFII-I, Tf-LFI, Tf-LF2, TGIF, TGIF2, TGT3, THRAI, TIF2, TLE1, TLX3, TMF, TR2, TR2-11, TR2-9, TR3, TR4, TRAP, TREB-1, TREB-2, TREB-3, TREFI, TREF2, TRF (2), TTF-1, TXRE BP, TxREF, UBF, UBP-1, UEF-1, UEF-2, UEF-3, UEF-4, USF1, USF2, USF2b, Vav, Vax-2, VDR, vHNF-IA, vHNF-IB, vHNF-IC, VITF, WSTF, WT1, WT1I, WT1 I-KTS, WT1 I-del2, WT1-KTS, WTI-del2, X2BP, XBP-1, XW-V, XX, YAF2, YB-1, YEBP, YY1, ZEB, ZF1, ZF2, ZFX, ZHX1, ZIC2, ZID, ZNF 174 and the like.

Transcription factors perform this function alone or with other proteins in a complex, by promoting (as an activator), or blocking (as a repressor) the recruitment of RNA polymerase (the enzyme that performs the transcription of genetic information from DNA to RNA) to specific genes. Accordingly, the agent binding to chromatin may interact directly with a transcription factor, the complex comprising one or more transcription factors and/or proteins associated with transcription factors. A defining feature of transcription factors is that they contain one or more DNA-binding domains (DBDs), which attach to specific sequences of DNA adjacent to the genes that they regulate. Additional proteins such as coactivators, chromatin remodelers, histone acetylases, deacetylases, kinases, and methylases, while also playing crucial roles in gene regulation, lack DNA-binding domains, and, therefore, are not classified as transcription factors. However, the agents binding to chromatin used in the methods of the invention may also interact with such proteins. Transcription factors bind to either enhancer or promoter regions of DNA adjacent to the genes that they regulate. Depending on the transcription factor, the transcription of the adjacent gene is either up- or down-regulated. Transcription factors use a variety of mechanisms for the regulation of gene expression. These mechanisms include: stabilize or block the binding of RNA polymerase to DNA; catalyze the acetylation or deacetylation of histone proteins. The transcription factor can either do this directly or recruit other proteins with this catalytic activity. Many transcription factors use one or the other of two opposing mechanisms to regulate transcription: histone acetyltransferase (HAT) activity—acetylates histone proteins, which weakens the association of DNA with histones, which make the DNA more accessible to transcription, thereby up-regulating transcription; and/or histone deacetylase (HDAC) activity—deacetylates histone proteins, which strengthens the association of DNA with histones, which make the DNA less accessible to transcription, thereby down-regulating transcription. The mechanisms for the regulation of gene expression also include recruiting coactivator or corepressor proteins to the transcription factor DNA complex.

Many transcription factors are of clinical significance for at least two reasons: (1) mutations can be associated with specific diseases, and (2) they can be targets of medications. Accordingly, the agents binding to chromatin used in the methods of the present invention may be relevant in the diagnosis and/or treatment of diseases associated with transcription factors. For example, due to their important roles in development, intercellular signaling, and cell cycle, some human diseases have been associated with mutations in transcription factors. In addition, many transcription factors are either tumor suppressors or oncogenes, and, thus, mutations or aberrant regulation of them is associated with cancer. At least three groups of transcription factors are known to be important in human cancer: (1) the NF-kappaB and AP-1 families, (2) the STAT family and (3) the steroid receptors. Further transcription factors involved in human diseases are shown in the below table:

TABLE 1

| Condition | Description | Locus |
| --- | --- | --- |
| Rett syndrome | Mutations in the MECP2 transcription factor are associated with Rett syndrome, a neurodevelopmental disorder. | Xq28 |
| Diabetes | A rare form of diabetes called MODY (Maturity onset diabetes of the young) can be caused by mutations in hepatocyte nuclear factors (HNFs) or insulin promoter factor-1 (IPF1/Pdx1). | multiple |
| Developmental verbal dyspraxia | Mutations in the FOXP2 transcription factor are associated with developmental verbal dyspraxia, a disease in which individuals are unable to produce the finely coordinated movements required for speech. | 7q31 |

TABLE 1-continued

| Condition | Description | Locus |
| --- | --- | --- |
| Autoimmune diseases | Mutations in the FOXP3 transcription factor cause a rare form of autoimmune disease called IPEX. | Xp11.23-q13.3 |
| Li-Fraumeni syndrome | Caused by mutations in the tumor suppressor p53. | 17p13.1 |
| Breast cancer | The STAT family is relevant to breast cancer. | multiple |
| Multiple cancers | The HOX family are involved in a variety of cancers. | multiple |

Accordingly, the agents binding to chromatin, in particular the antibody or chemical substance, used in the methods of the present invention may interact with transcription factors known to be associated with diseases, e.g. cancer. In this regard, the methods of the invention may be used to study the interaction between DNA and transcription factors in a diseased cell and/or cells derived from diseased tissue. Also, the methods of the present invention can be used to study interactions between drugs and DNA/transcription factors. In this regard, approximately 10% of currently prescribed drugs directly target the nuclear receptor class of transcription factors. Examples include tamoxifen and bicalutamide for the treatment of breast and prostate cancer, respectively, and various types of anti-inflammatory and anabolic steroids. In addition, transcription factors are often indirectly modulated by drugs through signaling cascades.

In accordance with the above, the present invention relates to methods for mapping of molecular interactions involving nucleic acid, in particular DNA, wherein the method provides valuable information with regard to the interaction of polypeptides with a nucleic acid, in particular DNA. The nucleic acid may be derived from any source, e.g. cells. In particular, cells comprising nucleic acid-protein complexes. It is preferred that the cells are human cells, animal cells, bacterial cells, yeast cells, archaeal cells, plant cells or viruses. It is more preferred that the cells are human cells. However, cells may also be from non-native sources, e.g. engineered cells or artificially modified cells, in particular genetically modified cells. In addition, the human or animal cells may be diseased cells or non-diseased cells or cells derived from diseased or non-diseased tissue. In this regard, the human or animal cells may be cancer cells, immune cells, blood cells or stem cells. It is preferred that the cells are cancer cells. The cancer may be a solid cancer or blood cancer, in particular leukemia or a tumour. Known cancers associated with altered transcription, i.e. altered accessibility of DNA, modified histones, modified transcription factors and the like, are summarized by Yeh et al. (2013) Curr. Opin. Oncol. 25(6). The cells may also be embryonic cells.

Because the methods of the invention are particularly useful for analysis of low cell numbers, it is evident that sources having a limited number of cells available as source of the nucleic acid to be analyzed, are particularly envisaged. Such sources include early embryonic stages of humans or animals. In cases of diseases, in particular human diseases, the cell numbers may be restricted by the nature of the disease, e.g cancer metastasis, small primary tumors or small diseased organs, rare tissues and rare cell types. The cell numbers of human clinical samples can further be restricted by the approach to obtain the sample, e.g needle biopsies or blood draws. Accordingly, samples derived from such sources are also contemplated for use in the methods of the present invention. In addition, cell numbers may be limited due to other restrictions, e.g. protected animals, rare animals, endangered animals or the like. Furthermore, the methods of the invention are particularly useful in single-animal studies, in particular of small animals, such as *C. elegans* or zebrafish.

In the methods of the invention, prior to preparing a sequencing library or mapping molecular interactions involving a nucleic acid, the sample comprising a nucleic acid is preferably prepared by cultivating and harvesting cells; fixing cells; lysing cells and thereby obtaining a first sample comprising a nucleic acid; and sonicating the sample and thereby obtaining a second sample comprising a nucleic acid. It is preferred that said second sample is used in the methods of the invention for preparing a sequencing library or mapping of molecular interactions involving a nucleic acid. Where the sample comprising a nucleic acid is a primary cell sample, e.g. a sample derived from a donor, the step of cultivating and harvesting may be omitted. Accordingly, where the sample comprising a nucleic acid is a primary cell sample, the methods of the invention preferably further comprise fixing cells; lysing cells and thereby obtaining a first sample comprising a nucleic acid; and sonicating the first sample and thereby obtaining a second sample comprising a nucleic acid.

Accordingly, the sample comprising a nucleic acid is preferably prepared by a method comprising cultivating and harvesting of cells. This may be done using methods well-known in the art. In particular, cultivation methods must be suitable for the cell type used in analysis. Such methods are described in, e.g. Helgason et al. (2005) Basic Cell Culture Protocols, Methods in Molecular Biology or Freshney (2010) Culture of Animal Cells, Wiley-Blackwell. Harvesting of cells is also done by well-known methods described in the art. For example, cells may be harvested by centrifugation, whereby cells are found in the resulting cell pellet while the supernatant contains the used culture medium.

Subsequent to harvesting cultivated cells, the cells may be fixed. Fixation is used to preserve a sample from decay. Accordingly, in this process, structures are preserved in a state (both chemically and structurally) as close to the native state, e.g. in living tissue, as possible. This requires a chemical fixative that can stabilise proteins and/or nucleic acids of the tissue by making them insoluble. In addition to preserving such a state, fixatives are used to crosslink macromolecules, in particular proteins and/or nucleic acids, contained in the sample.

Accordingly, crosslinking fixatives act by creating covalent chemical bonds between macromolecules, in particular proteins and/or nucleic acids. In this regard, a well-known fixative is formaldehyde. It is preferably used as a 10% Neutral Buffered Formalin (NBF), that is approx. 3.7%-4.0% formaldehyde in phosphate buffered saline. Because formaldehyde is a gas at room temperature, formalin-formaldehyde gas dissolved in water (~37% w/v)-is used when making the former fixative. Paraformaldehyde is a polymerised form of formaldehyde, usually obtained as a fine white powder, which depolymerises back to formalin when heated. Formaldehyde fixes tissue by cross-linking the proteins, primarily the residues of the basic amino acid lysine. Its effects are reversible by excess water and it avoids formalin pigmentation. Other benefits include: Long term storage and good tissue penetration. Another popular aldehyde for fixation is glutaraldehyde. It operates in a similar way to formaldehyde by causing deformation of the alpha-helix structures in proteins. However, glutaraldehyde is a larger molecule, and so its rate of diffusion across membranes is slower than formaldehyde. Consequently glutaraldehyde fixation on thicker samples may be hampered, but this problem can be overcome by reducing the size of the sample. One of the advantages of glutaraldehyde fixation is that it may offer a more rigid or tightly linked fixed product-its greater length and two aldehyde groups allow it to 'bridge' and link more distant pairs of protein molecules. It causes rapid and irreversible changes, fixes quickly, is well suited for electron microscopy, fixes well at 4° C., and gives best overall cytoplasmic and nuclear detail. However it is not ideal for immunohistochemistry staining.

Some fixation protocols call for a combination of formaldehyde and glutaraldehyde so that their respective strengths complement one another.

These crosslinking fixatives-especially formaldehyde-tend to preserve the secondary structure of proteins and may protect significant amounts of tertiary structure as well.

However, fixation may also be done using alternative means, e.g. non-chemical fixation using physical means, in particular UV-light as described by, for example, Zhang et al. (2004) Biochem Biophys Res Commun 322(3), 705-11. Alternatively or additionally, fixation may be done using a laser, in particular a UV-laser, as for example described by Benedetti et al. (2014) Methods Mol Biol 1204:24-34.

Accordingly, it is preferred that fixation is done using a chemical substance and/or physical means. In this regard, it is preferred that physical means comprise UV-light or a UV-laser. It is more preferred that fixation is done using a chemical substance, preferably formaldehyde or paraformaldehyde.

The introduced cross-links may be removed subsequent to library preparation, i.e. subsequent to addition of transposase and prior to nucleic acid isolation from chromatin. Reversing cross-links may be done using methods well-known in the art.

For example, formaldehyde crosslinks may be removed by heating the sample. Preferably, the sample is heated to about 65° C., preferably for several hours. In particular, the sample may be heated to about 65° C. for 4 hours or more, for example over night. Alternatively, the sample may be heated to about 95° C. for about 10-15 minutes. However, heating to lower temperatures, in particular to about 65° C. is preferred to retain integrity of the sample comprising nucleic acid. In addition to heating, detergents and/or salt (for example 0.5-1% SDS and/or about 300 mM NaCl) may be added to remove crosslinks. Moreover, RNase and/or Proteinase K may be added subsequent to removing-crosslinks to remove protein and/or RNA, respectively, from the sample comprising nucleic acid, in particular DNA. As an example, samples can be treated for 30 min at 37° C. with 0.5 µl 10 mg/ml RNase A DNase-free RNase, and subsequently with 1 µl 20 mg/ml proteinase K for 1-2 hour at 55° C.

In an ultra-fast set up of the methods of the present invention, the sample may be heated to high temperatures to reverse cross-links. In particular, the sample may be heated to about 95° C. to reverse cross-links. Such high temperatures significantly reduce the time required to reverse cross-links. In particular, the required time to reverse cross-links may be reduced from several hours, like about 4 hours at about 65° C., to about 10-15 minutes at about 95° C. Because the transposase used in the methods of the present invention preferably comprises oligonucleotides including adapter sequences, such adapter sequences may be integrated prior to reverse cross-links, as reversing cross-links is done subsequent to addition of transposase in the methods of the present invention. Accordingly, such high temperatures cannot be used using standard ChIP protocols. This is because heating to high temperatures would denature ChIP DNA, and due the complexity of the ChIP DNA some fragments (especially AT-rich sequences) do not re-anneal properly. When preparing a library by ligation of double-stranded adapters, ChIP DNA fragments that did not re-anneal properly are likely excluded from the final library and introduce a sequencing bias. However, in the methods of the present invention, high temperatures, like about 95° C., can be employed in order to reverse cross-links. This remarkably reduces the overall duration of the assay; see Example 14. In addition, using high temperatures to reverse cross-links, like about 95° C., avoids the step of elution from beads. Avoiding elution from beads further reduces the complexicity of the used method and further reduces the overall time required for practicing the methods of the invention. This is because elution from beads comprises the use of buffers incompatible with the subsequent PCR step, using for example SDS and/or high concentrations of salt. Such buffers render library amplification difficult or impossible without prior DNA cleanup. Accordingly, the ultra fast set up described herein makes DNA purification unnecessary. Where the methods of the present invention involve the use of high-temperatures for reversing cross-links, in particular temperatures of about 95° C., the methods preferably also comprise a step of end-repairing oligonucleotides introduced during the transposase reaction prior the application of high-temperatures, i.e. a step of filling-in adapter sequences, in particular filling-in adapter sequences on the reverse strand opposite to the strand comprising the oligonucleotide introduced during the transposase reaction. Therefore, the methods of the present invention, where high temperatures, like about 95° C., are used to reverse cross-links, preferably comprise a step of addition of PCR ingredients for end repair prior to the application of high-temperature. Preferably, the end repair is done on the beads using PCR MM prior to heating at end-repair conditions, e.g. 72° C. for 5 min using a DNA polymerase, like Taq polymerase. However, end-repair may also be done using an end-repair mix at lower temperatures.

Accordingly, the present invention provides an ultra-fast method for preparing a sequencing library. The ultra-fast method for preparing a sequencing library comprises the addition of an agent binding to chromatin to a sample comprising a nucleic acid, wherein the sample has been fixed by cross-linking; isolating chromatin bound by said agent; addition of transposase to isolated chromatin bound by said agent; filling-in oligonucleotid ends generated during transposase reaction; reverse cross-links at high temperatures, preferably at about 95° C.; and obtaining a sequencing library. In addition, the present invention relates to an ultra-fast method for mapping of molecular interactions involving nucleic acid. The ultra-fast method for mapping of molecular interactions comprises the addition of an agent binding to chromatin to a sample comprising a nucleic acid; isolating chromatin bound by said agent; addition of transposase to isolated chromatin bound by said agent; filling-in oligonucleotid ends generated during transposase reaction; reverse cross-links at high temperatures, preferably at about 95° C.; amplification of nucleic acid; sequencing of amplified nucleic acid; and identifying molecular interactions. Ultra-fast in this regard means that the ultra-fast methods of the invention significantly reduce overall experiment time expected for known methods. In particular, the ultra-fast methods of the present invention allow the preparation of a sequencing library or mapping of molecular interactions, respectively, in less than a working day, i.e. less than about 10 hours. The overall time required to prepare a sequencing library from obtaining a sample, e.g. obtaining a blood sample from a donor, to obtaining a sequencing library is in the range of about 15 hours.

The methods of the invention may further comprise a step of lysing cells. Lysing refers to the breaking down of cellular membranes. This may be achieved by methods well-known in the art. In particular, lysis may be achieved by mechanical means or chemical means. For example, mechanical disruption of cell membranes, as by repeated freezing and thawing, sonication, pressure, or filtration may be employed. However, it is preferred that lysis is achieved by chemical means using, in particular, enzymes or detergents or other chaotropic agents. Preferred methods of cell lysis are described in Thermo Scientific Pierce Cell Lysis Technical Handbook or Lottspeich, Engels (2012) Bioanalytik, Springer Spektrum. In this regard, lysis as used in the methods of the invention is done to isolate nucleic acids from the cellular sample, thereby obtaining a first sample comprising a nucleic acid. Said first sample is used for further analysis using the methods of the present invention, i.e. said first sample is either used for further preparation of the sample, in particular using sonication, or directly analysed using the methods of the invention for preparing a sequencing library or mapping of molecular interactions involving a nucleic acid.

Accordingly, in one embodiment, subsequent to cell lysis, the methods of the invention may comprise a step of sonication. Sonication has numerous effects, both chemical and physical. In biological applications, sonication is commonly used to disrupt or deactivate a biological material. For example, sonication is often used to disrupt cell membranes and release cellular contents. This process is called sonoporation. Sonication is also used to fragment molecules of nucleic acids, in particular DNA, in which the nucleic acid, in particular DNA, subjected to brief periods of sonication is sheared into smaller fragments. Sonication is also used to fragment complexes of molecules containing nucleic acids and protein, in particular chromatin containing nucleic acids, in particular DNA, in which the complexes are subjected to brief periods of sonication where the nucleic acid content in the complex, in particular DNA, is sheared into smaller fragments. In this regard, it is well-known how to adjust sonication intensity to generate fragments of nucleic acids, in particular DNA, having particular lengths and/or wherein most of the fragments contained in a sample comprising a nucleic acid, in particular DNA, have a particular lengths. In this regard, it is preferred that the sample comprising a nucleic acid, in particular DNA, comprises fragments having a length of 200 to 700 base pairs. Accordingly, it is preferred that sonication is done until most of the nucleic acid fragments are 200-700 base pairs long. It is well-known how to adjust sonication intensity and duration to generate such fragments. Moreover, it is well-known how to determine the length of such fragments to verify sonication setup.

In this regard, the sonication setup may depend on the fixation conditions and cell line/tissue/cell type/organism to obtain the nucleic acid sample. In addition, sonication setup may depend on the used sonication device.

It is also envisaged to use alternative techniques to fragment the nucleic acid sample, in particular the sample comprising DNA. For example, enzymatic digestion can be used for fragmentation of nucleic acids comprised in chromatin. Examplary enzymes are fragmentase (NEB) or MNase (the extracellular nuclease of *Staphylococcus aureus*). Chemical agents or other physical methods besides ultrasound can also be used to fragment nucleic acids comprised in chromatin.

Sonication results may be verified by methods well-known in the art. For example, in order to verify whether most of the nucleic acid, in particular DNA, fragments are 200-700 base pairs long, fragment length may be tested using agarose gel electrophoresis.

In accordance with the above, the methods of the invention comprise as a first step, subsequent to the above described preparatory steps, the addition of an agent binding to chromatin, in particular an antibody or a chemical substance, to a sample comprising a nucleic acid, in particular a DNA. It is preferred that the sample comprising a nucleic acid, in particular a DNA, is derived from a cell, as described above. Subsequent to the addition of the agent binding to chromatin, the chromatin bound by said agent is isolated. In particular, the chromatin bound by said agent is isolated from unbound chromatin. By doing so, the overall amount of chromatin is significantly reduced, which reduces tagmentation events. Isolation of chromatin may be achieved by various techniques described in the art. For example, the agent binding to chromatin, in particular the antibody or chemical substance, can be immobilized on surfaces via affinity interactions. It is preferred that these surfaces are particles (beads). However, other surfaces are also envisaged, for example, columns. Where the agent binding to chromatin is an antibody, the Fc-part of the antibody can bind to the surface of the beads via Protein A, Protein G, Protein L or the like. In this regard, Protein A is a 42 kDa surface protein originally found in the cell wall of the bacterium *Staphylococcus aureus*. It is encoded by the spa gene and its regulation is controlled by DNA topology, cellular osmolarity, and a two-component system called ArlS-ArlR. It is commonly used in biochemical research because of its ability to bind immunoglobulins. Alternatively, antibodies may bind to surfaces via Protein G, which is an immunoglobulin-binding protein expressed in group C and G Streptococcal bacteria much like Protein A but with differing binding specificities. It is a 65-kDa (G148 protein G) and a 58 kDa (C40 protein G) cell surface protein commonly used for purifying antibodies through its binding to the Fab and Fc region. Accordingly, the agent binding to chromatin, wherein the agent is an antibody, can be bound to beads via Protein A, Protein G, Protein L or the like to isolate chromatin bound by said agent, in particular the antibody, from unbound chromatin.

In the methods of the invention, chromatin may also be isolated by other means, for example affinity tags attached to the agent binding to chromatin. For example, an affinity tag can include biotin or His that can bind streptavidin or nickel, respectively. Other examples of multiple-component affinity tag complexes include ligands and their receptors, for example, avidin-biotin, streptavidin-biotin, and derivatives of biotin, streptavidin, or avidin, including, but not limited to, 2-iminobiotin, desthiobiotin, NeutrAvidin, CaptAvidin, and the like; binding proteins/peptides, including maltose-maltose binding protein (MBP), calcium-calcium binding protein/peptide (CBP); antigen-antibody, including epitope tags, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; and the like.

Accordingly, it is preferred that the agent binding to chromatin, wherein the agent binding to chromatin is a chemical substance, is tagged with biotin.

The beads can be magnetic, latex or agarose based material and the like. The immobilized target chromatin can then be isolated by isolation of the beads. This can be achieved by spin centrifugation using filter columns that retain the beads with the agent binding to chromatin on the filter while the non-bound chromatin fraction passes through the filter and can be discarded. In case of magnetic beads, magnetic force is applied to the beads to retain in a reaction vessel while the unbound chromatin fraction can be discarded by pipetting for example. The said agent can also be pre-coupled to surfaces/beads before addition to chromatin. The agent can also be chemically crosslinked to surfaces when precoupled, and does not rely exclusively on affinity interactions to isolate chromatin. As an example Dimethyl pimelimidate (DMP) can be used to couple proteins to beads. Isolation of chromatin is often supported by wash steps to remove unspecific interactions of chromatin with the said agent or unspecific interactions of chromatin with the reaction vessel or surface of the isolating reagent. Washing of chromatin isolated by said agent or chemical substance isolated by above mentioned procedures is achieved by addition and subsequent removal of buffered aqueous solutions containing chemicals including salt and detergents. Accordingly, the methods of the invention may further comprise washing steps subsequent to isolation of chromatin bound by the agent binding to chromatin.

Subsequent to isolation of chromatin bound by the agent binding to chromatin, in particular the antibody or chemical substance, a transposase is added to the isolated chromatin. Transposase is an enzyme that binds to the end of a transposon and catalyzes the movement of the transposon to another part of the genome by a cut and paste mechanism or a replicative transposition mechanism. Transposases are classified under EC number EC 2.7.7. Genes encoding transposases are widespread in the genomes of most organisms and are the most abundant genes known. A preferred transposase within the context of the present invention is Transposase (Tnp) Tn5. Tn5 is a member of the RNase superfamily of proteins which includes retroviral integrases. Tn5 can be found in *Shewanella* and *Escherichia* bacteria. The transposon codes for antibiotic resistance to kanamycin and other aminoglycoside antibiotics. Tn5 and other transposases are notably inactive. Because DNA transposition events are inherently mutagenic, the low activity of transposases is necessary to reduce the risk of causing a fatal mutation in the host, and thus eliminating the transposable element. One of the reasons Tn5 is so unreactive is because the N- and C-termini are located in relatively close proximity to one another and tend to inhibit each other. This was elucidated by the characterization of several mutations which resulted in hyperactive forms of transposases. One such mutation, L372P, is a mutation of amino acid 372 in the Tn5 transposase. This amino acid is generally a leucine residue in the middle of an alpha helix. When this leucine is replaced with a proline residue the alpha helix is broken, introducing a conformational change to the C-Terminal domain, separating it from the N-Terminal domain enough to promote higher activity of the protein. Accordingly, it is preferred that such a modified transposase be used, which has a higher activity than the naturally occurring Tn5 transposase. In addition, it is particularly preferred that the transposase employed in the methods of the invention is loaded with oligonucleotides, which are inserted into the target nucleic acid, in particular the target DNA.

For example, a transposase encoded by the nucleic acid sequence of SEQ ID NOs: 1 or 2 or a nucleic acid sequence having 80, 85, 90, 95, 96, 97, 98 or 99% sequence identity with any of SEQ ID NOs: 1 or 2 may be used in the methods of the invention. In this regard, the transposase may be produced using an expression vector having a nucleic acid sequence as shown in SEQ ID NO:3 or using an expression vector comprising a sequence encoding a transposase corresponding to a transposase encoded by a nucleic acid sequence having 80, 85, 90, 95, 96, 97, 98 or 99% sequence identity with any of SEQ ID NOs: 1 or 2.

Accordingly, it is preferred to use a hyperactive Tn5 transposase and a Tn5-type transposase recognition site (Goryshin and Reznikoff, J. Biol. Chem., 273:7367 (1998)), or MuA transposase and a Mu transposase recognition site comprising RI and R2 end sequences (Mizuuchi, K., Cell, 35: 785, 1983; Savilahti, H, et al, EMBO J., 14: 4893, 1995). More examples of transposition systems that can be used in the methods of the present invention include *Staphylococcus aureus* Tn552 (Colegio et al, J. Bacteriol, 183: 2384-8, 2001; Kirby C et al, Mol. Microbiol, 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol, 204:27-48, 1996), Tn/O and IS 10 (Kleckner N, et al, Curr Top Microbiol Immunol, 204:49-82, 1996), Mariner transposase (Lampe D J, et al, EMBO J., 15: 5470-9, 1996), Tel (Plasterk R H, Curr. Topics Microbiol. Immunol, 204: 125-43, 1996), P Element (Gloor, G B, Methods Mol. Biol, 260: 97-1 14, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al, Proc Natl Acad Sci USA, 86:2525-9, 1989), and retrotransposon of yeast (Boeke & Corces, Annu Rev Microbiol. 43:403-34, 1989). More examples include IS5, TnIO, Tn903, IS91 1, and engineered versions of transposase family enzymes (Zhang et al, (2009) PLoS Genet. 5:e1000689. Epub 2009 Oct. 16; Wilson C. et al (2007) J. Microbiol. Methods 71:332-5) and those described in U.S. Pat. Nos. 5,925,545; 5,965,443; 6,437,109; 6,159,736; 6,406,896; 7,083,980; 7,316,903; 7,608,434; 6,294,385; 7,067,644, 7,527,966; and International Patent Publication No. WO2012103545, all of which are specifically incorporated herein by reference in their entirety.

While any buffer suitable for the used transposase may be used in the methods of the present invention, it is preferred to use a buffer particularly suitable for efficient enzymatic reaction of the used transposase. In this regard, a buffer comprising dimethylformamide is particularly preferred for use in the methods of the present invention, in particular during the transposase reaction. In addition, buffers comprising alternative buffering systems including TAPS, Tris-acetate or similar systems can be used. Moreover, crowding reagents as polyethylenglycol (PEG) are particularly useful to increase tagmentation efficiency of very low amounts of DNA. Particularly useful conditions for the tagmentation reaction are described by Picelli et al. (2014) Genome Res. 24:2033-2040.

The transposase enzyme catalyzes the insertion of a nucleic acid, in particular a DNA in a target nucleic acid, in particular target DNA. The target nucleic acid, in particular target DNA, for insertion is comprised in the isolated chromatin bound by the agent binding to chromatin, in particular the antibody or chemical substance. The transposase used in the methods of the present invention is loaded with oligonucleotides, which are inserted into the target nucleic acid, in particular the target DNA. The complex of transposase and oligonucleotide is also referred- to as transposome. Preferably, the transposome is a heterodimer comprising two different oligonucleotides for integration. In this regard, the oligonucleotides that are loaded onto the transposase comprise multiple sequences. In particular, the oligonucleotides comprise, at least, a first sequence and a second sequence. The first sequence is necessary for loading the oligonucleotide onto the transposase. Exemplary sequences for loading the oligonucleotide onto the transposase are given in US 2010/0120098. The second sequence comprises a linker sequence necessary for primer binding during amplification, in particular during PCR amplification. Accordingly, the oligonucleotide comprising the first and second sequence is inserted in the target nucleic acid, in particular the target DNA, by the transposase enzyme. The oligonucleotide may further comprise sequences comprising barcode sequences. Barcode sequences may be random sequences or defined sequences. In this regard, the term "random sequence" in accordance with the invention is to be understood as a sequence of nucleotides, wherein each position has an independent and equal probability of being any nucleotide. The random nucleotides can be any of the nucleotides, for example G, A, C, T, U, or chemical analogs thereof, in any order, wherein: G is understood to represent guanylic nucleotides, A adenylic nucleotides, T thymidylic nucleotides, C cytidylic nucleotides and U uracylic nucleotides. The skilled person will appreciate that known oligonucleotide synthesis methods may inherently lead to unequal representation of nucleotides G, A, C, T or U. For example, synthesis may lead to an overrepresentation of nucleotides, such as G in randomized DNA sequences. This may lead to a reduced number of unique random sequences as expected based on an equal representation of nucleotides. The oligonucleotide for insertion into the target nucleic acid, in particular DNA, may further comprise sequencing adaptors, for example adaptors suitable for nanopore sequencing or Roche 454 sequencing. Furthermore, the oligonucleotide may comprise biotin tag sequences. It is preferred that the oligonucleotide loaded onto the transposase comprises said first and second sequence and a barcode sequence for indexing. Integration of barcode sequences during the transposase reaction allows the unique identification of each nucleic acid fragment, in particular DNA fragment, during sequencing analysis and/or mapping of molecular interactions.

The person skilled in the art is well-aware that the time required for the used transposase to efficiently integrate a nucleic acid, in particular a DNA, in a target nucleic acid, in particular target DNA, can vary depending on various parameters, like buffer components, temperature and the like. Accordingly, the person skilled in the art is well-aware that various incubation times may be tested/applied before an optimal incubation time is found. Optimal in this regard refers to the optimal time taking into account integration efficiency and/or required time for performing the methods of the invention. While varying incubation times are not necessarily correlated to efficient integration of said nucleic acid, in particular said DNA, in said target nucleic acid, in particular target DNA, it is preferred to use incubation times of less than 10 minutes, less than 5 minutes, preferably, less than 2 minutes. It is most preferred to employ a reaction time of 1 minute for the tagmentation reaction. Furthermore, parameters like temperature and volume may be optimized. In this regard, the recommended incubation temperature for Tn5 transposase is about 37° C. Therefore, it is preferred that the methods of the invention comprise a step of addition of transposase and subsequently incubation for tagmentation at about 37° C., preferably for about 1 min. However, alternative reaction temperatures may also be employed, while it is preferred that temperatures above about 16° C. and below about 55° C. are used in order to maintain sample integrity and transposase efficiency.

Subsequent to addition of transposase to the isolated chromatin, nucleic acids, in particular DNA, are isolated from the sample comprising chromatin, i.e. nucleic acids, in particular DNA, are separated from remaining components of chromatin. This may be achieved by various techniques known in the art. For example, nucleic acids, in particular DNA, can be purified using column-purification, Phenol-chloroform extraction followed by ethanol precipitation, Solid Phase Reversible Immobilisation and Chelex® 100 and other techniques known in the art. Column purification relies on binding of nucleic acids, in particular DNA, (adsorption) to the solid phase (silica or other) depending on the pH and the salt content of the used buffer. After centrifugation of the sample, denaturated proteins remain in the organic phase while the aqueous phase containing nucleic acid, in particular DNA, is mixed with chloroform removing phenol residues from solution. To isolate DNA from the aqueous phase, Phenol-Chlorophorm is followed by ethanol or isopropanol precipitation. Since DNA is insoluble in these alcohols, it will aggregate, giving a pellet upon centrifugation. Precipitation of DNA is improved by increasing ionic strength, usually by adding sodium acetate. Chelex® 100 is a chelating material distributed by Bio-Rad, which is used to purify other compounds via ion exchange. It can also be used to purify DNA. SPRI (Solid Phase Reversible Immobilisation) beads are paramagnetic (magnetic only in a magnetic field). Each bead is made of polystyrene surrounded by a layer of magnetite, which is coated with carboxyl molecules. It is these that reversibly bind DNA in the presence of the "crowding agent" polyethylene glycol (PEG) and salt (commonly 20% PEG, 2.5M NaCl). PEG causes the negatively-charged DNA to bind with the carboxyl groups on the bead surface. As the immobilization is dependent on the concentration of PEG and salt in the reaction, the volumetric ratio of beads to DNA is critical. DNA purification is often supported by removal of RNA and protein by the addition of RNase and Proteinase to the solution.

Subsequent to isolation of the nucleic acids, a sequencing library may be obtained as described above. In particular, a library of nucleic acids, in particular DNA, compatible for sequencing comprises fragments of nucleic acids, in particular DNA, comprising adaptor sequences, which are necessary for sequencing. Accordingly, the methods of the invention for preparing a sequencing library may further comprise an amplification step for integrating said adaptor sequences. Amplification is done as described below. The adaptor sequences vary depending on the sequencing method used subsequent to preparing the sequencing library. For example, where Illumina sequencing is used, i5 and i7 ends may be attached to the nucleic acid fragments. This may also be achieved by the transposase reaction where oligonucleotides loaded onto the transposase enzyme comprise sequencing compatible adaptor sequences.

Where the methods of the invention are for mapping of molecular interactions involving a nucleic acid, the nucleic acid is amplified subsequent to isolation. Amplification may be achieved by various techniques known in the art. The best-known technique for nucleic acid, in particular DNA, amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by techniques such as electrophoresis, restriction endonuclease cleavage patterns, oligonucleotide hybridization or ligation, and/or nucleic acid sequencing.

Primers suitable for use in the methods of the invention comprise sequences hybridisable to the second sequence comprised in the oligonucleotides comprised in the transposomes used in the methods of the invention. In addition, primers may comprise sequences necessary for sequencing. It is preferred that in the methods of the invention specific primers are used that are compatible with the subsequently used sequencing method. In this regard, Illumina sequencing, as one preferred method of sequencing used in the methods of the invention, is compatible with primers introducing flowcell ends, which can hybridize to the flowcell needed in cluster amplification. In this regard, primers may introduce i5 and i7 ends for Illumina sequencing. Furthermore, primers may introduce barcodes for multiplexing. In particular, barcodes comprised in the primer sequences may be used as unique molecular identifiers to discriminate between PCR duplicates and/or as defined barcodes to combine multiple experiments in one sequencing run.

In the methods of the invention for mapping of molecular interactions involving a nucleic acid, in particular DNA, the amplified DNA is sequenced. There are various sequencing methods known in the art. Generally, the sequencing can be performed using pyrosequencing on a solid support (454 sequencing, Roche), sequencing-by-synthesis with reversible terminations (ILLUMINA® Genome Analyzer), or nanopore technology (e.g. Oxford Nanopore Technologies MinION™). In some embodiments the isolated tagmented fragments are analyzed, for example by determining the nucleotide sequence. In some examples, the nucleotide sequence is determined using sequencing or hybridization techniques with or without amplification.

Starting from the sequence information obtained by sequencing the nucleic acid, molecular interactions can be identified using tools known in the art. For example, data may be analyzed using sequence comparison software that aligns sequenced nucleic acids to genomic sequences. Genomic sequences are generally known and obtainable from freely accessible data sources. A match of a sequenced nucleic acid, which is found in the sample to be analyzed, and a genomic sequence may be used as indicator that said sequenced nucleic acid is bound by a macromolecule, for example a histone or transcription factor, which is recognized by the agent binding to chromatin in the methods of the invention.

Where the agent binding to chromatin is a chemical substance, e.g. a drug, the match to a genomic sequence comprised in the nucleic acid fragment to be analyzed indicates binding of the chemical substance, e.g. drug, to a particular nucleic acid region comprised in chromatin.

Based on matching the sequenced nucleic acids to genomic sequences, statistical computational methods can be used to determine regions of significant binding to distinguish them from unspecific "background signal". The identified regions can be used to further infer their biological role by correlating them to other datasets including gene-expression, genome annotation, gene ontology or other systems biology datasets.

By accumulating regions derived from said nucleic acid bound by the agent binding to chromatin, in particular the chemical substance, e.g. a drug, computational methods can also be used to determine significant sequence features of the said regions. Such approaches can be used to find enrichment for specific DNA binding motifs that are known to be bound by a specific transcription factor.

The methods of the invention may also be used to identify regions comprised in the target nucleic acid, in particular DNA, which are inaccessible for the transposase enzyme. In particular, where sequencing libraries are prepared using the methods of the invention, sequencing library fragments may be generated by the introduction of sequencing-compatible oligonucleotides by a transposase in target chromatin. In chromatin comprising nucleic acids and proteins, the proteins comprised in chromatin may to some extent intervene with adapter integration in the target nucleic acid, in particular DNA, at the sites of DNA-protein interactions, without interfering with the preparation of sequencing libraries. The said nucleic acid regions protected from transposase insertion may be identified by computational methods. Such regions are "footprints" of proteins comprised in chromatin, thus revealing high-resolution interactions.

While the methods of the present invention may be carried out in one tube, it is preferred to include tube transfers during the reaction. In particular, the reaction tube may be changed prior to addition of transposase. Additionally or alternatively, the tube may be changed subsequently to addition of transposase after the transposase reaction is finished. The latter decreases tagmentation of unspecific chromatin fragments sticking to tube walls. Accordingly, it is preferred that the methods of the present invention comprise at least one, preferably two, tube transfers, wherein the first tube transfer is carried out subsequent to the transposase reaction prior to isolating nucleic acids from chromatin, or reverse cross-links where the ultra-fast protocol is employed, and wherein the second tube transfer, if a second tube transfer is employed, is carried out prior to addition of transposase.

The present invention also relates to kits, in particular research kits. The kits of the present invention comprise one or more agent(s) binding to chromatin, like one or more chemical substance(s) or one or more antibody/antibodies and transposase. The kits of the invention may comprise a hyperactive, preferably also oligonucleotide loaded, tranposase. In a particular embodiment, the kits of the invention comprise a tranposase encoded by the nucleic acid sequence of SEQ ID NO: 1 or 2 or an expression vector having a nucleic acid sequence of SEQ ID NO: 3. The kits of the invention may also comprise the transposase enzyme in a ready-to-use form. The kits of the invention may be used in diagnosis of medical conditions like diseases. Said medical conditions, like diseases, may be any condition/disease involving the interaction of DNA with further components like for example, but not limited to, transcription factors/histones and the like. For example, diseases known to be related to interaction of DNA with transcription factors/histones include, but are not limited to, proliferative diseases, like for example cancer. Accordingly, the kits of the present invention may be used to diagnose diseases including, but not limited to, T-cell acute lymphoblastic leukemia and the like, acute myeloid leukemia, Ewing sarcoma, acute promyelocytic leukemia, acute lymphoblastic leukemia, diffuse large b cell lymphoma, Transitional cell carcinoma, colorectal cancer, pancreatic cancer, breast cancer, myelodysplastic syndrome, midline carcinoma, papillary thyroid cancer, renal carcinoma, medulloblastoma, multiple myeloma, myelodysplastic syndrome, oesophagila cancer, ovarian cancer, prostate cancer, lung cancer, rhabdoid cancer, hepatocellular carcinoma, familial schwannomatosis, chondrosarcoma, epethioloid sarcoma, meningioma, chordoma, undifferentiated sarcoma, Parkinson's disease, Huntington's diseases, Congenital myotonic dystrophy, Rheumatoid arthritis, systemic lupus erythematodes, Diabetes type 1, Immunodeficiency, Centromere instability and Facial anomalies syndrome and ATRX syndrome among others.

Furthermore, the kits may be used to assess/determine interaction of a chemical compound with DNA. In this regard, the kits of the present invention may be used to assess/determine the likelihood of response of an individual, like a patient, to treatment with a chemical compound interacting with DNA. Treatment may involve treatment of various diseases/conditions using a chemical compound known to be effective, or where the effectiveness is to be tested, wherein the medical condition to be treated may be any disease/condition involving the interaction of DNA. Accordingly, said medical conditions, like diseases, may be any condition/disease involving the interaction of DNA with further components like for example, but not limited to, transcription factors/histones and the like. For example, diseases known to be related to interaction of DNA with transcription factors/histones include, but are not limited to, proliferative diseases, like for example cancer. Accordingly, the kits of the present invention may be used to diagnose diseases including, but not limited to, T-cell acute lymphoblastic leukemia and the like, acute myeloid leukemia, Ewing sarcoma, acute promyelocytic leukemia, acute lymphoblastic leukemia, diffuse large b cell lymphoma, Transitional cell carcinoma, colorectal cancer, pancreatic cancer, breast cancer, myelodysplastic syndrome, midline carcinoma, papillary thyroid cancer, renal carcinoma, medulloblastoma, multiple myeloma, myelodysplastic syndrome, oesophagila cancer, ovarian cancer, prostate cancer, lung cancer, rhabdoid cancer, hepatocellular carcinoma, familial schwannomatosis, chondrosarcoma, epethioloid sarcoma, meningioma, chordoma, undifferentiated sarcoma, Parkinson's disease, Huntington's diseases, Congenital myotonic dystrophy, Rheumatoid arthritis, systemic lupus erythematodes, Diabetes type 1, Immunodeficiency, Centromere instability and Facial anomalies syndrome and ATRX syndrome among others.

In a particularly preferred embodiment of the present invention, the kits (to be prepared in context) of this invention or the methods and uses of the invention may further comprise or be provided with (an) instruction manual(s). For example, said instruction manual(s) may guide the skilled person (how) to employ the kit of the invention in the diagnostic uses provided herein and in accordance with the present invention. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for the uses provided herein, like stabilizing and/or storing the chemical agent(s) and/or transposase comprised in the kits of the present invention.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The methods and techniques of the present invention are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990).

While the invention is illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually, although they may not have been described in the previous or following description. Also, single alternatives of the embodiments described in the figures and the description and single alternatives of features thereof can be disclaimed from the subject matter of the other aspect of the invention.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The present invention is also illustrated by the following figures.

FIG. 1 Overview of prior art methods and their major drawbacks

FIG. 2 Schematic overview of standard ChIP-seq, ChIP-tagmentation, and ChIPmentation Schematic overview of ChIPmentation compared to standard ChIP-seq and library preparation by tagmentation of purified ChIP DNA (ChIP-tagmentation). All three protocols start with fixing cells with formaldehyde, cell lysis, sonication of chromatin, and immunoprecipitation with a specific antibody bound to beads ("chromatin immunoprecipitation"). For standard ChIP-seq (left), reverse-crosslinking is followed by purification of ChIP DNA, which is then subjected to library preparation in a multi-step procedure comprising end repair, purification, A-tailing, adapter ligation, and size selection. ChIP-tagmentation (center) uses purified ChIP DNA for tagmentation-based library preparation, which has the disadvantage that the protocol is sensitive to varying DNA concentrations. In ChIPmentation (right), the sequencing adapters are introduced in a single step during the immunoprecipitation using tagmentation with adapter-loaded Tn5 transposase.

FIG. 3 Supplementary FIG. 3: Effect of Tn5 enzyme concentration on ChIPmentation library size distributions DNA fragment size distribution of ChIPmentation libraries for H3K4me3 that were prepared with different amounts of Tn5 transposase (0.2 µl to 5 µl enzyme from the Illumina Nextera DNA library preparation kit). Fragment sizes after reverse-crosslinking but before library enrichment are shown in red, fragment sizes after enrichment PCR are shown in green, and size-selected final libraries are shown in blue.

Figure 4:
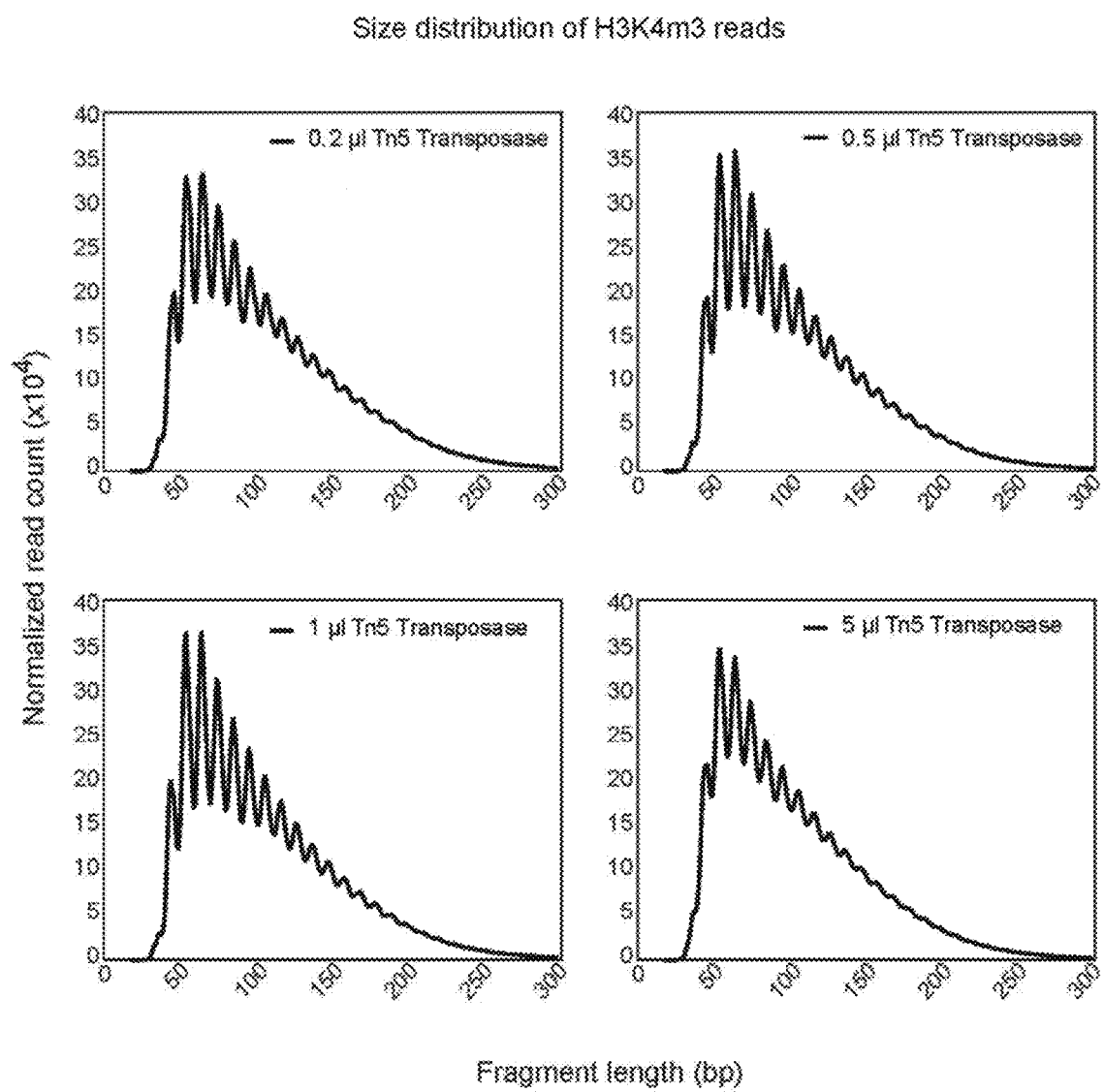
Figure 4:
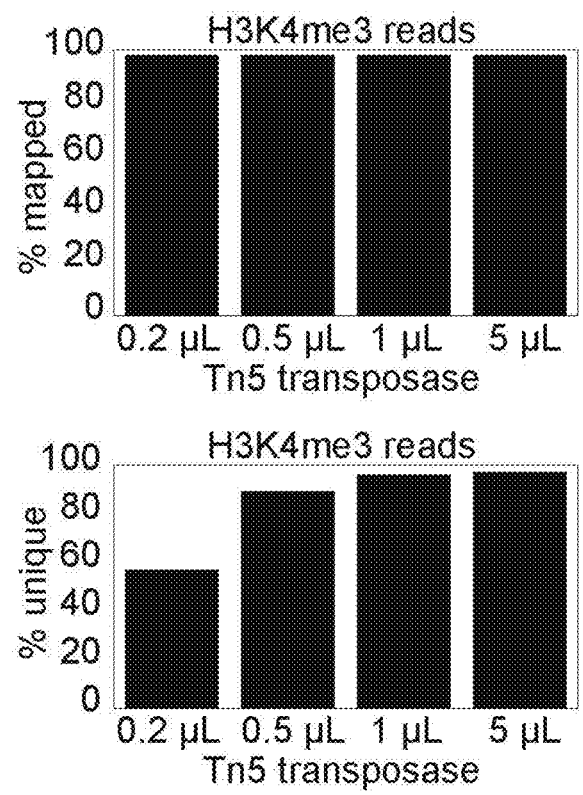
Figure 4:
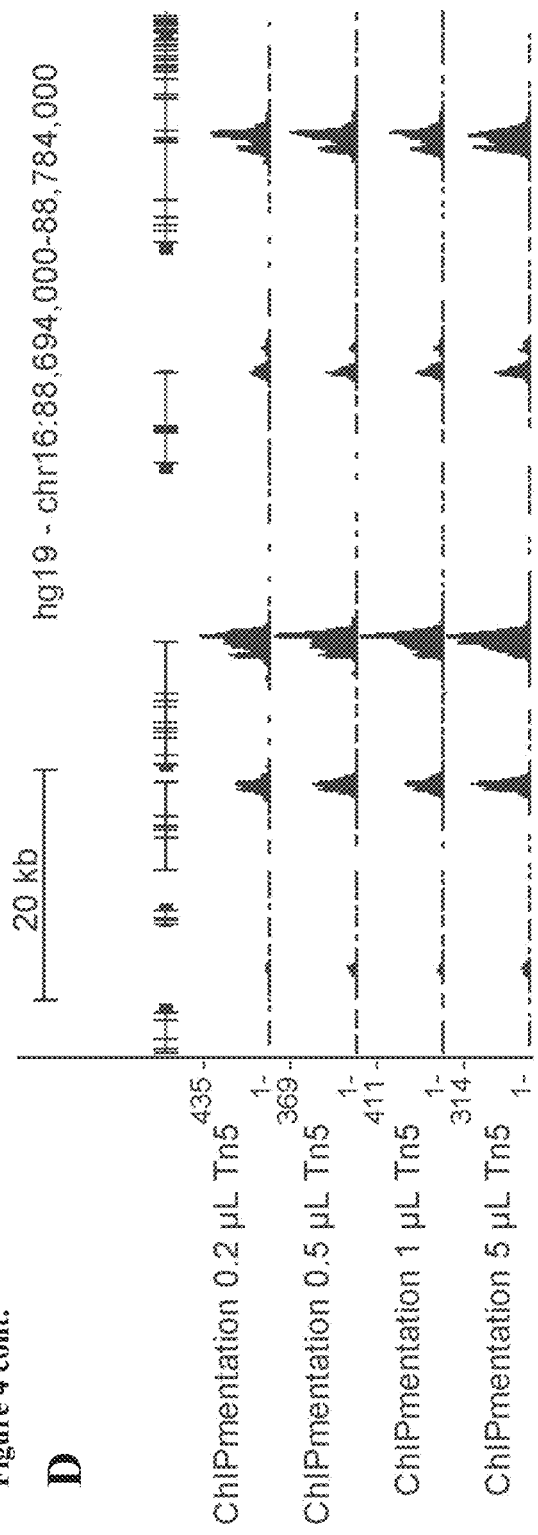
Figure 4:
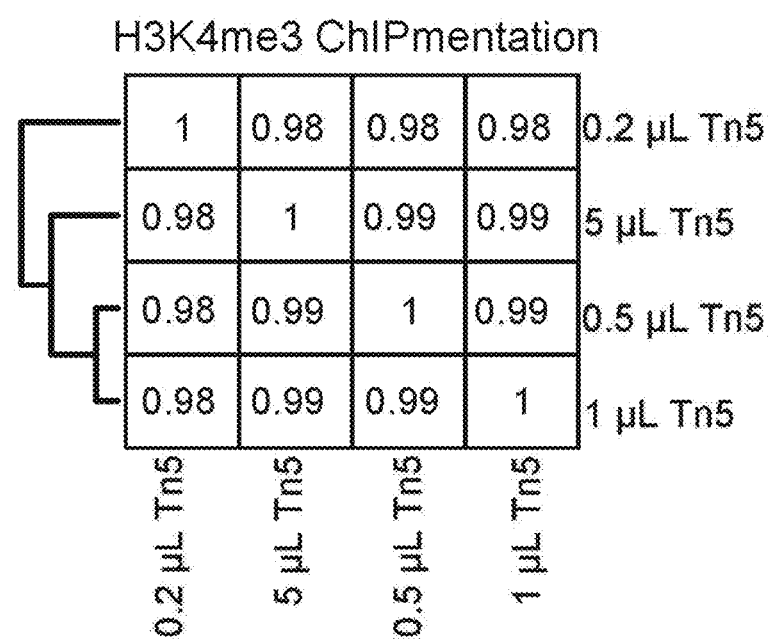
Figure 4:
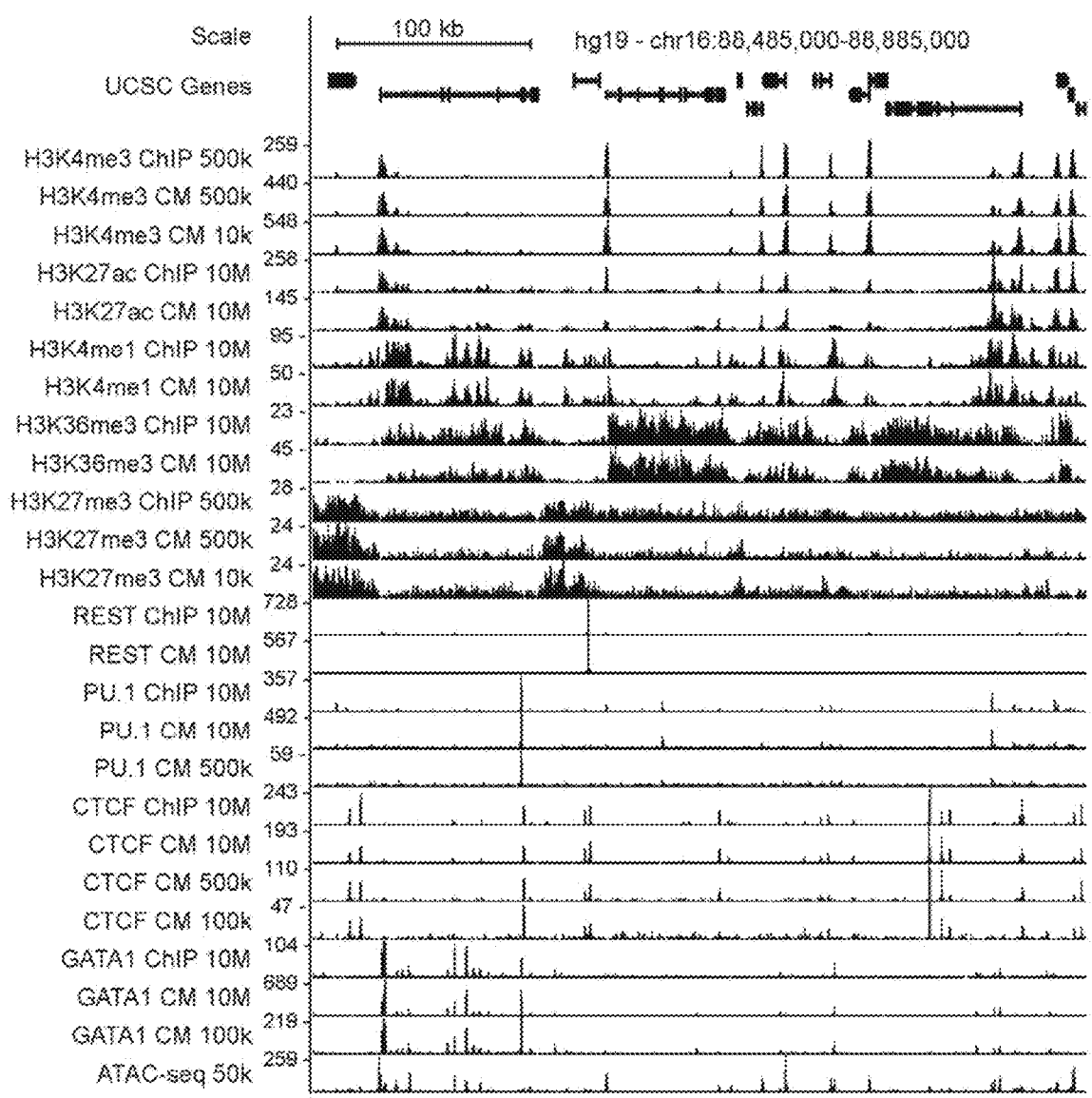
Figure 4:
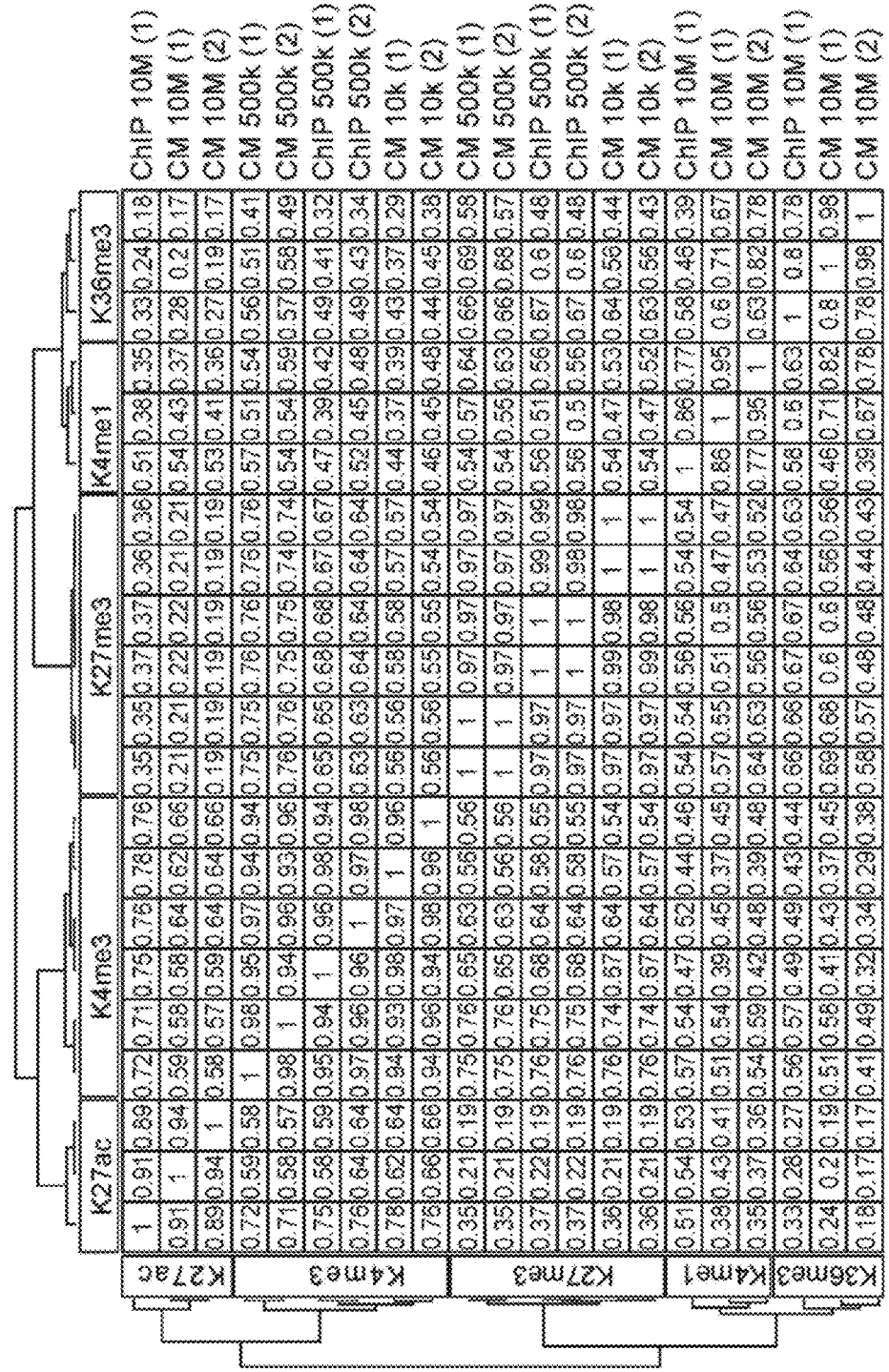
Figure 4:
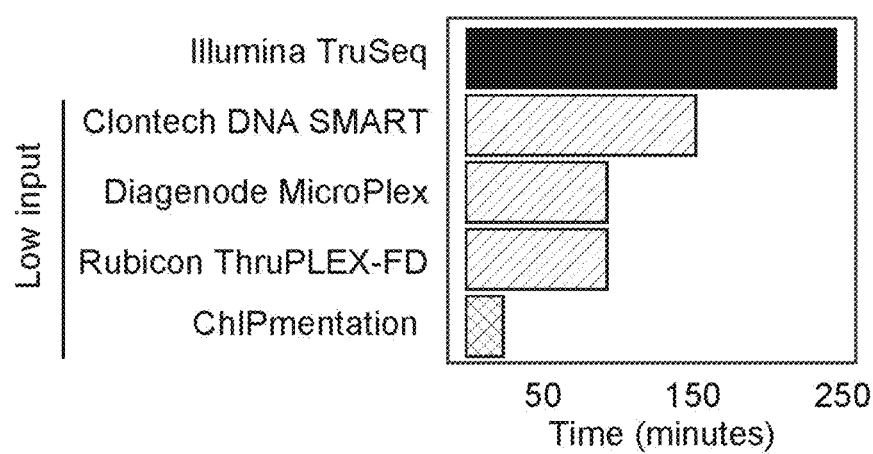

FIG. 4 ChIPmentation: fast, cheap, low-input ChIP-seq for histone marks and transcription factors (a) Schematic overview of ChIPmentation (see FIG. 2 for a comparison of standard ChIP-seq, ChIP-tagmentation starting from purified ChIP DNA, and ChIPmentation).

(b) Size distribution of mapped insert lengths from paired-end sequencing of H3K4me3 ChIPmentation libraries obtained with different Tn5 enzyme concentrations.

(c) Percentages of mapped (top) and unique (bottom) reads for H3K4me3 ChIPmentation libraries obtained with different Tn5 enzyme concentrations.

(d) Genome browser screenshot comparing H3K4me3 ChIPmentation libraries obtained with different Tn5 enzyme concentrations.

(e) Genome-wide correlation heatmap (1,000 bp windows) for H3K4me3 ChIPmentation obtained with different Tn5 enzyme concentrations.

(f) Genome browser screenshot showing ChIP-seq ("ChIP") and ChIPmentation ("CM") data for five histone modifications and four transcription factors from different amounts of input. Data from two biological replicates were combined.

(g) Genome-wide correlation heatmap (1,000 bp windows) for standard ChIP-seq and ChIPmentation data for different histone marks and different cell input amounts.

(h) Genome-wide correlation (1,000 bp windows) of standard ChIP-seq and ChIPmentation data for different transcription factors and different cell input amounts (high: 10M cells; low: 100 k or 500 k cells).

(i) Comparison of hands-on time for standard ChIP-seq (top), commercially available low-input library preparation kits (center), and ChIPmentation (bottom). Hands-on time was calculated from the beginning of the protocol up to (but excluding) the final library amplification PCR reaction.

Figure 5:
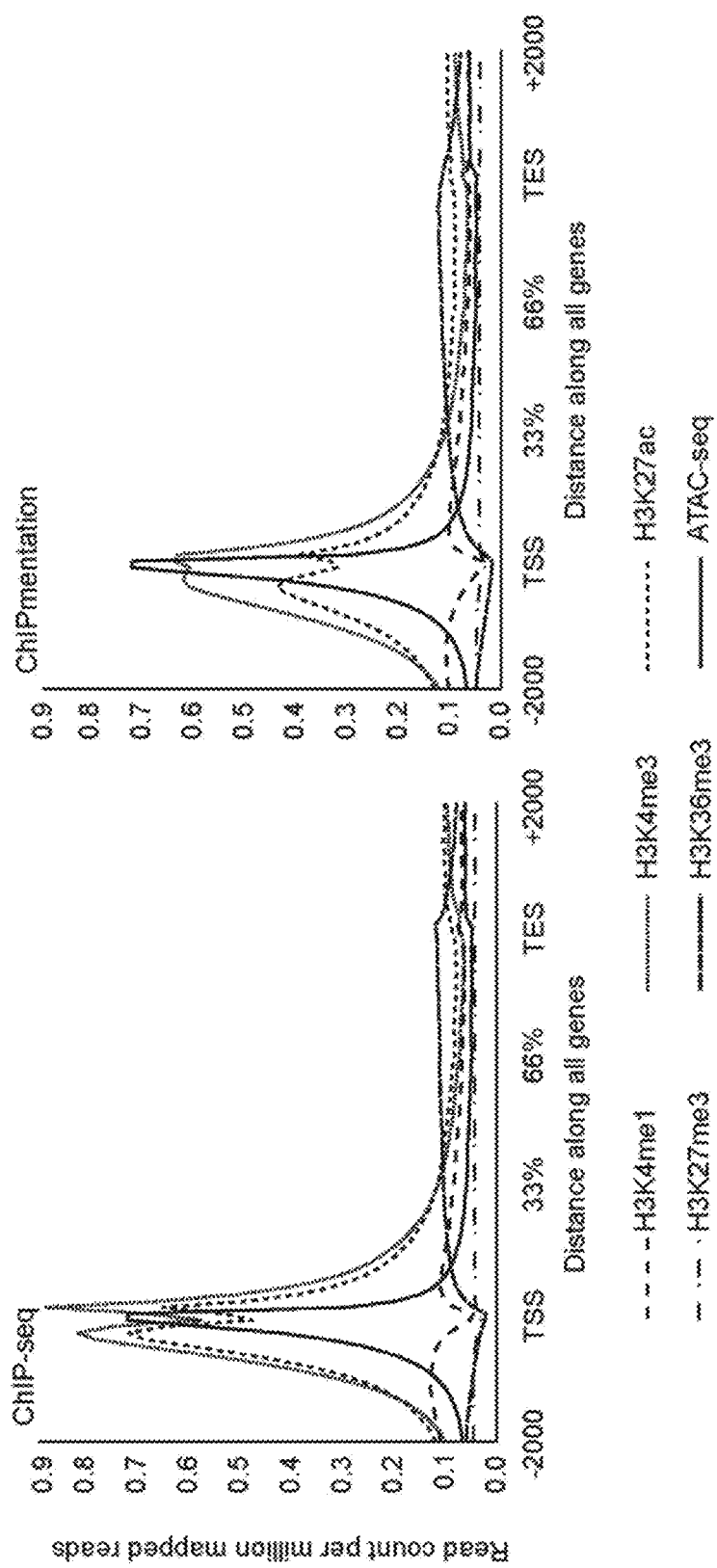
Figure 5:
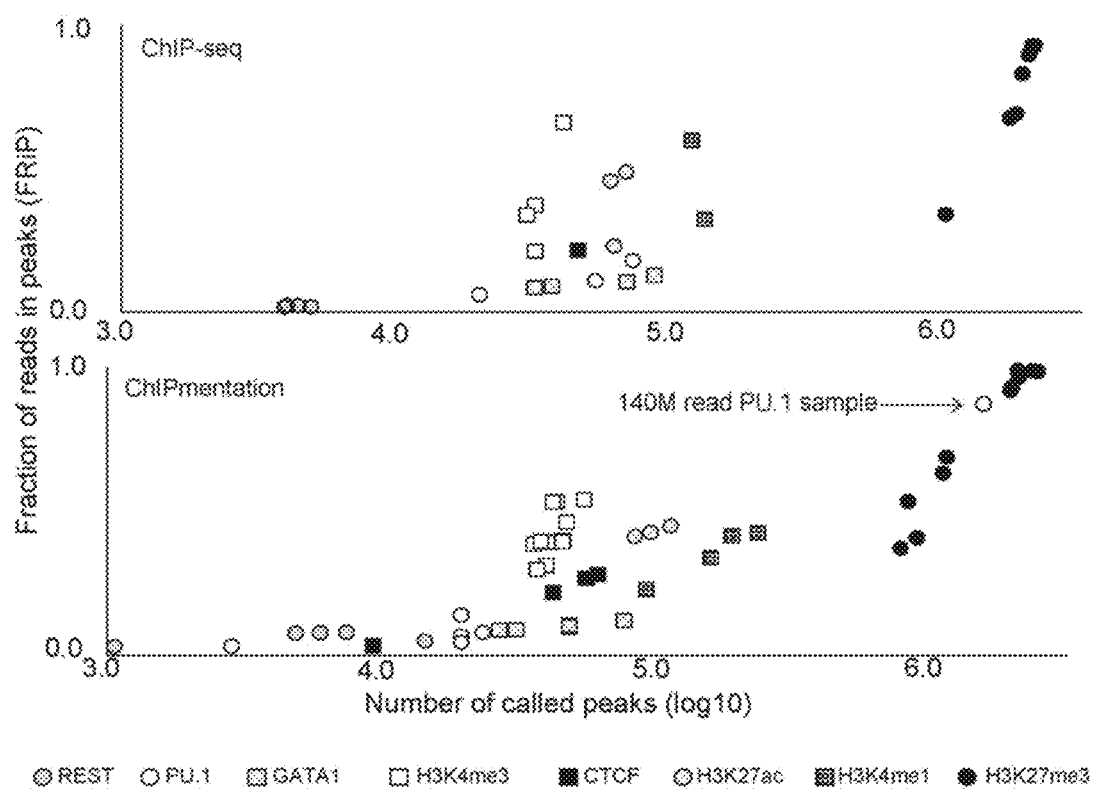

FIG. 5 Global comparison of standard ChIP-seq and ChIPmentation data (a) Composite plot for the distribution of histone marks along all genes, shown separately for ChIPmentation (left) and standard ChIP-seq (right).

(b) Fraction of reads in peaks (FRiP) and number of peaks called from ChIPmentation (upper panel) and ChIP-seq (lower panel) data for all sequenced libraries. Note that the sequencing depth varies between replicates (FIG. 8).

Figure 6:
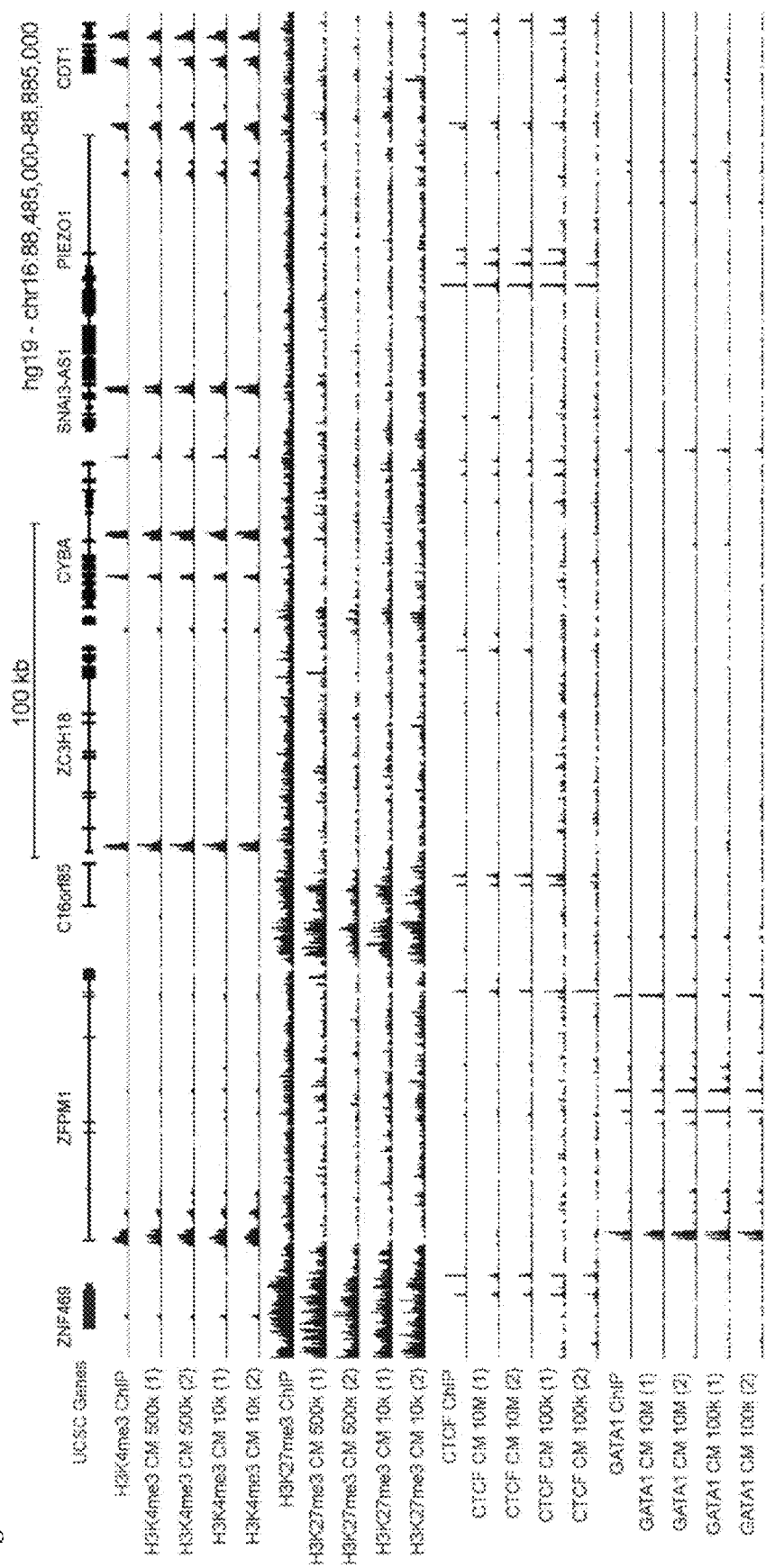

FIG. 6 Genome browser tracks for low-input ChIPmentation data

Genome browser screenshot showing ChIPmentation ("CM") data for individual biological replicates and different cell input amounts (i.e., 10M, 500 k, 100 k, and 10 k cells). Standard ChIP-seq ("ChIP") obtained from 10 million cells data is included as a reference.

Figure 7:
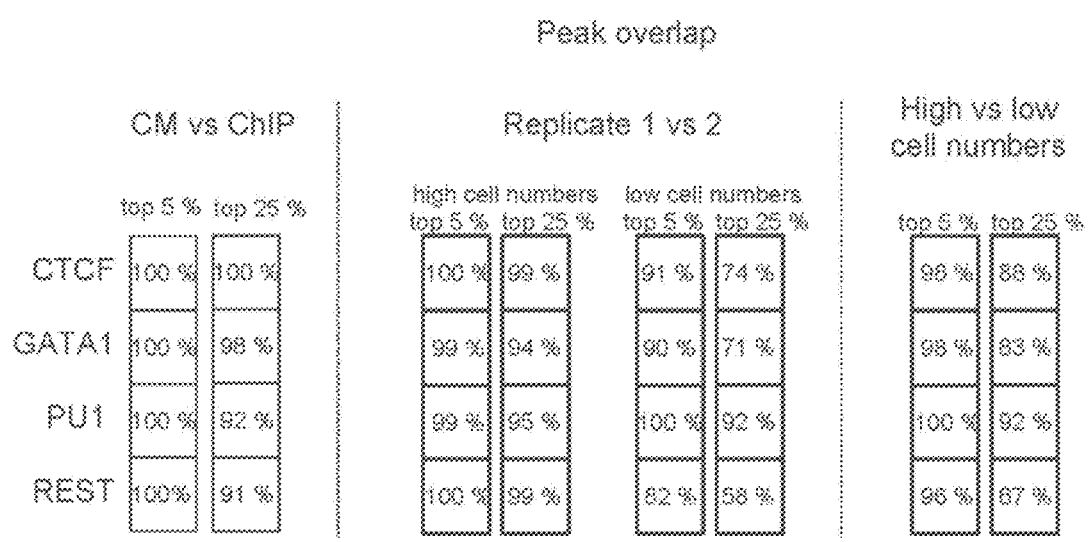

FIG. 7 Peak overlap between standard ChIP-seq and ChIPmentation experiments

Peak overlap calculated as the percentage of top-X % peaks in one replicate/method/input amount that overlap with a significant peak in the other replicate/method/input amount.

FIG. 8 Sequencing summary for 24 standard ChIP-seq libraries, 52 ChIPmentation libraries, and 9 ChIP-tagmentation libraries FIG. 9 High-resolution patterns in ChIPmentation data (a) Signal intensity (Tn5 insertion frequencies) for CTCF, GATA1, PU.1, and REST ChIPmentation data around motifs of the respective transcription factor under called peaks. The upper panels show raw signal of ChIPmentation, ATAC-seq, and DNase-seq, while the lower panels show the background defined by tagmentation of genomic DNA as well as ChIPmentation and ATAC-seq signal intensities normalized to it. Normalization was performed by having signal over e to the Z score of background signal for each peak. For visualization purposes, normalized signal was averaged over all peaks, smoothed with a 20 bp Hanning window and Z score transformed for comparison.

(b) Frequency of pairwise distances between insertion events in ChIPmentation data for H3K4me3. The 10 bp periodic oscillation frequency can be linked to the rotational nature of DNA around nucleosomes[1].

(c) Signal intensity (insertion frequencies) for H3K4me1 ChIPmentation data around nucleosomes positioned using the NucleoATAC software and ATAC-seq data for GM12878 cells. Note the structured pattern with higher and periodical insertions at the nucleosome borders.

Figure 10:
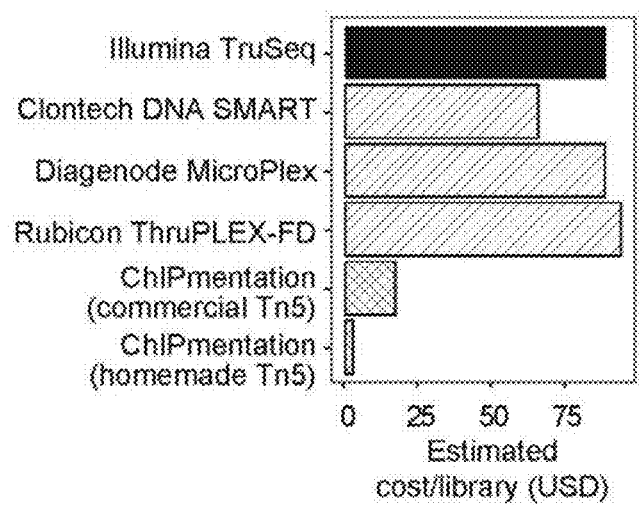

FIG. 10 Comparison of reagent costs for standard ChIP-seq and ChIPmentation

Comparison of reagent costs for standard ChIP-seq (top), commercially available low-input library preparation kits (center), and ChIPmentation (bottom). Cost estimates were calculated for library preparation including amplification and indexing, but excluding reagents for size selection, reaction purifications, and the final quality control step prior to sequencing.

Figure 11:
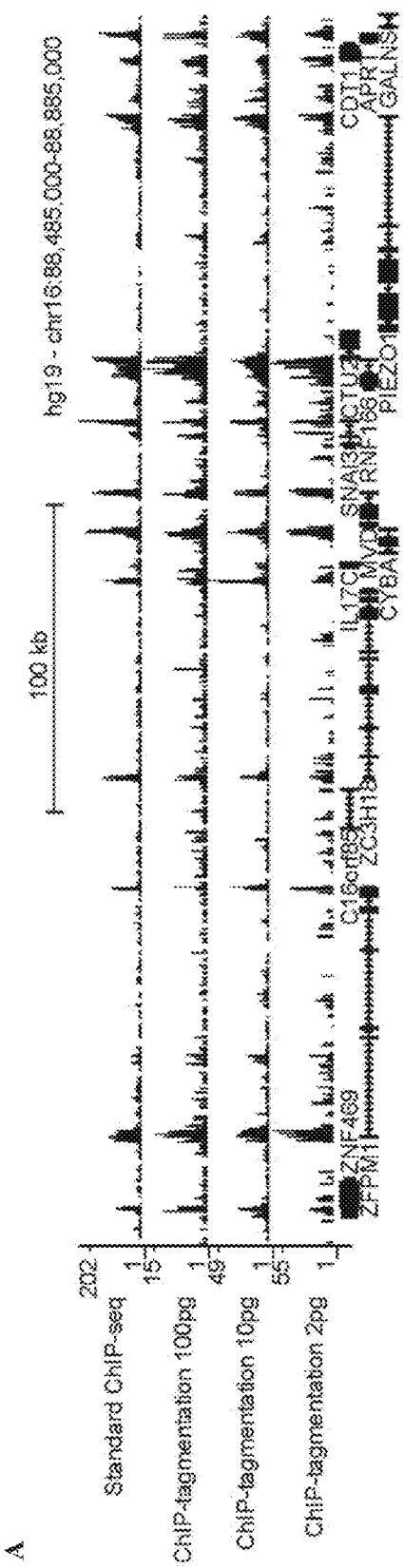
Figure 11:
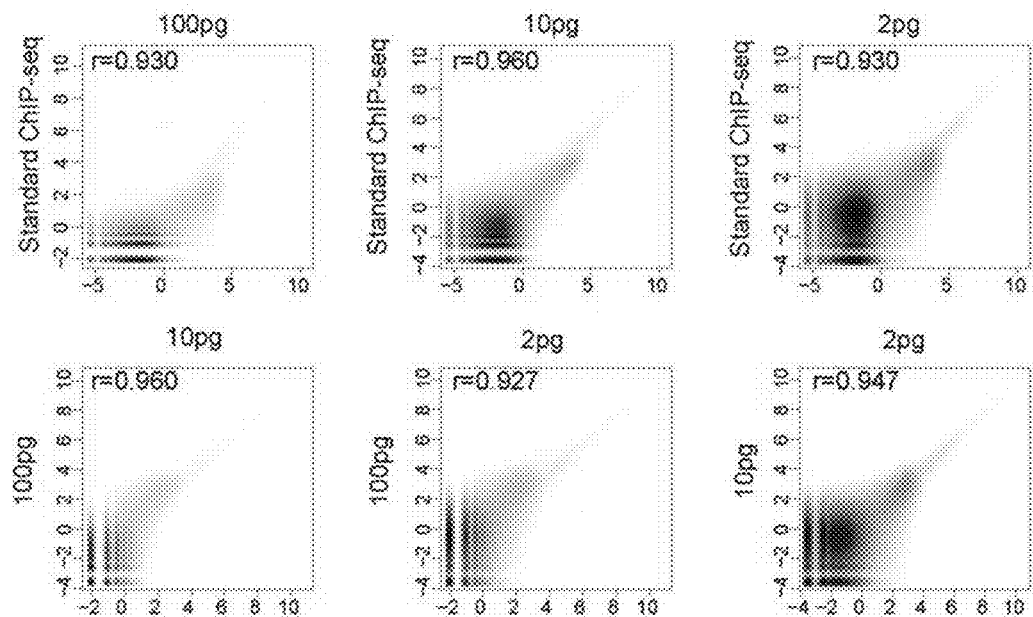

FIG. 11 Library preparation by ChIP-tagmentation starting from purified ChIP DNA (a) Representative UCSC Genome Browser screenshot of ChIP-tagmentation profiles for H3K4me3 in peripheral blood mononuclear cells (PBMCs) using different amounts of purified ChIP DNA as starting material.

(b) Pairwise scatterplots comparing standard ChIP-seq (obtained from 10 million cells) and ChIP-tagmentation for H3K4me3 in peripheral blood mononuclear cells (PBMCs) using different amounts of purified DNA as starting material.

Figure 12:
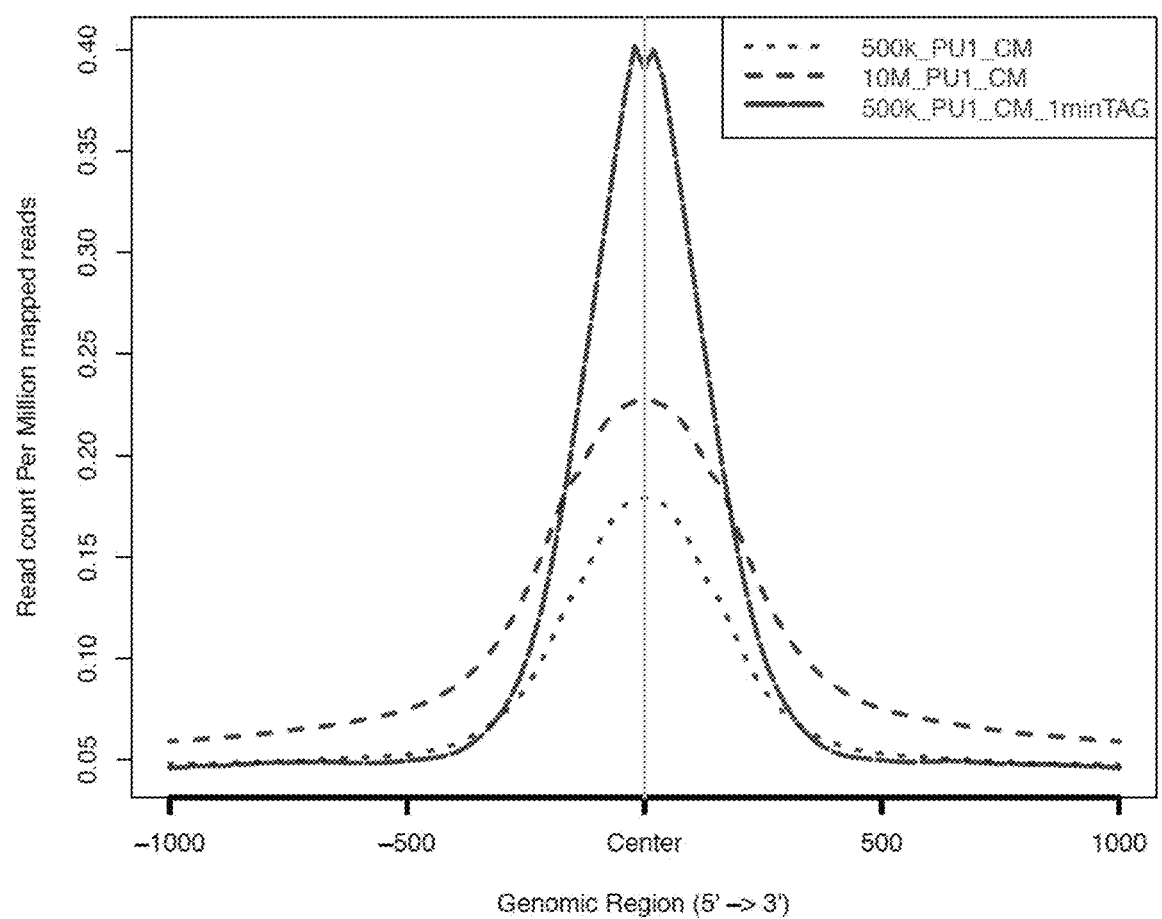

FIG. 12 PU.1 read counts of different experiments at PU.1 binding sites using the methods of the invention. Dashed and dotted lines display data from experiments using 500 k or 10 mio cells, respectively. M-dash line shows the PU.1 signal derived from an experiment using 500 k cells and the exemplary optimized setup described in Example 13. The optimized protocol gives a higher signal-to-noise-ratio than an experiment with 10 mio cells using the standard protocol.

Figure 13:
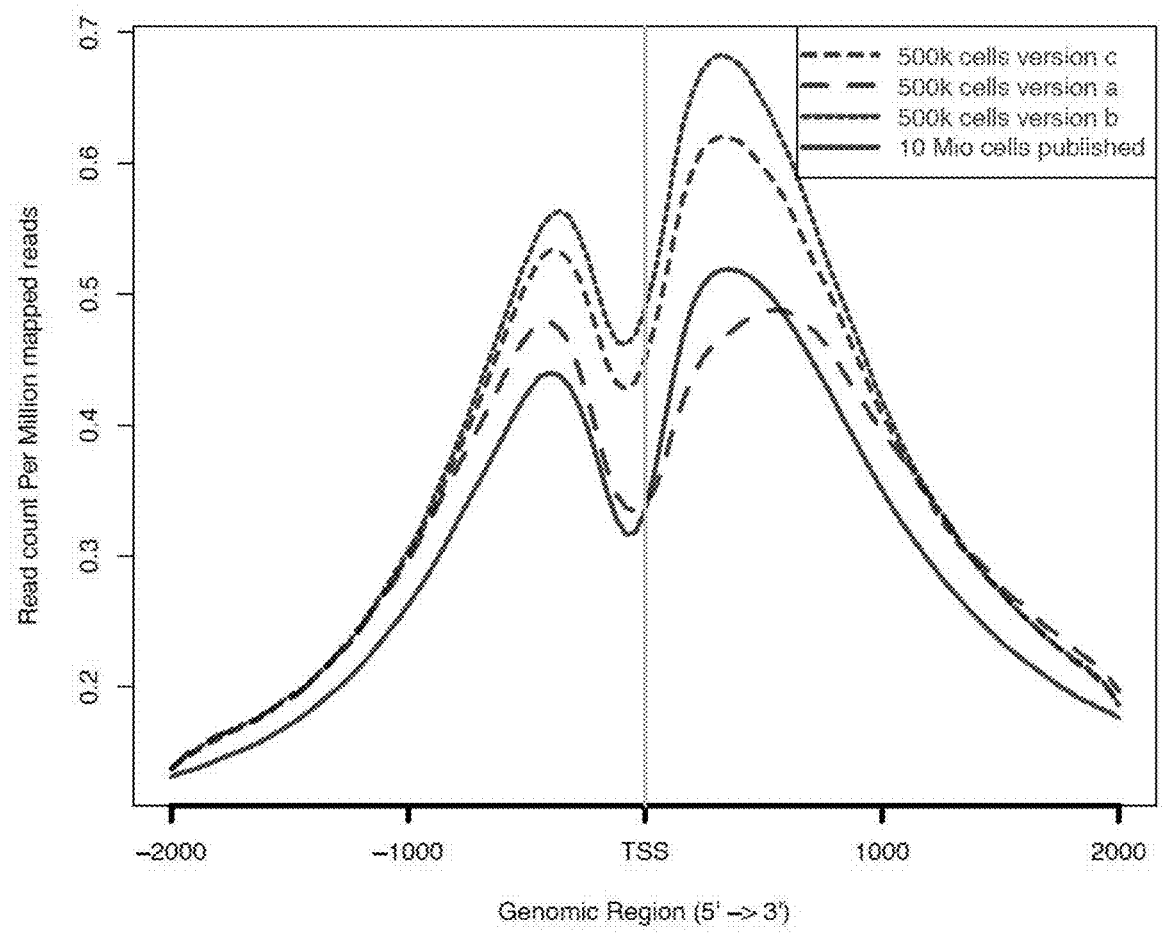

FIG. 13 H3K27ac read counts from different experiments using the methods of the invention in an ultra-fast fashion at annotated transcription start. Dotted and dashed lines correspond to the ultra-fast protocol described in Example 14, while the straight line displays the experiment using the standard protocol. The ultra-fast protocol (which also uses the optimized protocol of Example 13) gives equal or better signal-to-noise-ratios than an experiment with 10 mio cells using the standard protocol.

Figure 14:
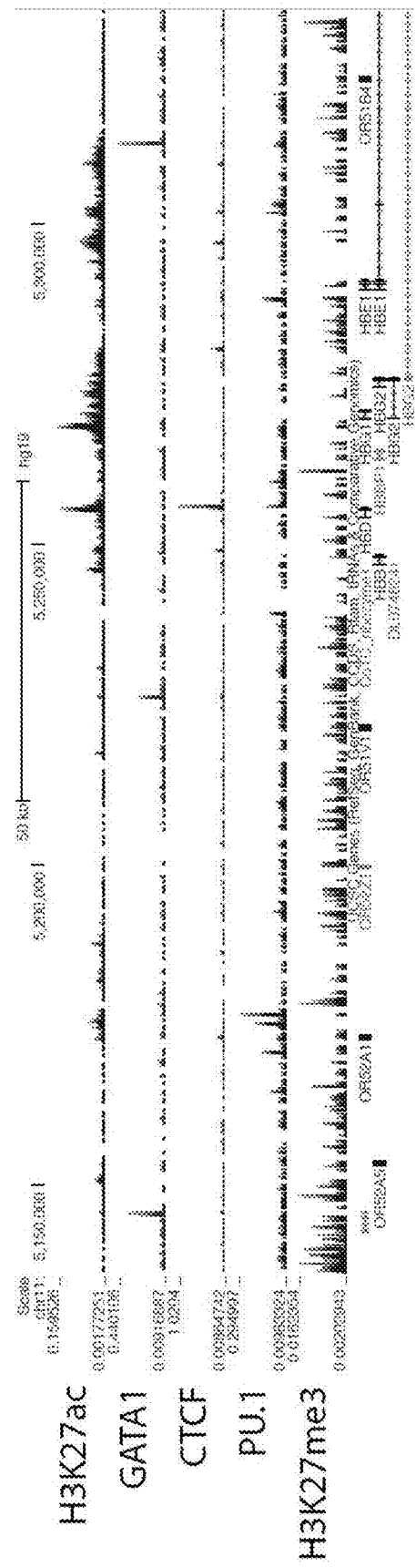

FIG. 14 Generation of sequencing-ready libraries on a single day. Ultra-fast protocol using 500 k K562 cells enabling generation of sequencing-ready libraries for histone marks and transcription factors on a single day. The top track on the right shows dense signals for H3K27ac corresponding to super enhancers at the globin locus in K562 cells.

Figure 15:
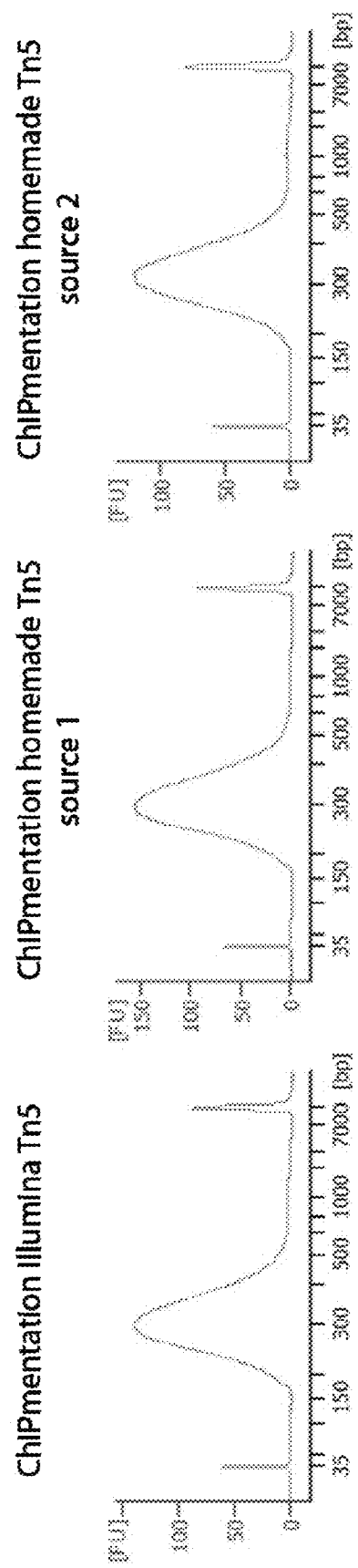

FIG. 15 Comparison of sequencing library preparations obtained using Tn5 transposase and an in-house prepared transposase. Cells of a leukemia cell line were subjected to the methods of the invention using an H3K4me3 antibody and either a commercially available Tn5 transposase or an in-house transpose having a sequence encoded by the nucleic acid sequence as shown in SEQ ID NOs:1 and 2. As can be seen, results do not depend on the transposase used.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should appreciate, in light of the present disclosure, that many changes can be made in the specific embodiments which are disclosed and still obtain a like or similar result without departing from the spirit and scope of the invention.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXAMPLE 1 CHIPMENTATION PROTOCOL

Harvest Cells and Fix

Cells were harvested, washed once with PBS and fixed with 1% paraformaldehyde in up to 1.5 ml PBS for 10 minutes at room temperature. Glycine was added to a final amount of 0.125 M for 5 min at room temperature to stop the reaction. Cells were collected at 500×g for 10 minutes at 4° C. and washed twice with up to 1 ml ice-cold PBS supplemented with 1 µM PMSF.

Lysis and Sonication

The pellet was lysed in RIPA buffer (10 mM Tris-HCl, pH 8.0, 1 mM EDTA, pH 8.0, 140 mM NaCl, 1% Triton x-100, 0.1% SDS, 0.1% DOC, lx protease inhibitors (Sigma)) and sonicated in a 1 ml milliTUBE in a Covaris S220 for 30 minutes until most of the fragments are 200-700 base pairs long (settings: duty cycle 5%, peak incident power 140 Watts, cycles per burst 200 for K562 cells). Lysates were centrifuged at full speed for 5 minutes at 4° C. The supernatant containing the sheared chromatin was then transferred to a 0.5 PCR tube and kept on ice.

Prepare Beads for IP

In parallel to the sonication, 50 µl magnetic protein A/G beads (10 µl for low-input ChIPmentation) were blocked and conjugated to an antibody by washing and resuspending them 2 times in PBS, 0.5% BSA, 0.5% Tween-20. The antibody was added and bound to the beads by rotating>1 h at room temperature (or >2 h at 4° C.).

Immunoprecipitation and Washes

Per ChIP 50 µl of blocked antibody conjugated magnetic protein A beads were added and incubated for 3 hours at 4° C. Immunoprecipitation beads were washed subsequently with cold 150 µl RIPA (twice), RIPA-500 (10 mM Tris-HCl, pH 8.0, 1 mM EDTA, pH 8.0, 500 mM NaCl, 1% Triton x-100, 0.1% SDS, 0.1% DOC,) (twice), and RIPA-LiCl (10 mM Tris-HCl, pH 8.0, 1 mM EDTA, pH 8.0, 250 mM LiCl, 1% Triton X-100, 0.5% DOC, 0.5% NP40 (twice).

Tagmentation—Library Preparation

Beads were washed twice with cold Tris-Cl pH 8.0 to remove detergent, salts, and EDTA. Next, beads were resuspended in 30 µl of the tagmentation reaction mix (10 mM Tris pH 8.0, 5 mM MgCl) containing 1 µl Tagment DNA Enzyme from the Nextera DNA Sample Prep Kit (Illumina) and incubated at 37° C. for 10 minutes in a thermocycler. Beads were then placed on the magnet to remove the tagmentation reaction followed by 2 washes with RIPA.

Complete Washing and Elute DNA, Followed by Reverse Crosslinking

Finally beads were washed twice with TE pH 8.0. To elute complexes the beads were incubated with 70 µl elution buffer (0.5% SDS, 300 mM NaCl, 5 mM EDTA, 10 mM Tris-HCl pH 8.0) containing 2 µl of Proteinase K (NEB) for 1 hour at 55° C. and 8 hours at 65° C. to revert formaldehyde crosslinking, and supernatant was transferred to a new tube.

Purify DNA

Finally, DNA was purified with AMPure XP beads (ratio sample:beads 1:2) or Qiagen MinElute columns.

Amplify Libraries

1 µl of each ChIPmentation reaction was amplified in a 10 µl qPCR reaction containing 0.15 µM primers (see Buenrostro et al. Nature Methods—the original ATAC-seq publication—for primer sequences), 1×SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix was incubated at 98° C. for 45 s prior to preparation of the PCR reaction to activate the hot-start enzyme for successful nick translation in the first PCR step. Final enrichment of the libraries was performed in a 50 µl reaction using 0.75 µM primers and 25 µl KAPA HIF 2× ready mix. Libraries were amplified for N cycles, where N is equal to the rounded-up Cq value determined in the qPCR reaction.

Purification and Size Selection (Optional) of Libraries

Enriched libraries were purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing was performed by the Biomedical Sequencing Facility at CeMM using the Illumina HiSeq 2000/2500 platform.

EXAMPLE 2 CHIP-SEQ, CHIP-TAGMENTATION AND CHIPMENTATION IN COMPARISON

Cell Culture and Sample Collection

K562 cells were cultured in RPMI medium supplemented with 10% FCS and antibiotics. They were analyzed with a CASY cell counter to determine cell numbers. Peripheral blood was obtained from healthy volunteers as approved by the ethics committee at the Medical University of Vienna. Coagulation was prevented with EDTA or heparin, peripheral blood was diluted 1:1-1:3 in PBS, and peripheral blood mononuclear cells (PBMCs) were isolated with Lymphoprep density gradient (Axis-Shield) following manufacturer instructions. Purified cells were suspended in RPMI supplemented with 10% FBS and penicillin-streptomycin.

Chromatin Immunoprecipitation

ChIPmentation was tested in combination with three different protocols for performing the chromatin immunoprecipitation, which are described in detail in Examples 3 to 5.

Standard ChIP-Seq Library Preparation

Purified ChIP DNA was end-repaired using the NEBNext End Repair Module (NEB) according to manufacturer's instruction. Clean-up was done using Ampure XP beads (Agencourt) according to manufacturer's instruction. Fragments were A-tailed using Klenow (3'→5' exo-) polymerase (Enzymatics), and TruSeq-compatible adapters were ligated using T4 DNA Ligase (Enzymatics). The final library was size-selected using Ampure XP beads to remove adapter dimers.

ChIPmentation Library Preparation

ChIPmentation is compatible with various different protocols for ChIP, which makes it easy to apply ChIPmentation to antibodies that work best with different ChIP protocols. In general, the ChIP protocol of choice is carried out until the beads carrying immunoprecipitated chromatin are washed with LiCl-containing wash buffer (WBIII for ChIP as in Example 3, RIPA-LiCl for ChIP as in Example 4, and TF-WBIII for ChIP as in Example 5). Beads are then washed twice with Tris-Cl pH 8.0 to remove detergent, salts and EDTA. Subsequently, beads are resuspended in 20-30 µl of the tagmentation reaction buffer (10 mM Tris pH 8.0, 5 mM MgCl) containing 1 µl Tagment DNA Enzyme from the Nextera DNA Sample Prep Kit (Illumina) and incubated at 37° C. for 10-20 minutes in a thermocycler. Following tagmentation, the beads are washed twice with subsequently 150 µl of WBI (ChIP Example 3), RIPA (ChIP Example 4), or WBI (ChIP Example 5). Afterwards, the corresponding ChIP protocol is continued with the last bead wash, elution from beads, reverse-crosslinking and DNA purification.

Conditions for the tagmentation reaction vary dependent on the agent used for chromatin isolation. Tagmentation conditions vary in temperature (for example 4° C., 16° C., 55° C. and the like), tagmentation time (for example 1, 2, 3, 5, 15, 20, 30, or 60 minutes and the like), Tagment DNA enzyme concentrations (0.001, 0.01, 0.1, 0.2, 0.5, 1.5, 2, 3, 4, 5 or 10 µl and the like) and reaction volume (0.001, 0.01, 0.1, 1, 5, 10, 15, 20, 50, 100 or 200 µl and the like). Moreover, the tagmentation reaction buffer varies and may also comprise additives including detergents, salts, solvents and the like (as an example the tagmentation reaction buffer can contain Dimethylformamid, Polyethylenglycol, Manganese(II) acetate and the like).

ChIP-Tagmentation Library Preparation

Purified ChIP DNA from a standard H3K4me3 ChIP in peripheral blood mononuclear cells (PBMCs) was measured using Qubit fluorometer and then diluted in 10 mM Tris-Cl pH 8.5 supplemented with 0.1% Tween-20 to 100 pg, 10 pg, or 2 pg total DNA. The tagmentation reaction was performed for 5 minutes at 55° C. in a 10 µl reaction containing diluted DNA, 5 µl 2× tagmentation buffer (Illumina) and 1 µl (100 pg DNA) or 0.5 µl (10 pg and 2 pg) 1:10 diluted Nextera Tag DNA Enzyme (diluted in precooled TE/50% Glycerol). The tagmented DNA was amplified with the Nextera DNA Sample Prep Kit (Illumina) according to the manufacturer's instructions with the following program: 72° C. 5 min, 98° C. 30 s, 14 cycles of 98° C. 10 s 63° C. 30 s 72° C. 30 s, and a final elongation at 72° C. for 1 min. Libraries were purified using SPRI AMPure XP beads with a ratio beads:samples of 1.5:1. Purified ChIP DNA or deproteinized input DNA from K562 ChIP was prepared as for PBMCs with slight modifications: 5 ng of ChIP DNA was taken for the tagmentation reaction using 0.5 µl of a 1:10 diluted Tn5 enzyme in a 5 µl reaction at 55° C. for 5 minutes. DNA was purified with the MinElute kit (Qiagen) and amplified with the KAPA HIFI 2× ready mix.

Amplification and Sequencing of Standard ChIP-Seq, ChIP-Tagmentation, and ChIPmentation Libraries 1 µl of each ChIPmentation reaction was amplified in a 10 µl qPCR reaction containing 0.15 µM primers, 1x SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix was incubated at 98° C. for 45 s prior to preparation of the PCR reaction to activate the hot-start enzyme for a successful nick translation in the first PCR step. Final enrichment of the libraries was performed in a 50 µl reaction using 0.75 µM primers and 25 µl KAPA HIF 2× ready mix. Libraries were amplified for N cycles, where N is equal to the rounded-up Cq value determined in the qPCR reaction. Enriched libraries were purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing was performed by the Biomedical Sequencing Facility at CeMM using Illumina HiSeq 2000/2500 platforms (see FIG. 8 for details).

ATAC-Seq

Open chromatin mapping was performed with the assay for transposase accessible chromatin (ATAC-seq) as previously described with minor adaptations for K562 cells. In each experiment, $1 \times 10^5$ cells were washed once in 50 µl PBS, resuspended in 50 µl ATAC-seq lysis buffer (10 mM Tris-HCl, pH 7.4, 10 mM NaCl, 3 mM MgCl2 and 0.01% IGEPAL CA-630), and centrifuged for 10 min at 4° C. Upon centrifugation, the pellet was washed briefly in 50 µl MgCl2 buffer (10 mM Tris pH 8.0, 5 mM MgCl2) before incubating in the transposase reaction mix (12.5 µL 2×TD buffer, 2 µL transposase (Illumina) and 10.5 µL nuclease-free water) for 30 min at 37° C. After DNA purification with the MinElute kit (Qiagen), 1 µl of the eluted DNA was used in a qPCR reaction to estimate the optimum number of amplification cycles. Library amplification was followed by a SPRI size-selection to exclude fragments larger than 1200 bp. DNA concentration was measured with a Qubit fluorometer (Life Technologies).

Sequencing Data Processing and Bioinformatic Analysis

Reads were trimmed using skewer. Trimmed reads were aligned to the hg19/GRCh37 assembly of the human genome using Bowtie2 with the "--very-sensitive" parameter. For ChIPmentation and ATAC-seq data, we adjusted the read start positions to represent the center of the transposition event. Reads aligning to the plus strand were offset by +4 bp, and reads aligning to the minus strand were offset by −5 bp as described previously[2]. We used MACS2 to call peaks on ChIPmentation, ChIP-seq, and ATAC-seq samples. For ChIP and ChIPmentation data, MACS2 was run using a bandwidth of 200 bp, and the matched IgG control as background independently for biological replicates. For broad histone marks (H3K27me3, H3K36me3) the "--broad", "--nomodel", "--extsize 73", and "--pvalue 1e-3" flags and arguments were provided. After ensuring consistency among replicates, downstream analysis was performed on peaks called from merged biological replicates in the same way as described. For correlation analysis of both ChIPmentation and ChIP-seq samples, read counts in 1,000 bp windows genome-wide were calculated and normalized relative to total numbers of non-duplicate reads. Pearson correlation coefficients were computed, and the base-2 logarithm of the signal was plotted for all windows. Comparisons were made between biological replicates, between different techniques (ChIP-seq vs. ChIPmentation), and between different numbers of cells, in the latter two cases based on merged biological replicates. Comparisons between called peaks were done by calculating the fraction of top 5% or 25% peaks that overlap peaks from the other replicate. The same comparison was performed between ChIP-seq and ChIPmentation data, and between ChIPmentation samples produced with different number of cells using samples with both replicates combined.

EXAMPLE 3 EXEMPLARY CHIP PROTOCOL COMPATIBLE WITH CHIPMENTATION

Cells were washed once with PBS and fixed with 1% paraformaldehyde in up to 1 ml PBS for 5 minutes at room temperature. Glycine was added to stop the reaction. Cells were collected at 500×g for 10 minutes at 4° C. (subsequent work was performed on ice and used cool buffers and solutions unless otherwise specified) and washed twice with up to 1 ml ice-cold PBS supplemented with 1 μM PMSF. The pellet was lysed in Cell Lysis Buffer (50 mM HEPES/KOH pH 7.4, 140 mM NaCl, 1 mM EDTA, 0.5 mM EGTA, 10% Glycerol, 0.5% NP-40, 0.25% Triton X-100, 1x protease inhibitors (Sigma)) for 10 minutes on ice. Nuclei were isolated by spinning the lysed cells for 10 minutes at 1,000×g at 4° C., the supernatant was discarded, and the pellet was resuspended in Sonication Buffer (10 mM Tris-HCl pH 7.6, 1 mM EDTA, 0.1% SDS) and sonicated in a 130 μl microTUBE (for up to 3×10[6] cells) on a Covaris S220 for 12 minutes until most of the fragments were 200-700 base pairs long (settings: duty cycle 2%, peak incident power 105 Watts, cycles per burst 200). Lysates were centrifuged at full speed for 5 minutes at 4° C. and the supernatant was transferred to a new tube. The lysate was adjusted to 200 μl per IP with a buffer composition of 20 mM HEPES, 0.1% SDS, 1% Triton X-100, 150 mM NaCl, 1 mM EDTA, 0.5 mM EGTA and incubated with an antibody against H3K4me3 (1 μg/IP, Diagenode pAb-003-050) or H3K27me3 (1 μg/IP, Diagenode pAb-195-050) overnight at 4° C. on a rotator. 20 μl of Protein A (or Protein G, dependent on the antibody used) magnetic beads were blocked overnight with 0.1% BSA in PBS and added to the IP the next day for 2 hours on a rotator at 4° C. to capture the immunoprecipitated fragments. The immunoprecipitated chromatin was washed subsequently with WBI (20 mM HEPES, 150 mM NaCl, 0.1% SDS, 0.1% DOC, 1% Triton X-100, 1 mM EDTA, 0.5 mM EGTA) (twice), WBII (20 mM HEPES, 500 mM NaCl, 0.1% SDS, 0.1% DOC, 1% Triton X-100, 1 mM EDTA, 0.5 mM EGTA) (once), WBIII (20 mM HEPES, 250 mM LiCl, 0.5% DOC, 0.5% NP-40, 1 mM EDTA, 0.5 mM EGTA) (once), and WBIV (20 mM HEPES, 1 mM EDTA, 0.5 mM EGTA) (twice). Beads were then incubated with 70 μl elution buffer (0.5% SDS, 300 mM NaCl, 5 mM EDTA, 10 mM Tris-HCl pH 8.0) containing 2 μl of Proteinase K (NEB) for 1 hour at 55° C. and 8 hours at 65° C. to revert formaldehyde crosslinking, and supernatant was transferred to a new tube. Another 30 μl of elution buffer was added to the beads for 1 minute, and eluates were combined and incubated with another 1 μl of Proteinase K for 1 hour at 55° C. Finally, DNA was purified with SPRI AMPure XP beads (sample-to-beads ratio 1:2) or Qiagen MinElute columns.

EXAMPLE 4 EXEMPLARY CHIP PROTOCOL COMPATIBLE WITH CHIPMENTATION

Cells were washed once with PBS and fixed with 1% paraformaldehyde in up to 1.5 ml PBS for 10 minutes at room temperature. Glycine was added to stop the reaction. Cells were collected at 500×g for 10 minutes at 4° C. (subsequent work was performed on ice and used cool buffers and solutions unless otherwise specified) and washed twice with up to 1 ml ice-cold PBS supplemented with 1 μM PMSF. The pellet was lysed in RIPA buffer (10 mM Tris-HCl, pH 8.0, 1 mM EDTA, pH 8.0, 140 mM NaCl, 1% Triton x-100, 0.1% SDS, 0.1% DOC, 1x protease inhibitors (Sigma)) and sonicated in a 1 ml milliTUBE in a Covaris S220 for 30 minutes until most of the fragments were 200-700 base pairs long (settings: duty cycle 5%, peak incident power 140 Watts, cycles per burst 200). Lysates were centrifuged at full speed for 5 minutes at 4° C., and the supernatant containing the sonicated chromatin was transferred to a new tube. In parallel, 50 μl (10 μl for low-input ChIPmentation) magnetic Protein A or Protein G beads (dependent on the antibody used) were blocked and conjugated to an antibody by washing and resuspending twice in PBS, 0.5% BSA, 0.5% Tween-20. The antibody was added and bound to the beads by rotating>1 hour at room temperature. Used antibodies were H3K4me1 (1 μg/IP, Diagenode pAb-194-050), H3K36me3 (1 μg/IP, Diagenode pAb-192-050), and REST (10 μg/IP, Millipore 07-579). Blocked antibody-conjugated beads were then placed on a magnet, supernatant was removed, and the sonicated lysate was added to the beads followed by incubation for 3 hours at 4° C. on a rotator. Beads were washed subsequently with 150 μl RIPA (twice), RIPA-500 (10 mM Tris-HCl, pH 8.0, 1 mM EDTA, pH 8.0, 500 mM NaCl, 1% Triton x-100, 0.1% SDS, 0.1% DOC,) (twice), RIPA-LiCl (10 mM Tris-HCl, pH 8.0, 1 mM EDTA, pH 8.0, 250 mM LiCl, 1% Triton X-100, 0.5% DOC, 0.5% NP40), and TE pH 8.0 (twice). Beads were then incubated with 70 μl elution buffer (0.5% SDS, 300 mM NaCl, 5 mM EDTA, 10 mM Tris-HCl pH 8.0) containing 2 μl of Proteinase K (NEB) for 1 hour at 55° C. and 8 hours at 65° C. to revert formaldehyde crosslinking, and supernatant was transferred to a new tube. Finally, DNA was purified with SPRI AMPure XP beads (sample-to-beads ratio 1:2) or Qiagen MinElute columns.

EXAMPLE 5 EXEMPLARY CHIP PROTOCOL COMPATIBLE WITH CHIPMENTATION

Cells were washed once with PBS and fixed with 1% paraformaldehyde in up to 1.5 ml PBS for 5-10 minutes at room temperature. Glycine was added to stop the reaction. Cells were collected at 500×g for 10 minutes at 4° C. (subsequent work was performed on ice and used cool buffers and solutions unless otherwise specified) and washed twice with up to 1 ml ice-cold PBS supplemented with 1 µM PMSF. The pellet was lysed in buffer L3B (10 mM Tris-HCl, pH 8.0, 100 mM NaCl, 1 mM EDTA, 0.5 mM EGTA, 0.1% Na-Deoxycholate, 0.5% N-lauroylsarcosine, lx protease inhibitors (Sigma)) and sonicated in a 1 ml milliTUBE in a Covaris S220 for 20 minutes until most of the fragments were 200-700 base pairs long (settings: duty cycle 5%, peak incident power 140 Watts, cycles per burst 200). Lysates were supplemented with 1% Triton-X-100 and centrifuged at full speed for 5 minutes at 4° C., and the supernatant containing the sonicated chromatin was transferred to a new tube. In parallel, beads were blocked and conjugated to an antibody by washing them twice in PBS with 0.5% BSA and resuspending 50 µl (10 µl beads for low-input ChIPmentation) of magnetic Protein A or Protein G beads (dependent on the antibody used) per IP in 200 µl of PBS with 0.5% BSA. The antibody was added and bound to the beads by rotating>1 hour at room temperature or 2 hr at 4° C. in a rotator. Used antibodies were H3K27ac (2 pg, Diagenode pAb-196-050), PU.1 (5 pg/IP, Santa Cruz sc-352), CTCF (10 µl/IP, Millipore 07-729), and GATA1 (4 µg/IP and 2 pg for low-input, Abcam ab11852). Blocked antibody conjugated magnetic beads were added to the tube containing the chromatin and incubated for 3 hours at 4° C. Beads were washed subsequently with 150 µl TF-WBI (20 mM Tris-HClI/pH 7.4, 150 mM NaCl, 0.1% SDS, 1% Triton X-100, 2 mM EDTA) (twice), TF-WBIII (250 mM LiCl, 1% Triton X-100, 0.7% DOC, 10 mM Tris-HCl, 1 mM EDTA) (twice), and TET (0.2% Tween-20, 10 mM Tris-HClI/pH 8.0, 1 mM EDTA) (twice). Beads were then incubated with 70 µl elution buffer (0.5% SDS, 300 mM NaCl, 5 mM EDTA, 10 mM Tris HCl pH 8.0) containing 2 µl of Proteinase K (NEB) for 1 hour at 55° C. and 8 hours at 65° C. to revert formaldehyde crosslinking, and supernatant was transferred to a new tube. Another 30 µl of elution buffer was added to the beads for 1 minute and eluates were combined and incubated with another 1 µl of Proteinase K for 1 hour at 55° C. Finally, DNA was purified with SPRI AMPure XP beads (sample-to-beads ratio 1:2) or Qiagen MinElute columns.

EXAMPLE 6—EXEMPLARY SONICATION SETUPS

For K562 leukemic cell line, a 10 minute fixation at room temperature with 1% formaldehyde was performed. The chromatin in sonication buffer (10 mM Tris-HCl pH 7.6, 1 mM EDTA, 0.1% SDS) was sonicated in a 130 µl Covaris microTUBE (for up to 3×106 cells) on a Covaris S220 (or similar versions) for 10-15 minutes with the settings: duty cycle 2%, peak incident power 105 Watts, cycles per burst 200, recommended water temperature maximum 8° C., degasing pump switched on. As a second example, the chromatin can be in RIPA buffer (10 mM Tris-HCl, pH 8.0, 1 mM EDTA, pH 8.0, 140 mM NaCl, 1% Triton x-100, 0.1% SDS, 0.1% DOC, lx protease inhibitors (Sigma)) and be sonicated in a 1 ml Covaris milliTUBE in a Covaris S220 (or similar versions of the machine) for 25-30 minutes with the settings: duty cycle 5%, peak incident power 140 Watts, cycles per burst 200, recommended water temperature maximum 8° C., degasing pump switched on.

Other sonication devices can be used, as an example the Bioruptor (Diagenode): As an exemplary sonication setting suitable for several cell lines, chromatin can be sonicated in lysis buffer (10 mM Tris-HCl, pH 8.0, 100 mM NaCl, 1 mM EDTA, 0.5 mM EGTA, 0.1% Na-Deoxycholate, 0.5% N-lauroylsarcosine, lx protease inhibitors (Sigma P8340)) with the settings "High" in either Eppies (50 µl-200 µl) 2×15 minutes, sonication cycles: 30 seconds ON/30 seconds OFF or in 15 ml conicals (500 µl-1.5 ml) with resonators for 15 minutes, sonication cycles: 30 seconds ON/30 seconds OFF.

A further device used for sonication is a probe sonicator. As an example, chromatin in lysis buffer (10 mM Tris-HCl, pH 8.0, 100 mM NaCl, 1 mM EDTA, 0.5 mM EGTA, 0.1% Na-Deoxycholate, 0.5% N-lauroylsarcosine, lx protease inhibitors (Sigma P8340)) can be sonicated on ice 6 times 10 seconds at 12 W output with recommended 30 s pause between sonication cycles to prevent overheating of chromatin using a Branson Sonifier 450 with a microtip probe.

EXAMPLE 7—ANALYSIS OF PRIMARY TUMORS

Frozen tumor pieces are sliced to 50 µm slices using a microtome and transferred to a reaction tube on ice (20-50 slices are sufficient for multiple histone ChIPmentation reactions depending on the size of the tumor). The slices are washed once with PBS and fixed using 1% paraformaldehyde in up to 1.5 ml PBS for 10 minutes at room temperature. Glycine is added to stop the reaction. Cells are collected at 500×g for 10 minutes at 4° C. (subsequent work is performed on ice and buffers and solutions are cooled unless otherwise specified) and are washed twice with up to 1 ml ice-cold PBS supplemented with 1 µM PMSF. The pellet is lysed in buffer L3B (10 mM Tris-HCl, pH 8.0, 100 mM NaCl, 1 mM EDTA, 0.5 mM EGTA, 0.1% Na-Deoxycholate, 0.5% N-lauroylsarcosine, lx protease inhibitors (Sigma)) and sonicated in a 1 ml milliTUBE in a Covaris S220 for 35 minutes until most of the fragments are 200-700 base pairs long (settings: duty cycle 5%, peak incident power 140 Watts, cycles per burst 200). Lysates are supplemented with 1% Triton-X-100 and centrifuged at full speed for 5 minutes at 4° C., and the supernatant containing the sonicated chromatin is transferred to a new tube. In parallel, beads are blocked and conjugated to an antibody by washing them twice in PBS with 0.5% BSA and resuspending 50 µl (10 µl beads for low-input ChIPmentation) of magnetic Protein A or Protein G beads (dependent on the antibody used) per IP in 200 µl of PBS with 0.5% BSA. The antibody is added and bound to the beads by rotating>1 hour at room temperature. Examples for antibodies are H3K27ac (2 pg, Diagenode pAb-196-050), PU.1 (5 µg/IP, Santa Cruz sc-352), CTCF (10 µl/IP, Millipore 07-729), and GATA1 (4 µg/IP and 2 pg for low-input, Abcam ab11852). Blocked antibody conjugated magnetic beads are added to the tube containing the chromatin and incubated for 3 hours at 4° C. Beads are washed subsequently with 150 µl TF-WBI (20 mM Tris-HCl/pH 7.4, 150 mM NaCl, 0.1% SDS, 1% Triton X-100, 2 mM EDTA) (twice) and TF-WBIII (250 mM LiCl, 1% Triton X-100, 0.7% DOC, 10 mM Tris-HCl, 1 mM EDTA) (twice). Beads are washed twice with cold Tris-CI pH 8.0 to remove detergent, salts, and EDTA. Beads are resuspended carefully in 30 µl of the tagmentation reaction mix (10 mM Tris pH 8.0, 5 mM MgCl) containing 1 µl Tagment DNA Enzyme from the Nextera DNA Sample Prep Kit (Illumina) and incubated at 37° C. for 10 minutes in a thermocycler. The tagmentation reaction is removed by placing the reaction on a magnet and removing the supernatant, and beads are washed twice with TF-WBI. Beads are washed with TET (0.2% Tween-20, 10 mM Tris-HCl/pH 8.0, 1 mM EDTA) (twice). Beads are then incubated with 70 µl elution buffer (0.5% SDS, 300 mM NaCl, 5 mM EDTA, 10 mM Tris HCl pH 8.0) containing 2 µl of Proteinase K (NEB) for 1 hour at 55° C. and 8 hours at 65° C. to revert formaldehyde crosslinking, and supernatant is transferred to a new tube. Another 30 µl of elution buffer is added to the beads for 1 minute and eluates are combined and incubated with another 1 µl of Proteinase K for 1 hour at 55° C. Finally, DNA is purified with SPRI AMPure XP beads (sample-to-beads ratio 1:2) or Qiagen MinElute columns, eluting in 11 µl H2O. 1 µl of each ChIPmentation reaction is amplified in a 10 µl qPCR reaction containing 0.15 µM primers, lx SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix is preincubated at 98° C. for 45 s prior to preparation of the PCR reaction to activate the hot-start enzyme for a successful nick translation in the first PCR step. Final enrichment of the libraries (using the remaining 10 µl from the ChIP) is performed in a 50 µl reaction using 0.75 µM primers and 25 µl KAPA HIF 2× ready mix. Libraries are amplified for N cycles, where N is equal to the rounded-up Cq value determined in the qPCR reaction. Enriched libraries are purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing is performed using Illumina HiSeq 2000/2500 platforms.

EXAMPLE 8—CHIPMENTATION ON FORMALIN-FIXED, PARAFFIN-EMBEDDED SAMPLES (FFPE SAMPLES) FROM CLINICAL SPECIMEN OR OTHER SOURCES

Samples are formalin fixed and paraffin embedded with methods known in the art. For using the invention on FFPE samples deparaffination of tissue sample sections is carried out through sequential incubations (10 min each) in 1 mL of hystolemon solution (six to eight times) at room temperature. Then samples are rehydrated by decreasing concentrations of ethanol starting from 100% (absolute ethanol) through to 95%, 70%, 50%, and 20%, with water as the final step (5 min at room temperature for each step of rehydration). Rehydrated FFPE sections are incubated in 0.5 mL permeabilization buffer [1× Tris-buffered saline (TBS), 0.5% Tween20, 1 mM PMSF, and 10 µg/mL RNase A] for 30 min at room temperature in a rotating platform. After centrifugation at 18,000×g for 5 min at +4° C., samples are resuspended in 200 µL digestion buffer [50 mM Tris-HCl (pH 7.4), 0.32M sucrose, 4 mM MgCl2, 1 mM CaCl2, and 0.1 mM PMSF]. FFPE-derived samples are partially fragmented through mild sonication, using a Labsonic L sonicator (B. Braun, Biotech International) and then digested for 1 min at 37° C. with micrococcal nuclease (N.70196Y; USB) at the final concentration of 1 U/10 pg of chromatin. After centrifugation at 18,000×g for 5 min at +4° C., samples are resuspended in 200 µL sonication buffer [1×TBS, 0.1% SDS, and 1 mM Na2EDTA (pH 8.0)] and further fragmented. After centrifugation at 8,000×g for 5 min at room temperature, the first supernatant is collected (volume of ≈170 µL). The pellets are washed once with 50 µL sonication buffer, vortexed for 5 s, and centrifuged again to obtain the second supernatant (to reach a final volume of ≈220 µL). Chromatin is quantitated fluorimetrically by Qubit (Invitrogen). Immunoselection of chromatin is carried out in ChIP buffer [30mMTris-HCl (pH 7.4), 50 mM NaCl, 5 mM Na2EDTA, and 0.1 mM PMSF] using 260-600 ng of chromatin for each assay (dependent on either the amount of chromatin extracted from FFPE samples in each experiment or the number of ChIP assays to perform) and incubated 16 h at +4° C. in a rotating platform with the desired antibody. Twenty microliters of 50% vol/vol slurry rec-Protein G-Sepharose 4B Conjugate (preincubated 16 h at +4° C. with 1 mg/mL of BSA in ChIP buffer; Zymed) are added to each ChIP assay and incubated for 3 h at +4° C. After centrifugation at 2,000×g for 5 min at +4° C., pellets are washed sequentially with 2 mL of washing buffer A [50 mM Tris-HCl (pH 7.4), 1% TritonX-100, 50 mM NaCl, 5 mM Na2EDTA, and 0.1 mM PMSF] and 2 mL of washing buffer B [50 mM Tris-HCl (pH 7.4), 1% TritonX-100, 100 mM NaCl, 5 mM Na2EDTA, and 0.1 mM PMSF]. Beads are washed twice with cold Tris-Cl pH 8.0 to remove detergent, salts, and EDTA. Beads are resuspended carefully in 30 µl of the tagmentation reaction mix (10 mM Tris pH 8.0, 5 mM MgCl) containing 1 µl Tagment DNA Enzyme from the Nextera DNA Sample Prep Kit (Illumina) and incubated at 37° C. for 10 minutes in a thermocycler. The tagmentation reaction is removed by placing the reaction on a magnet and removing the supernatant, and beads are washed twice with washing buffer A and 10 mL of washing buffer C [50 mM Tris-HCl (pH 7.4), 1% TritonX-100, 150 mM NaCl, 5 mM Na2EDTA, and 0.1 mM PMSF]. Elution is carried out by adding 200 µL of elution buffer [1×Tris-EDTA (TE)/1% SDS] and incubating for 30 min at room temperature in a rotating platform. After centrifugation at 1,200×g for 5 min at room temperature, the supernatant is saved and the elution repeated to obtain a final volume of 400 µL (bound fraction). DNA Isolation. De-cross-linking was performed through an overnight incubation at 65° C. in elution buffer/0.2 M NaCl, followed by digestion with 80 µg/mL proteinase K (3 h at +45° C.). DNA was isolated by sequential extractions with one-third volume of phenol:chloroform (1:1), one volume of phenol:chloroform (1:1) and one volume of chloroform. DNA is precipitated overnight at −20° C. After centrifugation, DNA pellets are resuspended in 11 µL of TE buffer (stored at −20° C.). 1 µl of each ChIPmentation reaction is amplified in a 10 µl qPCR reaction containing 0.15 µM primers, lx SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix is preincubated at 98° C. for 45 s prior to preparation of the PCR reaction to activate the hot-start enzyme for a successful nick translation in the first PCR step. Final enrichment of the libraries (using the remaining 10 µl from the ChIP) is performed in a 50 µl reaction using 0.75 µM primers and 25 µl KAPA HIF 2× ready mix. Libraries are amplified for N cycles, where N is equal to the rounded-up Cq value determined in the qPCR reaction. Enriched libraries are purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing is performed using Illumina HiSeq 2000/2500 platforms.

EXAMPLE 9—CHIPMENTATION ON HUMAN LEUKEMIAS

B-cell chronic lymphocytic leukemia (B-CLL), also known as chronic lymphoid leukemia (CLL), is the most common type of leukemia (a type of cancer of the white blood cells) in adults. CLL affects B cell lymphocytes, which originate in the bone marrow, develop in the lymph nodes, and normally fight infection by producing antibodies.

Isolation of Primary Patient CLL Samples and Negative Selection of CD2+ Cells by Robosep Sodium butyrate (NaB) is added to fresh peripheral blood to final concentration of 5 mM. This is layered onto an equal volume of Ficoll (GE Healthcare, Amersham, UK) at room temperature and centrifuged at 13.8 g for 20 min. without brake at 4° C. The PBMC layer is extracted and washed twice in 20 ml of PBS containing 5 mM NaB. Obtained cells are washed in complete media and resuspended in 250 µl Robosep buffer and set up the Robosep machine for negative selection according to manufacturer's instructions (EasySep Human CD2 Positive Selection Kit, catalogue number 18657; StemCell Technologies, Grenoble, France). The cells that do not bind the column (i.e. CD2-population) are collected, resuspended in media and used directly for the immunoprecipitation procedure described in the invention.

Practically, derived leukemia samples from patients can be frozen using methods known in the art.

Freezing Cells

Cells should be frozen at a conc. of 1×10e8 cells/ml. Add dropwise and mix repeatedly an equal vol. of RPMI/50% FCS+20% DMSO over a period of 5 min to the leukemia cells (max. concentration 1×10e8 cells/ml, final conc. of freezing media RPMI/50% FCS+10% DMSO). Transfer 1 ml of cells in freezing media to sterile marked cryotubes. Transfer the cryotubes to a cryopreservation box having room temperature and place the cryopreservation box in a −80° C. freezer. Transfer the frozen crytubes to a nitrogen tank within 24 hours.

Thawing Cells

Thaw cells very rapidly in 37° C. water bath. Wipe the vial with 70% ethanol before opening. Transfer the 1 ml of cells immediately to a 15 ml tube containing 37° C. prewarmed RPMI/10% FCS. Centrifuge cells at 250×g 5 minutes at room temperature. Resuspend cell pellet carefully in 2 ml 37° C. prewarmed RPMI/10% FCS. Proceed to immunoprecipitation.

Immunoprecipitation

Cells are washed once with PBS and fixed with 1% paraformaldehyde in up to 1 ml PBS for 5 minutes at room temperature. Glycine is added to stop the reaction. Cells are collected at 500×g for 10 minutes at 4° C. (subsequent work was performed on ice and uses cool buffers and solutions unless otherwise specified) and is washed twice with up to 1 ml ice-cold PBS supplemented with 1 µM PMSF. The pellet is lysed in Cell Lysis Buffer (50 mM HEPES/KOH pH 7.4, 140 mM NaCl, 1 mM EDTA, 0.5 mM EGTA, 10% Glycerol, 0.5% NP-40, 0.25% Triton X-100, 1x protease inhibitors (Sigma)) for 10 minutes on ice. Nuclei are isolated by spinning the lysed cells for 10 minutes at 1,000×g at 4° C., the supernatant is discarded, and the pellet is resuspended in Sonication Buffer (10 mM Tris-HCl pH 7.6, 1 mM EDTA, 0.1% SDS) and sonicated in a 130 µl microTUBE (for up to 3×10$^6$ cells) on a Covaris S220 for 15 minutes until most of the fragments are 200-700 base pairs long (settings: duty cycle 2%, peak incident power 105 Watts, cycles per burst 200). Lysates are centrifuged at full speed for 5 minutes at 4° C. and the supernatant is transferred to a new tube. The lysate is adjusted to 200 µl per IP with a buffer composition of 20 mM HEPES, 0.1% SDS, 1% Triton X-100, 150 mM NaCl, 1 mM EDTA, 0.5 mM EGTA and incubated with an antibody of choice overnight at 4° C. on a rotator. 20 µl of Protein A (or Protein G, dependent on the antibody used) magnetic beads are blocked overnight with 0.1% BSA in PBS and added to the IP the next day for 2 hours on a rotator at 4° C. to capture the immunoprecipitated fragments. The immunoprecipitated chromatin is washed subsequently with WBI (20 mM HEPES, 150 mM NaCl, 0.1% SDS, 0.1% DOC, 1% Triton X-100, 1 mM EDTA, 0.5 mM EGTA) (twice), WBII (20 mM HEPES, 500 mM NaCl, 0.1% SDS, 0.1% DOC, 1% Triton X-100, 1 mM EDTA, 0.5 mM EGTA) (once) and WBIII (20 mM HEPES, 250 mM LiCl, 0.5% DOC, 0.5% NP-40, 1 mM EDTA, 0.5 mM EGTA) (once). Beads are washed twice with cold Tris-Cl pH 8.0 to remove detergent, salts, and EDTA. Beads are resuspended carefully in 30 µl of the tagmentation reaction mix (10 mM Tris pH 8.0, 5 mM MgCl) containing 1 µl Tagment DNA Enzyme from the Nextera DNA Sample Prep Kit (Illumina) and incubated at 37° C. for 10 minutes in a thermocycler. The tagmentation reaction is removed by placing the reaction on a magnet and removing the supernatant, and beads are washed twice with WBI. Beads are washed with WBIV (20 mM HEPES, 1 mM EDTA, 0.5 mM EGTA) (twice). Beads are then incubated with 70 µl elution buffer (0.5% SDS, 300 mM NaCl, 5 mM EDTA, 10 mM Tris-HCl pH 8.0) containing 2 µl of Proteinase K (NEB) for 1 hour at 55° C. and 8 hours at 65° C. to revert formaldehyde crosslinking, and supernatant is transferred to a new tube. Another 30 µl of elution buffer is added to the beads for 1 minute, and eluates are combined and incubated with another 1 µl of Proteinase K for 1 hour at 55° C. Finally, DNA is purified with SPRI AMPure XP beads (sample-to-beads ratio 1:2) or Qiagen MinElute columns. DNA is eluted in 11 µl of EB buffer (10 mM Tris-HCl pH 8.5). 1 µl of each ChIPmentation reaction is amplified in a 10 µl qPCR reaction containing 0.15 µM primers, 1x SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix is preincubated at 98° C. for 45 s prior to preparation of the PCR reaction to activate the hot-start enzyme for a successful nick translation in the first PCR step. Final enrichment of the libraries (using the remaining 10 µl from the ChIP) is performed in a 50 µl reaction using 0.75 µM primers and 25 µl KAPA HIF 2× ready mix. Libraries are amplified for N cycles, where N is equal to the rounded-up Cq value determined in the qPCR reaction.

Enriched libraries are purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing is performed using Illumina HiSeq 2000/2500 platforms.

EXAMPLE 10—CHIPMENTATION ON CELL LINES

K562 cells were the first human immortalised myelogenous leukemia line to be established. K562 cells are of the erythroleukemia type, and the line is derived from a 53 year old female CML patient in blast crisis. The cells are non-adherent and rounded, are positive for the bcr:abl fusion gene, and bear some proteomic resemblance to both undifferentiated granulocytes and erythrocytes.

Cells are washed once with PBS and fixed with 1% paraformaldehyde in up to 1 ml PBS for 5 minutes at room temperature. Glycine is added to stop the reaction. Cells are collected at 500×g for 10 minutes at 4° C. (subsequent work was performed on ice and uses cool buffers and solutions unless otherwise specified) and is washed twice with up to 1 ml ice-cold PBS supplemented with 1 µM PMSF. The pellet is lysed in Cell Lysis Buffer (50 mM HEPES/KOH pH 7.4, 140 mM NaCl, 1 mM EDTA, 0.5 mM EGTA, 10%

Glycerol, 0.5% NP-40, 0.25% Triton X-100, lx protease inhibitors (Sigma)) for 10 minutes on ice. Nuclei are isolated by spinning the lysed cells for 10 minutes at 1,000×g at 4° C., the supernatant is discarded, and the pellet is resuspended in Sonication Buffer (10 mM Tris-HCl pH 7.6, 1 mM EDTA, 0.1% SDS) and sonicated in a 130 µl microTUBE (for up to 3×10$^6$ cells) on a Covaris S220 for 15 minutes until most of the fragments are 200-700 base pairs long (settings: duty cycle 2%, peak incident power 105 Watts, cycles per burst 200). Lysates are centrifuged at full speed for 5 minutes at 4° C. and the supernatant is transferred to a new tube. The lysate is adjusted to 200 µl per IP with a buffer composition of 20 mM HEPES, 0.1% SDS, 1% Triton X-100, 150 mM NaCl, 1 mM EDTA, 0.5 mM EGTA and incubated with an antibody of choice overnight at 4° C. on a rotator. 20 µl of Protein A (or Protein G, dependent on the antibody used) magnetic beads are blocked overnight with 0.1% BSA in PBS and added to the IP the next day for 2 hours on a rotator at 4° C. to capture the immunoprecipitated fragments. The immunoprecipitated chromatin is washed subsequently with WBI (20 mM HEPES, 150 mM NaCl, 0.1% SDS, 0.1% DOC, 1% Triton X-100, 1 mM EDTA, 0.5 mM EGTA) (twice), WBII (20 mM HEPES, 500 mM NaCl, 0.1% SDS, 0.1% DOC, 1% Triton X-100, 1 mM EDTA, 0.5 mM EGTA) (once) and WBIII (20 mM HEPES, 250 mM LiCl, 0.5% DOC, 0.5% NP-40, 1 mM EDTA, 0.5 mM EGTA) (once). Beads are washed twice with cold Tris-CI pH 8.0 to remove detergent, salts, and EDTA. Beads are resuspended carefully in 30 µl of the tagmentation reaction mix (10 mM Tris pH 8.0, 5 mM MgCl) containing 1 µl Tagment DNA Enzyme from the Nextera DNA Sample Prep Kit (Illumina) and incubated at 37° C. for 10 minutes in a thermocycler. The tagmentation reaction is removed by placing the reaction on a magnet and removing the supernatant, and beads are washed twice with WBI. Beads are washed with WBIV (20 mM HEPES, 1 mM EDTA, 0.5 mM EGTA) (twice). Beads are then incubated with 70 µl elution buffer (0.5% SDS, 300 mM NaCl, 5 mM EDTA, 10 mM Tris-HCl pH 8.0) containing 2 µl of Proteinase K (NEB) for 1 hour at 55° C. and 8 hours at 65° C. to revert formaldehyde crosslinking, and supernatant is transferred to a new tube. Another 30 µl of elution buffer is added to the beads for 1 minute, and eluates are combined and incubated with another 1 µl of Proteinase K for 1 hour at 55° C. Finally, DNA is purified with SPRI AMPure XP beads (sample-to-beads ratio 1:2) or Qiagen MinElute columns. DNA is eluted in 11 µl of EB buffer (10 mM Tris-HCl pH 8.5). 1 µl of each ChIPmentation reaction is amplified in a 10 µl qPCR reaction containing 0.15 µM primers, lx SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix is preincubated at 98° C. for 45 s prior to preparation of the PCR reaction to activate the hot-start enzyme for a successful nick translation in the first PCR step. Final enrichment of the libraries (using the remaining 10 µl from the ChIP) is performed in a 50 µl reaction using 0.75 µM primers and 25 µl KAPA HIF 2× ready mix. Libraries are amplified for N cycles, where N is equal to the rounded-up Cq value determined in the qPCR reaction. Enriched libraries are purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing is performed using Illumina HiSeq 2000/2500 platforms.

EXAMPLE 11—CHIPMENTATION ON MODEL ORGANISMS OR PARTS OF MODELORGANSISM THAT MAY HAVE LOW CELL NUMBERS

The methods of the invention require only low input amounts for analyzing histone-DNA interactions genome-wide. It is anticipated that the invention allows analysis of early developmental stages of individual animals that consist of low cell numbers. One example is the zebrafish (*Danio rerio*), which is a tropical freshwater fish belonging to the minnow family (Cyprinidae) of the order Cypriniformes. Native to the Himalayan region, it is a popular aquarium fish, frequently sold under the trade name zebra danio. The zebrafish is also an important vertebrate model organism in scientific research. Upon fertilization, eggs divide and after 4 hours the embryo already consists of several thousand cells, which may be enough to analyze a histone modification in a single embryo using the invention. Pooling of embryos of earlier developmental stages can also be used to increase cell numbers so the invention can be used on the cells. The suggested protocol can be adapted to other organisms of all kinds, for example mouse, when isolation of desired cell types/tissues/developmental stages are carried out with methods well known in the art. In certain circumstances it can be hard to obtain the high number of embryos required for this technique at once, i.e. in over-expression or knock-down experiments. In these cases, embryo processing and fixation can be performed in batches that can be frozen in liquid nitrogen and stored at −80° C. until the total number of embryos required is collected. To ensure that all embryos are collected at the same developmental stage, mate zebrafish females and males only for 15 min, collect the embryos in Petri dishes with embryo medium (E3 medium: 5 mM NaCl, 0.17 mM KCl, 0.4 mM CaCl2, 0.16 mM MgSO4) and raise them at 28° C. until they reach the desired stage of development. Collect the embryos in 0.50 ml of E3 and add 5 µl of pronase (Roche, Ref. 10165921001) at 30 mg/ml. Shake gently and incubate the embryos at 28° C. It takes about 15 min for chorion softening. Examine them under a stereomicroscope until the first embryos without chorion are detected. Immediately wash the embryos thoroughly with E3 medium (three times) to remove the pronase completely. To release embryos from their chorions, pipette them carefully in the E3 medium with a pipette. Transfer the embryos with a pipette to a 0.5 ml tube and remove all E3. Add 0.46 ml E3 and 0.4 ml 4% PFA (4% PFA (SIGMA P6148), phosphate buffer 200 mM, pH 7.4, NaOH 0.02 N) to the embryos and shake them gently at room temperature for 15 min. Add glycine (Merck, 1.00590.1000) to a final concentration of 0.125 M to quench formaldehyde and shake gently for 5 min at room temperature. Remove supernatant and rinse embryos three times in ice-cold 1×PBS. Remove PBS and proceed with cell lysis or freeze in liquid nitrogen and store pellets at −80° C. Work in a in a 4° C. cold room from now on. Mix thoroughly the Dyna Protein G magnetic beads. Take 10 µl (per antibody) and wash them in 1 ml fresh block solution (0.5% BSA in 1×PBS; can be kept at 4° C. for a week) in a 1.5 ml safe-lock tube. Collect the beads by spinning at 3000 rpm for 3 min. Wash the beads in 1.5 ml block solution two more times. Resuspend the beads vigorously after each wash. Collect the beads with the magnetic stand (DYNAMag-Spin, Invitrogen 123.20D) and discard supernatant. Resuspend the beads in 10 µl of block solution and add the antibody. Possible amounts for some antibodies: 1 µl of anti-H3K4me1 Ab (Diagenode, Cat. No. CS-037-100, concentration not determined), 1 µl of anti-H3K4me3

Ab (Diagenode, Cat.No. pAb-003-050, 1.1 µg/µl), 1 µl of anti-H3K27ac Ab (Abcam, Cat.No. ab4729, 0.80 mg/ml) and 1 µl of anti-H3K27me3 (Millipore 07-449, 1 mg/ml). Incubate the antibody at 4° C. for a minimum of 4 h or overnight on a rotating platform. Collect the beads with the magnetic stand and remove supernatant. Wash beads in 0.2 ml block solution in the cold room. Repeat this step two more times. Resuspend the beads in 10 µl of block solution. Add protease inhibitors (Complete tablet, Roche 11 697 498 001) to all lysis buffers just before use. (A 50× Stock of Complete (1 tablet/ml 1×PBS) can be kept at −20° C. for two months). Resuspend the crosslinked embryos in 0.13 ml cell lysis buffer (50 mM Tris-HCl pH 7.5, 10 mM EDTA, 1% SDS). Pipette up and down and squeeze embryos for disruption. Lay the tube on ice and incubate for 10 min. Leave samples 15 min on ice and refresh the ice-water bath. Sonicate in a 130 µl microTUBE (Covaris, for up to 3×10$^6$ cells) on a Covaris S220 for 10-60 minutes (depending on how many embryos used, needs to be determined empirically) until most of the fragments are 200-700 base pairs long (settings: duty cycle 2%, peak incident power 105 Watts, cycles per burst 200).

Add 2 volumes of IP dilution buffer (16.7 mM Tris-HCl pH 7.5, 167 mM NaCl, 1.2 mM EDTA, 0.01% SDS). Add 1% Triton X-100 to sonicated chromatin. Spin at 14,000 rpm for 10 min at 4° C. and transfer chromatin to new tube. Add 10 µl of antibody/magnetic beads mix to each aliqut of sonicated chromatin. Incubate the tubes overnight on a rotating platform at 4° C. Collect the beads from tubes with the magnetic stand and remove supernatant. Add 0.2 ml RIPA wash buffer (50 mM HEPES pH 7.6, 1 mM EDTA, 0.7% DOC, 1% Igepal, 0.5 M LiCl) to each tube. Shake tubes gently to resuspend the beads. Collect the beads with the magnetic stand and remove supernatant. Repeat the previous step three more times. Beads are washed twice with cold Tris-CI pH 8.0 to remove detergent, salts, and EDTA. Beads are resuspended carefully in 30 µl of the tagmentation reaction mix (here: 2 µl Tagment DNA Enzyme from the Nextera DNA Sample Prep Kit (Illumina), 15 µl 2×Tagment DNA buffer from the Nextera DNA Sample Prep Kit and 13 µl nuclease free water) and incubated at 37° C. for 3 minutes in a thermocycler. The tagmentation reaction is removed by placing the reaction on a magnet and removing the supernatant, and beads are washed twice with RIPA. Wash once with 1 ml 1×TBS (50 mM Tris pH 7.5, 150 mM NaCl), Collect the beads with the magnetic stand and remove supernatant. Resuspend the beads in 200 µl 1×TBS. Spin at 3000 rpm for 3 min and aspirate any residual TBS. Add 60 µl of elution buffer (50 mM NaHCO3, 1% SDS). Elute DNA-protein complexes from the beads at 65° C. for 10-15 min with brief vortexing every 2 min. Spin down beads at 14,000 rpm for 1 min. Transfer 650 µl of supernatant to a 1.5 ml safe-lock tube. Add 300 mM NaCl. Reverse formaldehyde crosslinks during 6 h or overnight at 65° C. Add RNase A to a final concentration of 0.33 µg/µl and incubate at 37° C. for 2 h. Add 1 volume Phenol/Chlorphorm/Isoamylalcohol (25:24:1, AMRESCO 0883), mix and spin for 5 min. Transfer upper phase to a new 1.5 ml safe-lock tube. Add 1 pg of glycogen. Add 1/10 3 M NaAc and two volumes of 100% EtOH. To precipitate DNA spin for 10 min at 14,000 rpm. Wash pellet with 500 µl 75% cold-EtOH and spin for 5 min at 14,000 rpm at 4° C. Air-dry pellets at room temperature and resuspend in 70 µl 10 mM Tris-HCl, pH 8. Purify the DNA (from both the input and the ChIP reaction) using the QIAquick PCR Purification Kit (Qiagen 28104) (follow instructions provided with the kit). Elute in 11 µl of EB buffer (10 mM Tris-HCl pH 8.5). 1 µl of each ChIP-mentation reaction is amplified in a 10 µl qPCR reaction containing 0.15 µM primers, lx SYBR green and 5 µl KAPA HIFI 2× ready mix to estimate the optimum number of enrichment cycles with the following program: 72° C. 5 min, 98° C. 30 s, 24 cycles of 98° C. 10 s 63° C. 30 s 72° C. 30 s, and a final elongation at 72° C. for 1 min. KAPA HIFI 2× ready mix is preincubated at 98° C. for 45 s prior to preparation of the PCR reaction to activate the hot-start enzyme for a successful nick translation in the first PCR step. Final enrichment of the libraries (using the remaining 10 µl from the ChIP) is performed in a 50 µl reaction using 0.75 µM primers and 25 µl KAPA HIF 2× ready mix. Libraries are amplified for N cycles, where N is equal to the rounded-up Cq value determined in the qPCR reaction. Enriched libraries are purified with a size-selection procedure using SPRI AMPure XP beads with a ratio of 0.7:1 (beads:sample) to remove long fragments (>600 bp), recovering the remaining DNA in the reaction with a 2:1 ratio (beads:sample). Sequencing is performed using Illumina HiSeq 2000/2500 platforms.

EXAMPLE 12—METHODS OF THE INVENTION USING A CHEMICAL SUBSTANCE AS AGENT BINDING TO CHROMATIN

In vivo genome-wide occupancy analysis of biotinylated JQ1 (in vivo Chem-seq). Exponentially growing MM1.S cells (2×108 cells per sample) are treated simultaneously with either 5 µM biotinylated JQ1 (Bio-JQ1) or DMSO (vehicle) and 1% formaldehyde for 20 min in cell culture medium. Chemical cross-linking is terminated by addition of TRIS buffer, pH 7.5, to a final concentration of 300 mM TRIS. Cells are harvested using a silicon scraper, centrifuged, and the derived pellets washed three times with PBS. Cell nuclei are prepared as follows: cells are lysed in 50 mM HEPES, pH 7.5, 140 mM NaCl, 1 mM EDTA, 10% glycerol, 0.5% NP-40, 0.25% Triton X-100 plus protease inhibitor cocktail 'complete' (Roche), and cell nuclei are washed once with 10 mM Tris-HCL, pH 8.0, 200 mM NaCl, 1 mM EDTA, 0.5 mM EGTA and protease inhibitors. Nuclei are resuspended and sonicated in 50 mM HEPES-KOH, pH 7.5, 140 mM NaCl, 1 mM EDTA, 1 mM EGTA,1% Triton X-100, 0.1% Na-deoxycholate, 0.1% SDS (sonication buffer) and protease inhibitor cocktail at 18 W for 10 cycles (30 s each) on ice with 30-s intervals between cycles. Sonicated lysates are cleared by centrifugation and incubated for 16-20 h at 4° C. with magnetic streptavidin Dynabeads (MyOne Streptavidin T1, Invitrogen) (beads are blocked in PBS containing 0.5% BSA before this incubation step). Following incubation in nuclear sonicated lysate, beads are washed twice in sonication buffer, once in sonication buffer containing 500 mM NaCl, once in LiCl buffer (20 mM Tris-HCL, pH 8.0, 1 mM EDTA, 250 mM LiCl, 0.5% NP-40, 0.5% Na-deoxycholate). Beads are washed twice with cold Tris-CI pH 8.0 to remove detergent, salts, and EDTA. Beads are resuspended carefully in 30 µl of the tagmentation reaction mix (here: 2 µl Tagment DNA Enzyme from the Nextera DNA Sample Prep Kit (Illumina), 15 µl 2×Tagment DNA buffer from the Nextera DNA Sample Prep Kit and 13 µl nuclease free water) and incubated at 37° C. for 3 minutes in a thermocycler. The tagmentation reaction is removed by placing the reaction on a magnet and removing the supernatant, and beads are washed twice with sonication buffer. Beads are then washed once in 10 mM TRIS, pH 7.5, 0.1 mM EDTA. Bound protein-DNA complexes are subsequently eluted in 50 mM Tris-HCL, pH 8.0, 10 mM EDTA, 1% SDS at 65° C. for 15 min, and cross-links are reversed by overnight incubation of the eluate at 65° C. Contaminating RNA and protein are digested by addition of RNase and Proteinase K, respectively, and the DNA purified as previously described 34. Finally, purified DNA fragments are massively parallel sequenced.

In vitro genome-wide occupancy analysis of biotinylated JQ1 (in vitro Chem-seq). Exponentially growing, untreated MM1.S cells are fixed with 1% formaldehyde for 20 min in cell culture medium. Chemical cross-linking is terminated, cell nuclei prepared and sonicated nuclear lysate obtained as described above. Unlike in the in vivo protocol, however, Streptavidin Dynabeads are pre-incubated in PBS containing 0.5% BSA and either 200 µM biotinylated drug or vehicle (DMSO) for 6 h.

Drug-bound beads are subsequently washed four times in PBS/0.5% BSA to remove unbound drug, and incubated in nuclear sonicated lysate for 16-20 h at 4° C. All the following steps are identical to those described above (in vivo Chem-seq method).

In vitro genome-wide occupancy analysis using biotinylated AT7519 (in vitro Chem-seq). Exponentially growing, untreated MM1.S cells are fixed with 0.5% formaldehyde for 5 min in cell culture medium. Chemical cross-linking is terminated by addition of TRIS buffer, pH 7.5, to a final concentration of 300 mM TRIS. Cells are washed 3× in PBS and cell nuclei prepared as follows: cell nuclei are lysed in 50 mM HEPES, pH 7.5, 140 mM NaCl, 1 mM EDTA, 10% glycerol, 0.5% NP-40, 0.25% Triton X-100 plus protease inhibitor cocktail 'complete' (Roche), and cell nuclei are washed once with 10 mM Tris-HCL, pH 8.0, 200 mM NaCl, 1 mM EDTA, 0.5 mM EGTA and protease inhibitors. Nuclei are resuspended and sonicated in 50 mM HEPES-KOH, pH 7.5, 140 mM NaCl, 1 mM EDTA, 1 mM EGTA, 0.5% NP-40, 0.5% Triton-X (sonication buffer). Pellets are sonicated at 9-12 W for 4 cycles (30 s each) in a Misonix sonicator on ice with 1-min rest intervals between cycles. Drug-bound beads are added to the cleared sonicate and the precipitation allowed to proceed for 12-18 h. Drug-bound beads are sub-sequentially washed three times in sonication buffer. Beads are washed twice with cold Tris-CI pH 8.0 to remove detergent, salts, and EDTA. Beads are resuspended carefully in 30 µl of the tagmentation reaction mix (here: 2 µl Tagment DNA Enzyme from the Nextera DNA Sample Prep Kit (Illumina), 15 µl 2×Tagment DNA buffer from the Nextera DNA Sample Prep Kit and 13 µl nuclease free water) and incubated at 37° C. for 3 minutes in a thermocycler. The tagmentation reaction is removed by placing the reaction on a magnet and removing the supernatant, and beads are washed twice with sonication buffer. Proteins are eluted in 1% SDS, and cross-links are reversed by overnight incubation of the eluate at 65° C. in 1% SDS. Contaminating RNA and protein are digested by sequential incubation with RNase A and Proteinase K, and the DNA purified as previously described. Purified DNA fragments are subjected to massively parallel sequencing.

Genome-wide occupancy analysis of biotinylated psoralen by Chem-seq Cell nuclei are prepared from exponentially growing MM.S cells using the Nuclei EZ prep kit (Sigma). Nuclei are then resuspended in ice-cold PBS and directly incubated with 5 µM biotinylated psoralen or vehicle (DMSO) for 30 min at 4° C. Nuclei are washed once in PBS and immediately irradiated at 360 nm for 30 min (Stratalinker) on ice. Nuclei are resuspended and sonicated in 50 mM HEPES-KOH, pH 7.5, 140 mM NaCl, 1 mM EDTA, 1 mM EGTA, 1% Triton X-100, 0.1% Na-deoxycholate, 0.1% SDS (sonication buffer) and protease inhibitor cocktail at 18 W for 10 cycles (30 s each) on ice with 30 s intervals between cycles. Sonicated lysates are cleared by centrifugation and incubated for 16-20 h at 4° C. with magnetic Streptavidin Dynabeads (MyOne Streptavidin T1, Invitrogen) (beads are blocked in PBS containing 0.5% BSA before this incubation step). Following incubation in nuclear-sonicated lysate, beads are washed twice in sonication buffer, once in sonication buffer containing 500 mM NaCl, once in LiCl buffer (20 mM Tris-HCL, pH 8.0, 1 mM EDTA, 250 mM LiCl, 0.5% NP-40, 0.5% Na-deoxycholate).

Beads are washed twice with cold Tris-CI pH 8.0 to remove detergent, salts, and EDTA. Beads are resuspended carefully in 30 µl of the tagmentation reaction mix (here: 2 µl Tagment DNA Enzyme from the Nextera DNA Sample Prep Kit (Illumina), 15 µl 2×Tagment DNA buffer from the Nextera DNA Sample Prep Kit and 13 µl nuclease free water) and incubated at 37° C. for 3 minutes in a thermocycler. The tagmentation reaction is removed by placing the reaction on a magnet and removing the supernatant, and beads are washed twice with sonication buffer, followed by washing once in 10 mM TRIS, pH 7.5, 0.1 mM EDTA. Bound protein-DNA complexes are subsequently eluted in 50 mM Tris-HCL, pH 8.0, 10 mM EDTA, 1% SDS and 10 mM Biotin, and the eluate incubated o/n at 65° C. Contaminating RNA and protein are digested by addition of RNase and Proteinase K, respectively, and the DNA purified as previously described. Finally, purified DNA samples are irradiated at 254 nm for 5 min (Stratalinker) to reverse psoralen-DNA cross-links, followed by library preparation, massively parallel DNA sequencing.

EXAMPLE 13—PARAMETER OPTIMIZED PROTOCOL FOR IMPROVED SIGNAL-TO-NOISE RATIO

Multiple parameters can be optimized to improve signal-to-noise ratio in experiments using the methods of the present invention. An exemplary protocol provided herein reduces tagmentation time to about 1 minute by using a tube transfer and a specific tagmentation buffer. The protocol is compatible with various protocols for ChIP, like the protocols described in Examples 3, 4 and 5, respectively.

This makes it easy to apply the protocol to antibodies that work best with a certain ChIP protocol. The best signal-to-noise ration was observed by following the protocols of Examples 3, 4 or 5 until the beads carrying immunoprecipitated chromatin were washed with LiCl-containing wash buffer (WBIII for Example 3, RIPA-LiCl for Example 4, and TF-WBIII for Example 5). Then, the beads were washed once with cold Tris-CI pH 8.0 to remove detergent, salts, and EDTA. Subsequently, the beads were again washed with cold Tris-CI pH 8.0 but the reaction was not placed on a magnet to discard supernatant immediately. Instead, the whole reaction including beads was transferred to a new tube, and then placed on a magnet to remove supernatant. This decreased tagmentation of unspecific chromatin fragments sticking to the tube wall. Then, the beads were carefully resuspended in 25 µl of the tagmentation reaction mix (10 mM Tris pH 8.0, 5 mM MgCl2, 10% w/v dimethylformamide) containing 1 µl Tagment DNA Enzyme from the Nextera DNA Sample Prep Kit (Illumina) and incubated at 37° C. for 1 minute in a thermocycler. Dimethylformamide as a polar aprotoc solvent that can enhance nucleophilic reactions and may therefore be beneficial for transposition reaction as the transposase uses a watermolecule for a nucleophilic attac as the mechanism for integrating oligonucleotides into DNA. Alternatively, the Tagment DNA buffer from the Nexera kit may be used. The tagmentation reaction was removed and the beads washed twice with WBI (Example 3), RIPA (Example 4), or TF-WBI (Example 5). The ChIP protocol was then followed, but the reaction was again transferred in a new tube when washing for the second time with WBIV (Example 3), TE (Example 4), or TET (Example 5) as already described in a previous step. This decreased carry-over of tagmented unspecific fragments sticking to the tube wall. The experiment was done using 500 k cells and compared to the standard protocol, without tube transfer and not using dimethylformamide, using 500 k cells or 10Mio cells, respectively. The results are shown in FIG. 12. The optimized protocol gives equal or higher signal-to-noise-ratio than an experiment with 10 mio cells using the standard protocol of the methods described herein.

EXAMPLE 14—OPTIMIZED ASSAY DURATION

To further optimize assay duration, the heating temperature to reverse cross-links may be increased. Accordingly, the methods of the present invention were performed with the additional step of "end-repair" to fill in the adaptor sequence on the reverse strand, as e.g. in the Nextera protocol, where a 5 minute 72° C. PCR step before the initial denaturation is recommended. To do so, a PCR mastermix was added and the sample heated to 72° C., followed by reverse cross-linking at 95° C. As the transposase could "stick" to the DNA, protocols suggest a "striping" of the transposase with EDTA before the end-repair, quenching the EDTA with MgCl2 to allow end repair (EDTA would disturb any PCR). Several ultra-fast protocols were performed, including protocols comprising ChIPmentation until the final wash step, instead of immediately eluting the chromatin from the beads with elution buffer the beads were resuspended by adding a PCR mastermix directly for end repair (below a); EDTA to ensure complete stripping of transposase from the chromatin, followed by quenching with MgCl2, followed by addition of the PCR mastermix for end repair (below b); or as above just with a faster procedure (below c). Subsequently, the reaction was incubated at 72° C. for 5 minutes to repair the ends (=fill the adapter ends of the second strand), crosslinks were reversed at 95° C. for 10-15 minutes and the reactions were topped up with fresh PCR mastermix (or not in case of protocol 2c), primers were added and library was amplified. In case of (a), the ChIPmentation procedure was followed until the beads carrying the chromatin were washed the last time. The supernatant was discarded and the beads were resuspended in cold 14 µl 1×KAPA HiFi Hot Start ReadyMix (preheated to 95° C. for 30 s). The reaction was incubated for 5 minutes at 72° C., then for 10 minutes at 95° C. Afterwards, the reaction was cooled to 4° C. For the subsequent PCR, 1.5 µl of forward and reverse primers each (25 µM each), 15 µl H₂0 and 18 µl 2×KAPA HiFi Hot Start ReadyMix (preheated to 95° C. for 30 s) was added and the DNA was amplified. In case of (b), the ChIPmentation procedure was followed until the beads carrying the chromatin were washed the last time and the supernatant was discarded. The beads were resuspended in 8 µl 50 mM EDTA and incubated 30 minutes at 50° C. Then, 2 µl 200 mM MgCl2 were added and incubated at 30 minutes at 50° C., before 10 µl 2×KAPA HiFi Hot Start ReadyMix were added (preheated to 95° C. for 30 s) and incubated for 5 minutes at 72° C. Subsequently, the reaction was incubated for 10 minutes at 95° C., and then cooled to 4° C. Finally, 1.5 µl 25 µM forward and reverse primer each, 12 µl H2O and 15 µl 2×KAPA HiFi Hot Start ReadyMix were added (preheated to 95° C. for 30 s) and the reaction was amplified using 12-18 cycles according to the ChIPmentation library amplification parameters. In case of (c), the ChIPmentation procedure was followed until the beads carrying the chromatin were washed the last time and the supernatant was discarded. Then, 11 µl 20 mM EDTA were added and incubated for 10 minutes at 50° C. Subsequently, 11 µl 20 mM MgCl2+25 µl 2×KAPA HiFi Hot Start ReadyMix were added (preheated to 95° C. for 30 s) and incubated for 5 minutes at 72° C. The reaction was incubated for 10 minutes at 95° C., and then cooled to 4° C. Then, 1.5 µl 25 µM forward and reverse primer each were added and the reaction was amplified in 12-18 cycles according to the ChIPmentation library amplification parameters. The results are shown in FIG. 15. Accordingly, using the ultra-fast procedure as described herein results in comparable data validity while significantly reducing experimental time. In particular, in case of (c), the entire procedure from cells culture to amplified library can be completed in a single working day. More specifically, the experimental steps comprise harvesting cells and preparing the beads (following Example 5) (20 min), fixing cells with formaldehyde and washing the pellet (45 min), lysing and sonifying the cells (40 min), isolating chromatin with an antibody (=immunoprecipitation step, 3 hrs when following Example 5), washing the chromatin (30 min), adding the transposase (10 min), subsequent washing (10 min), end repair and reverse cross-linking (30 min), amplification of library (45 min) and purification of the library (45 min), resulting in a total time of <8 hrs. Here, isolation of specific cells from patients (e.g CD4+ T cells) can still be incorporated in the timeline of a long working day (+90 minutes for blood draw and CD4+ isolation). If a second operator is preparing an appropriate sequencing machine (e.g Illumina MiSeq), the samples can be sequenced over night, resulting in a complete workflow from patient blood draw to sequences in ~24 hrs, allowing personalized epigenomes on a clinical time-scale. More specifically, when the ChIPmentation sample is sequenced on an Illumina MiSeq using the MiSeq Reagent Kit v3, 50 sequencing cycles from around 25 million clusters can be completed in 5-6 hours, which results in a total timeframe of ~15 hours from blood draw to sequenced ChIPmentation experiment.

EXAMPLE 15—ULTRA-FAST ASSAY USING AN ALTERNATIVE TRANSPOSASE

An alternative transposase was prepared according to Picelli et al. (2014) Genome Research 24:2033-40. In brief, the Tn5 enzyme is produced and stored according to Picelli et al. (as above) having the amino acid sequence encoded by the sequence of SEQ ID NOs:1 or 2, wherein SEQ ID NO:1 relates to the nucleic acid encoding the homemade transposase containing a C-terminal intein tag and a chitin-binding domain and SEQ ID NO:2 relates to the core transposase enzyme, and using an expression vector having the sequence of SEQ ID NO:3, then an aliquot of the Tn5 is diluted in Tn5 dilution buffer (dependent on the activity of the Tn5), oligonucleotides are prepared to be loaded on the Tn5 and the diluted Tn5 is then loaded with oligonucleotides (all steps as previously described). The "homemade" Tn5 can be used as a direct substitute. The following buffers were used: Tn5 dilution buffer (50 mM Tris-HCl at pH 7.5; 100 mM NaCl; 0.1 mM EDTA; 50% glycerol; 0.1% Triton X-100 and 1 mM DTT (always add fresh before diluting—1 µl 1M DTT per 1 ml of buffer). For pre-annealing of Mosaic End oligonucleotides, the following procedure was followed: (1) preparation of 100 µM equimolar mixture of Tn5ME-A+Tn5MErev and Tn5ME-B+Tn5MErev oligonucleotides; using Tn5MErev: 5'-[phos]CTGTCTCTTATA-CACATCT-3' (SEQ ID NO:4); Tn5ME-A: 5'-TCGTCGGCAGCGTCAGATGTGTATAAGAGACAG-3' (SEQ ID NO:5) and Tn5ME-B: 5'-GTCTCGTGGGCTCGGAGATGTGTATAAGA-GACAG-3' (SEQ ID NO:6), wherein Tn5MErev is phosphorylated at the 5' end; (2) incubation of both mixes at $95^2$C for 3 minutes and incubation overnight in switched off thermoblock to cool down, afterwards both were mixed 1:1 (3) generation of Transposomes was done by adding 0.143 volumes of pre-annealed oligonucleotides 1:1 to the Tn5 dilution and incubation for 1 h at R/T and incubation on ice until needed.

For each experiment 300,000 K562 leukemia cell line cells were washed once with PBS and fixed with 1% paraformaldehyde in up to 1.5 ml PBS for 10 minutes at room temperature. Glycine was added to stop the reaction. Cells were collected at 500×g for 10 minutes at 4° C. (subsequent work was performed on ice and cool buffers and solutions were used unless otherwise specified) and washed twice with up to 1 ml ice-cold PBS supplemented with 1 µM PMSF. The pellet was lysed in sonication buffer (10 mM Tris-HCl, pH 8.0, 1 mM EDTA, pH 8.0, 0.25% SDS, 1x protease inhibitors (Sigma)) and sonicated in a 1 ml milliTUBE in a Covaris S220 for 20 minutes until most of the fragments were 200-700 base pairs long (settings: duty cycle 5%, peak incident power 140 Watts, cycles per burst 200). Lysates were adjusted to RIPA conditions (10 mM Tris-HCl, pH 8.0, 1 mM EDTA, pH 8.0, 140 mM NaCl, 1% Triton x-100, 0.1% SDS, 0.1% DOC, 1x protease inhibitors (Sigma)). Lysates were centrifuged at full speed for 5 minutes at 4° C., and the supernatant containing the sonicated chromatin was transferred to a new tube. In parallel, 10 µl magnetic Protein A or Protein G beads (dependent on the antibody used) were blocked and conjugated to an antibody by washing and resuspending twice in PBS, 0.5% BSA, 0.5% Tween-20. The antibody was added and bound to the beads by rotating>1 hour at room temperature. Used antibodies were H3K4me3 (1 µg/IP, Diagenode). Blocked antibody-conjugated beads were then placed on a magnet, supernatant was removed, and the sonicated lysate was added to the beads followed by incubation for 3 hours at 4° C. on a rotator. Beads were washed subsequently with 150 µl RIPA (twice), RIPA-500 (10 mM Tris-HCl, pH 8.0, 1 mM EDTA, pH 8.0, 500 mM NaCl, 1% Triton x-100, 0.1% SDS, 0.1% DOC,) (twice), RIPA-LiCl (10 mM Tris-HCl, pH 8.0, 1 mM EDTA, pH 8.0, 250 mM LiCl, 1% Triton X-100, 0.5% DOC, 0.5% NP40), and Tris pH 8.0 (twice). 11 µl 20 mM EDTA were added to the beads and incubated for 10 minutes at 50° C. Subsequently, 11 µl 20 mM MgCl2+25 µl 2×KAPA HiFi Hot Start ReadyMix were added (preheated to 95° C. for 30 s) and incubated for 5 minutes at 72° C. The reaction was incubated for 10 minutes at 95° C., and then cooled to 4° C. Then, 1.5 µl 25 µM forward and reverse primer each were added and the reaction was amplified in 10-14 cycles according to the ChIPmentation library amplification parameters. The results are shown in FIG. 15, demonstrating ChIPmentation sequencing libraries for H3K4me3 using either the commercially available Illumina Tn5 transposomes or "homemade" Tn5 transposomes from 2 different sources. This experiment demonstrates identical results using either the commercially available Illumina transposase (tn5) or homemade transposase enzyme.

---

The invention claimed is:

1. A method for isolating nucleic acid from chromatin, the method comprising:
  (a) adding an agent binding to chromatin to a sample comprising a nucleic acid;
  (b) isolating the chromatin bound by said agent;
  (c) adding a transposase to the isolated chromatin of step (b); and
  (d) isolating the nucleic acid from the chromatin of step (c).

2. The method of claim 1, wherein the method further comprises generating a sequence library from the isolated nucleic acid of (d).

3. The method of claim 2, wherein the agent is an antibody.

4. The method of claim 1, wherein the method further comprises:
  (e) amplifying the isolated nucleic acid of (d);
  (f) sequencing the amplified nucleic acid of (e); and
  (g) identifying molecular interactions of the nucleic acid.

5. The method of claim 4, wherein the agent is an antibody.

6. The method of claim 1, wherein the nucleic acid is DNA.

7. The method of claim 1, wherein the sample comprising a nucleic acid has been prepared by
  (i) cultivating and harvesting cells;
  (ii) fixing cells;
  (iii) lysing cells and thereby obtaining a first sample comprising a nucleic acid; and
  (iv)سonicating the first sample and thereby obtaining a second sample comprising a nucleic acid, wherein said second sample is to be used in the method of claim 1.

8. The method of claim 7, wherein the method further comprises a step of reversing cross-links introduced during fixing cells of step (ii).

9. The method of claim 7, wherein the cells comprise nucleic acid-protein complexes.

10. The method of claim 7, wherein the cells are human cells, animal cells, bacterial cells, yeast cells, archaeal cells, plant cells or viruses.

11. The method of claim 10, wherein the human or animal cells are diseased cells or non-diseased cells or cells derived from diseased or non-diseased tissue.

12. The method of claim 10, wherein the human or animal cells are cancer cells, immune cells, blood cells or stem cells.

13. The method of claim 12, wherein the cancer cells are derived from a solid cancer or blood cancer.

14. The method of claim 13, wherein the blood cancer is leukemia.

15. The method of claim 13, wherein the solid cancer is a tumour.

16. The method of claim 10, wherein the animal cells are derived from an animal belonging to a rare species, endangered species and/or is a model organism.

17. The method of claim 10, wherein the cells are embryonic cells.

18. The method of claim 7, wherein step (ii) comprises the addition of a chemical substance and/or physical means.

19. The method of claim 18, wherein the chemical substance is formaldehyde or paraformaldehyde.

20. The method of claim 18, wherein the physical means comprise UV-light or laser.

21. The method of claim 7, wherein step (iv) comprises sonication until most of the nucleic acid fragments are 20-5000, preferably 200-300, base pairs long.

22. The method of claim 1, wherein the agent binding to chromatin is a chemical substance.

23. The method of claim 22, wherein the chemical substance is a drug or a tool compound.

24. The method of claim 23, wherein the chemical substance is biotinylated.

25. The method of claim 1, wherein the agent is an antibody that specifically binds to histones, transcription factors or proteins binding to histones and/or transcription factors.

26. The method of claim 25, wherein the proteins binding to histones and/or transcription factors are nucleic acid remodeling proteins or chromatin modifying enzymes.

27. The method of claim 25, wherein the histone is H3.3, H2A.Z, CENP-A, H3.2, H3.3A, H3.3B, H4 or H3.1.

28. The method of claim 25, wherein the histone is a modified histone, wherein the modification is methylation, acetylation, propionylation, butyrylation, crotonylation, 2-hydroxyisobutyrylation, malonylation, succinylation and/or ribosylation.

29. The method of claim 28, wherein the modified histone is H3K4me1/2/3, H2BK5me1, H3K27me1/2/3, H3K9me1/2/3, H4K20me1, H3K79me1, H3K36me3, H2AK5ac, H2AK9ac, H2BK5ac, H2BK12ac, H2BK20ac, H2BK120ac, H3K4ac, H3K9ac, H3K14ac, H3K18ac, H3K23ac, H3K27ac, H3K36ac, H4K5ac, H4K8ac, H4K12ac, H4K16ac, H4K91ac, H2Aub or H2Bub.

30. The method of claim 1, wherein the transposase comprises random DNA sequence tags or defined DNA sequence tags.

31. The method of claim 30, wherein the transposase is a Tn5 transposase.

\* \* \* \* \*

SEQUENCE LISTING

```
<160> NUMBER OF SEQ ID NOS: 6

<210> SEQ ID NO 1
<211> LENGTH: 2211
<212> TYPE: DNA
<213> ORGANISM: Artificial Sequence
<220> FEATURE:
<223> OTHER INFORMATION: nucleic acid sequence encoding homemade
      transposase containing a C-terminal intein tag and a chitin-
      binding domain (CBD)

<400> SEQUENCE: 1
atgattacca gtgcactgca tcgtgcggcg gattgggcga aaagcgtgtt ttctagtgct      60
gcgctgggtg atccgcgtcg taccgcgcgt ctggtgaatt ttgcggcgca actggccaaa     120
tatagcggca aaagcattac cattagcagc gaaggcagca aagccatgca ggaaggcgcg     180
tatcgtttta ttcgtaatcc gaacgtgagc gcggaagcga ttcgtaaagc gggtgccatg     240
cagaccgtga aactggccca ggaatttccg gaactgctgg caattgaaga taccacctct     300
ctgagctatc gtcatcaggt ggcggaagaa ctgggcaaac tgggtagcat tcaggataaa     360
agccgtggtt ggtgggtgca tagcgtgctg ctgctggaag cgaccacctt tcgtaccgtg     420
ggcctgctgc atcaagaatg gtggatgcgt ccggatgatc cggcggatgc ggatgaaaaa     480
gaaagcggca aatggctggc cgctgctgca acttcgcgtc tgagaatggg cagcatgatg     540
agcaacgtga ttgcggtgtg cgatcgtgaa gcggatattc atgcgtatct gcaagataaa     600 ctgcccata cgaacgttt tgtggtgcgt agcaaacatc cgcgtaaaga tgtggaaagc       660
ggcctgtatc tgtatgatca cctgaaaaac cagccggaac tgggcggcta tcagattagc     720
```

```
attccgcaga aaggcgtggt ggataaacgt ggcaaacgta aaaccgtccc ggcgcgtaaa    780
gcgagcctga gcctgcgtag cggccgtatt accctgaaac agggcaacat taccctgaac    840
gcggtgctgg ccgaagaaat taatccgccg aaaggcgaaa ccccgctgaa atggctgctg    900
ctgaccagcg agccggtgga aagtctggcc caagcgctgc gtgtgattga tatttatacc    960
catcgttggc gcattgaaga atttcacaaa gcgtggaaaa cgggtgcggg tgcggaacgt   1020
cagcgtatgg aagaaccgga taacctggaa cgtatggtga gcattctgag ctttgtggcg   1080
gtgcgtctgc tgcaactgcg tgaatctttt actccgccgc aagcactgcg tgcgcagggc   1140
ctgctgaaag aagcggaaca cgttgaaagc cagagcgcgg aaaccgtgct gaccccggat   1200
gaatgccaac tgctgggcta tctggataaa ggcaaacgca aacgcaaaga aaaagcgggc   1260
agcctgcaat gggcgtatat ggcgattgcg cgtctgggcg gctttatgga tagcaaacgt   1320
accggcattg cgagctgggg tgcgctgtgg aaggttggg aagcgctgca aagcaaactg   1380
gatggctttc tggccgcgaa agacctgatg gcgcagggca ttaaaatctg catcacggga   1440
gatgcactag ttgccctacc cgagggcgag tcggtacgca tcgccgacat cgtgccgggt   1500
gcgcggccca acagtgacaa cgccatcgac ctgaaagtcc ttgaccggca tggcaatccc   1560
gtgctcgccg accggctgtt ccactccggc gagcatccgg tgtacacggt gcgtacggtc   1620
gaaggtctgc gtgtgacggg caccgcgaac cacccgttgt tgtgtttggt cgacgtcgcc   1680
ggggtgccga ccctgctgtg gaagctgatc gacgaaatca agccgggcga ttacgcggtg   1740
attaacgca gcgcattcag cgtcgactgt gcaggttttg cccgcgggaa acccgaattt   1800
gcgcccacaa cctacacagt cggcgtccct ggactggtgc gtttcttgga agcacaccac   1860
cgagacccgg acgcccaagc tatcgccgac gagctgaccg acgggcggtt ctactacgcg   1920
aaagtcgcca gtgtcaccga cgccggcgtg cagccggtgt atagccttcg tgtcgacacg   1980
gcagaccacg cgtttatcac gaacgggttc gtcagccacg ctactggcct caccggtctg   2040
aactcaggcc tcacgacaaa tcctggtgta tccgcttggc aggtcaacac agcttatact   2100
gcgggacaat tggtcacata taacggcaag acgtataaat gtttgcagcc ccacacctcc   2160
ttggcaggat gggaaccatc caacgttcct gccttgtggc agcttcaatg a            2211
```

<210> SEQ ID NO 2
<211> LENGTH: 1428
<212> TYPE: DNA
<213> ORGANISM: Artificial Sequence
<220> FEATURE:
<223> OTHER INFORMATION: nucleic acid sequence encoding homemade
      transposase

<400> SEQUENCE: 2

```
atgattacca gtgcactgca tcgtgcggcg gattgggcga aaagcgtgtt ttctagtgct     60
gcgctgggtg atccgcgtcg taccgcgcgt ctggtgaatg ttgcggcgca actggccaaa    120
tatagcggca aaagcattac cattagcagc gaaggcagca aagccatgca ggaaggcgcg    180
tatcgtttta ttcgtaatcc gaacgtgagc gcggaagcga ttcgtaaagc gggtgccatg    240
cagaccgtga aactgcccca ggaatttccg gaactgctgg caattgaaga taccacctct    300
ctgagctatc gtcatcaggt ggcggaagaa ctgggcaaac tgggtagcat tcaggataaa    360
agccgtggtt ggtgggtgca tagcgtgctg ctgctggaag cgaccacctt tcgtaccgtg    420
ggcctgctgc atcaagaatg gtggatgcgt ccggatgatc cggcggatgc ggatgaaaaa    480
gaaagcggca aatggctggc cgctgctgca acttcgcgtc tgagaatggg cagcatgatg    540
```

```
agcaacgtga ttgcggtgtg cgatcgtgaa gcggatattc atgcgtatct gcaagataaa    600
ctggcccata acgaacgttt tgtggtgcgt agcaaacatc cgcgtaaaga tgtggaaagc    660
ggcctgtatc tgtatgatca cctgaaaaac cagccggaac tgggcggcta tcagattagc    720
attccgcaga aaggcgtggt ggataaacgt ggcaaacgta aaaaccgtcc ggcgcgtaaa    780
gcgagcctga gcctgcgtag cggccgtatt accctgaaac agggcaacat taccctgaac    840
gcggtgctgg ccgaagaaat taatccgccg aaaggcgaaa ccccgctgaa atggctgctg    900
ctgaccagcg agccggtgga aagtctggcc caagcgctgc gtgtgattga tatttatacc    960
catcgttggc gcattgaaga atttcacaaa gcgtggaaaa cgggtgcggg tgcggaacgt   1020
cagcgtatgg aagaaccgga taacctggaa cgtatggtga gcattctgag ctttgtggcg   1080
gtgcgtctgc tgcaactgcg tgaatctttt actccgccgc aagcactgcg tgcgcagggc   1140
ctgctgaaag aagcggaaca cgttgaaagc cagagcgcgg aaaccgtgct gacccccggat   1200 gaatgccaac tgctgggcta tctggataaa ggcaaacgca aacgcaaaga aaaagcgggc   1260
agcctgcaat gggcgtatat ggcgattgcg cgtctgggcg gctttatgga tagcaaacgt   1320
accggcattg cgagctgggg tgcgctgtgg gaaggttggg aagcgctgca aagcaaactg   1380
gatggctttc tggccgcgaa agacctgatg gcgcagggca ttaaaaatc                1428
```

<210> SEQ ID NO 3  
<211> LENGTH: 8079  
<212> TYPE: DNA  
<213> ORGANISM: Artificial Sequence  
<220> FEATURE:  
<223> OTHER INFORMATION: nucleic acid sequence of vector used to prepare homemade transposase

<400> SEQUENCE: 3

```
aactacgtca ggtggcactt ttcggggaaa tgtgcgcgga acccctattt gtttattttt    60
ctaaatacat tcaaatatgt atccgctcat gagacaataa ccctgataaa tgcttcaata   120
atattgaaaa aggaagagta tgagtattca acatttccgt gtcgccctta ttccctttt    180 tgcggcattt tgccttcctg tttttgctca cccagaaacg ctggtgaaag taaaagatgc   240
tgaagatcag ttgggtgcac gagtgggtta catcgaactg gatctcaaca gcggtaagat   300
ccttgagagt tttcgccccg aagaacgttc tccaatgatg agcacttta aagttctgct   360 atgtggcgcg gtattatccc gtgttgacgc cgggcaagag caactcggtc gccgcataca   420
ctattctcag aatgacttgg ttgagtactc accagtcaca gaaaagcatc ttacggatgg   480
catgacagta agagaattat gcagtgctgc cataaccatg agtgataaca ctgcggccaa   540
cttacttctg acaacgatcg gaggaccgaa ggagctaacc gcttttttgc acaacatggg   600
ggatcatgta actcgccttg atcgttggga accggagctg aatgaagcca taccaaacga   660
cgagcgtgac accacgatgc ctgtagcaat ggcaacaacg ttgcgcaaac tattaactgg   720
cgaactactt actctagctt cccggcaaca attaatagac tggatggagg cggataaagt   780
tgcaggacca cttctgcgct cggcccttcc ggctggctgg tttattgctg ataaatctgg   840
agccggtgag cgtgggtctc gcggtatcat tgcagcactg gggccagatg gtaagccctc   900
ccgtatcgta gttatctaca cgacggggag tcaggcaact atggatgaac gaaatagaca   960
gatcgctgag ataggtgcct cactgattaa gcattggtaa ctgtcagacc aagtttactc  1020
atatatactt tagattgatt taccccggtt gataatcaga aaagccccaa aacaggaag   1080 attgtataag caaatattta aattgtaaac gttaatattt tgttaaaatt cgcgttaaat  1140
```

```
ttttgttaaa tcagctcatt ttttaaccaa taggccgaaa tcggcaaaat cccttataaa    1200
tcaaaagaat agcccgagat agggttgagt gttgttccag tttggaacaa gagtccacta    1260
ttaaagaacg tggactccaa cgtcaaaggg cgaaaaaccg tctatcaggg cgatggccca    1320
ctacgtgaac catcacccaa atcaagtttt ttggggtcga ggtgccgtaa agcactaaat    1380
cggaacccta aagggagccc ccgatttaga gcttgacggg gaaagccggc gaacgtggcg    1440
agaaaggaag ggaagaaagc gaaaggagcg ggcgctaggg cgctggcaag tgtagcggtc    1500
acgctgcgcg taaccaccac acccgccgcg cttaatgcgc cgctacaggg cgcgtaaaag    1560
gatctaggtg aagatccttt ttgataatct catgaccaaa atcccttaac gtgagttttc    1620
gttccactga gcgtcagacc ccgtagaaaa gatcaaagga tcttcttgag atcctttttt    1680
tctgcgcgta atctgctgct tgcaaacaaa aaaaccaccg ctaccagcgg tggtttgttt    1740
gccggatcaa gagctaccaa ctcttttttcc gaaggtaact ggcttcagca gagcgcagat    1800
accaaatact gtccttctag tgtagccgta gttaggccac cacttcaaga actctgtagc    1860
accgcctaca tacctcgctc tgctaatcct gttaccagtg gctgctgcca gtggcgataa    1920
gtcgtgtctt accgggttgg actcaagacg atagttaccg gataaggcgc agcggtcggg    1980
ctgaacgggg ggttcgtgca cacagcccag cttggagcga acgacctaca ccgaactgag    2040
atacctacag cgtgagctat gagaaagcgc cacgcttccc gaagggagaa aggcggacag    2100
gtatccggta agcggcaggg tcggaacagg agagcgcacg agggagcttc caggggggaaa    2160 cgcctggtat ctttatagtc ctgtcgggtt tcgccacctc tgacttgagc gtcgattttt    2220
gtgatgctcg tcagggggc ggagcctatg gaaaaacgcc agcaacgcgg cctttttacg    2280
gttcctggcc ttttgctggc cttttgctca catgttcttt cctgcgttat cccctgattc    2340
tgtggataac cgtattaccg cctttgagtg agctgatacc gctcgccgca gccgaacgac    2400
cgagcgcagc gagtcagtga gcgaggaagc tatggtgcac tctcagtaca atctgctctg    2460
atgccgcata gttaagccag tatacactcc gctatcgcta cgtgactggg tcatggctgc    2520
gccccgacac ccgccaacac ccgctgacgc gccctgacgg gcttgtctgc tcccggcatc    2580
cgcttacaga caagctgtga ccgtctccgg gagctgcatg tgtcagaggt tttcaccgtc    2640
atcaccgaaa cgcgcgaggc agctgcggta aagctcatca gcgtggtcgt gcagcgattc    2700
acagatgtct gcctgttcat ccgcgtccag ctcgttgagt ttctccagaa gcgttaatgt    2760
ctggcttctg ataaagcggg ccatgttaag ggcggttttt tcctgtttgg tcactgatgc    2820
ctccgtgtaa gggggatttc tgttcatggg ggtaatgata ccgatgaaac gagagaggat    2880
gctcacgata cgggttactg atgatgaaca tgcccggtta ctggaacgtt gtgagggtaa    2940
acaactggcg gtatgatgc ggcgggacca gagaaaaatc actcagggtc aatgccagcc    3000
gaacgccagc aagacgtagc ccagcgcgtc ggccgccatg ccggcgataa tggcctgctt    3060
ctcgccgaaa cgtttggtgg cgggaccagt gacgaaggct tgagcgaggg cgtgcaagat    3120
tccgaatacc gcaagcgaca ggccgatcat cgtcgcgctc cagcgaaagc ggtcctcgcc    3180
gaaaatgacc cagagcgctg ccggcacctg tcctacgagt tgcatgataa agaagacagt    3240
cataagtgcg gcgacgatag tcatgccccg cgcccaccgg aaggagctga ctgggttgaa    3300
ggctctcaag ggcatcggtc gagatcccgg tgcctaatga gtgagctaac ttacattaat    3360
tgcgttgcgc tcactgcccg ctttccagtc gggaaacctg tcgtgccagc tgcattaatg    3420
aatcggccaa cgcgcgggga gaggcggttt gcgtattggg cgccagggtg ttttctctt    3480
```

```
tcaccagtga gacgggcaac agctgattgc ccttcaccgc ctggccctga gagagttgca    3540
gcaagcggtc cacgctggtt tgccccagca ggcgaaaatc ctgtttgatg gtggttaacg    3600
gcgggatata acatgagctg tcttcggtat cgtcgtatcc cactaccgag atatccgcac    3660
caacgcgcag cccggactcg gtaatggcgc gcattgcgcc cagcgccatc tgatcgttgg    3720
caaccagcat cgcagtggga acgatgccct cattcagcat ttgcatggtt tgttgaaaac    3780
cggacatggc actccagtcg ccttcccgtt ccgctatcgg ctgaatttga ttgcgagtga    3840
gatatttatg ccagccagcc agacgcagac gcgccgagac agaacttaat gggcccgcta    3900
acagcgcgat ttgctggtga cccaatgcga ccagatgctc cacgcccagt cgcgtaccgt    3960
cttcatggga gaaaataata ctgttgatgg gtgtctggtc agagacatca agaaataacg    4020
ccggaacatt agtgcaggca gcttccacag caatggcatc ctggtcatcc agcggatagt    4080
taatgatcag cccactgacg cgttgcgcga aagattgtg caccgccgct ttacaggctt     4140
cgacgccgct tcgttctacc atcgacacca ccacgctggc acccagttga tcggcgcgag    4200
atttaatcgc cgcgacaatt tgcgacggcg cgtgcagggc cagactggag gtggcaacgc    4260
caatcagcaa cgactgtttg cccgccagtt gttgtgccac gcggttggga atgtaattca    4320
gctccgccat cgccgcttcc acttttttccc gcgttttcgc agaaacgtgg ctggcctggt    4380
tcaccacgcg ggaaacggtc tgataagaga caccggcata ctctgcgaca tcgtataacg    4440
ttactggttt cacattcacc accctgaatt gactctcttc cgggcgctat catgccatac    4500
cgcgaaaggt tttgcgccat tcgatggtgt ccgggatctc gacgctctcc cttatgcgac    4560
tcctgcatta ggaagcagcc cagtagtagg ttgaggccgt tgagcaccgc cgccgcaagg    4620
aatggtgcat gccggcatgc cgcccttttcg tcttcaagaa ttaattccca attccccagg    4680
catcaaataa aacgaaaggc tcagtcgaaa gactgggcct ttcgttttat ctgttgtttg    4740
tcggtgaacg ctctcctgag taggacaaat ccgccgggag cggatttgaa cgttgcgaag    4800
caacggcccg gagggtggcg ggcaggacgc ccgccataaa ctgccaggaa ttaattcccc    4860
aggcatcaaa taaaacgaaa ggctcagtcg aaagactggg cctttcgttt tatctgttgt    4920
ttgtcggtga acgctctcct gagtaggaca aatccgccgg gagcggattt gaacgttgcg    4980
aagcaacggc ccggagggtg gcgggcagga cgcccgccat aaactgccag gaattaattc    5040
cccaggcatc aaataaaacg aaaggctcag tcgaaagact gggcctttcg ttttatctgt    5100
tgtttgtcgg tgaacgctct cctgagtagg acaaatccgc cgggagcgga tttgaacgtt    5160
gcgaagcaac ggcccggagg gtggcgggca ggacgcccgc cataaactgc caggaattaa    5220
ttccccaggc atcaaataaa acgaaaggct cagtcgaaag actgggcctt tcgttttatc    5280
tgttgtttgt cggtgaacgc tctcctgagt aggacaaatc cgccgggagc ggatttgaac    5340
gttgcgaagc aacggcccgg agggtggcgg gcaggacgcc cgccataaac tgccaggaat    5400
taattcccca ggcatcaaat aaaacgaaag gctcagtcga aagactgggc cttttcgttttt   5460 atctgttgtt tgtcggtgaa cgctctcctg agtaggacaa atccgccggg agcggatttg    5520
aacgttgcga agcaacggcc cggagggtgg cgggcaggac gcccgccata aactgccagg    5580 aattgggat cggaattaat tcccggttta accggggat ctcgatcccg cgaaattaat      5640
acgactcact atagggaat tgtgagcgga taacaattcc cctctagata ttttgtttac    5700
tttaagaagg agatatacat atgattacca gtgcactgca tcgtgcgcg gattgggcga    5760 aaagcgtgtt ttctagtgct gcgctggtg atccgcgtcg taccgcgcgt ctggtgaatg    5820
ttgcggcgca actggccaaa tatagcggca aaagcattac cattagcagc gaaggcagca    5880
```

```
aagccatgca ggaaggcgcg tatcgtttta ttcgtaatcc gaacgtgagc gcggaagcga    5940
ttcgtaaagc gggtgccatg cagaccgtga aactggccca ggaatttccg gaactgctgg    6000
caattgaaga taccacctct ctgagctatc gtcatcaggt ggcggaagaa ctgggcaaac    6060
tgggtagcat tcaggataaa agccgtggtt ggtgggtgca tagcgtgctg ctgctggaag    6120
cgaccacctt tcgtaccgtg ggcctgctgc atcaagaatg gtggatgcgt ccggatgatc    6180
cggcggatgc ggatgaaaaa gaaagcggca atggctggc cgctgctgca acttcgcgtc    6240
tgagaatggg cagcatgatg agcaacgtga ttgcggtgtg cgatcgtgaa gcggatattc    6300
atgcgtatct gcaagataaa ctggcccata acgaacgttt tgtggtgcgt agcaaacatc    6360
cgcgtaaaga tgtggaaagc ggcctgtatc tgtatgatca cctgaaaaac cagccggaac    6420
tgggcggcta tcagattagc attccgcaga aaggcgtggt ggataaacgt ggcaaacgta    6480
aaaaccgtcc ggcgcgtaaa gcgagcctga gcctgcgtag cggccgtatt accctgaaac    6540
agggcaacat taccctgaac gcggtgctgg ccgaagaaat taatccgccg aaaggcgaaa    6600
ccccgctgaa atggctgctg ctgaccagcg agccggtgga aagtctggcc caagcgctgc    6660
gtgtgattga tatttatacc catcgttggc gcattgaaga atttcacaaa gcgtggaaaa    6720
cgggtgcggg tgcggaacgt cagcgtatgg aagaaccgga taacctggaa cgtatggtga    6780
gcattctgag ctttgtggcg gtgcgtctgc tgcaactgcg tgaatctttt actccgccgc    6840
aagcactgcg tgcgcagggc ctgctgaaag aagcggaaca cgttgaaagc cagagcgcgg    6900
aaaccgtgct gaccccggat gaatgccaac tgctgggcta tctggataaa ggcaaacgca    6960
aacgcaaaga aaaagcgggc agcctgcaat gggcgtatat ggcgattgcg cgtctgggcg    7020
gctttatgga tagcaaacgt accggcattg cgagctgggg tgcgctgtgg aaggttggg    7080 aagcgctgca aagcaaactg gatggctttc tggccgcgaa agacctgatg gcgcagggca    7140
ttaaaatctg catcacggga gatgcactag ttgccctacc cgagggcgag tcggtacgca    7200
tcgccgacat cgtgccgggt gcgcggccca acagtgacaa cgccatcgac ctgaaagtcc    7260
ttgaccggca tggcaatccc gtgctcgccg accggctgtt ccactccggc gagcatccgg    7320
tgtacacggt gcgtacggtc gaaggtctgc gtgtgacggg caccgcgaac cacccgttgt    7380
tgtgtttggt cgacgtcgcc ggggtgccga ccctgctgtg gaagctgatc gacgaaatca    7440
agccgggcga ttacgcggtg attcaacgca gcgcattcag cgtcgactgt gcaggttttg    7500
cccgcgggaa acccgaattt gcgcccacaa cctacacagt cggcgtccct ggactggtgc    7560
gtttcttgga agcacaccac cgagacccgg acgcccaagc tatcgccgac gagctgaccg    7620
acgggcggtt ctactacgcg aaagtcgcca gtgtcaccga cgccggcgtg cagccggtgt    7680
atagccttcg tgtcgacacg gcagaccacg cgtttatcac gaacgggttc gtcagccacg    7740
ctactggcct caccggtctg aactcaggcc tcacgacaaa tcctggtgta tccgcttggc    7800
aggtcaacac agcttatact gcgggacaat tggtcacata taacggcaag acgtataaat    7860
gtttgcagcc ccacacctcc ttggcaggat gggaaccatc caacgttcct gccttgtggc    7920
agcttcaatg actgcaggaa ggggatccgg ctgctaacaa agcccgaaag gaagctgagt    7980
tggctgctgc caccgctgag caataactag cataacccct ggggcctct aaacgggtct    8040 tgagggggttt tttgctgaaa ggaggaacta tatccggat                          8079
```

<210> SEQ ID NO 4
<211> LENGTH: 19
<212> TYPE: DNA

```
<213> ORGANISM: Artificial Sequence
<220> FEATURE:
<223> OTHER INFORMATION: Tn5MErev

<400> SEQUENCE: 4
ctgtctctta tacacatct                                              19

<210> SEQ ID NO 5
<211> LENGTH: 33
<212> TYPE: DNA
<213> ORGANISM: Artificial Sequence
<220> FEATURE:
<223> OTHER INFORMATION: Tn5ME-A

<400> SEQUENCE: 5
tcgtcggcag cgtcagatgt gtataagaga cag                              33

<210> SEQ ID NO 6
<211> LENGTH: 34
<212> TYPE: DNA
<213> ORGANISM: Artificial Sequence
<220> FEATURE:
<223> OTHER INFORMATION: Tn5ME-B

<400> SEQUENCE: 6
gtctcgtggg ctcggagatg tgtataagag acag                             34
```